Figure 1:
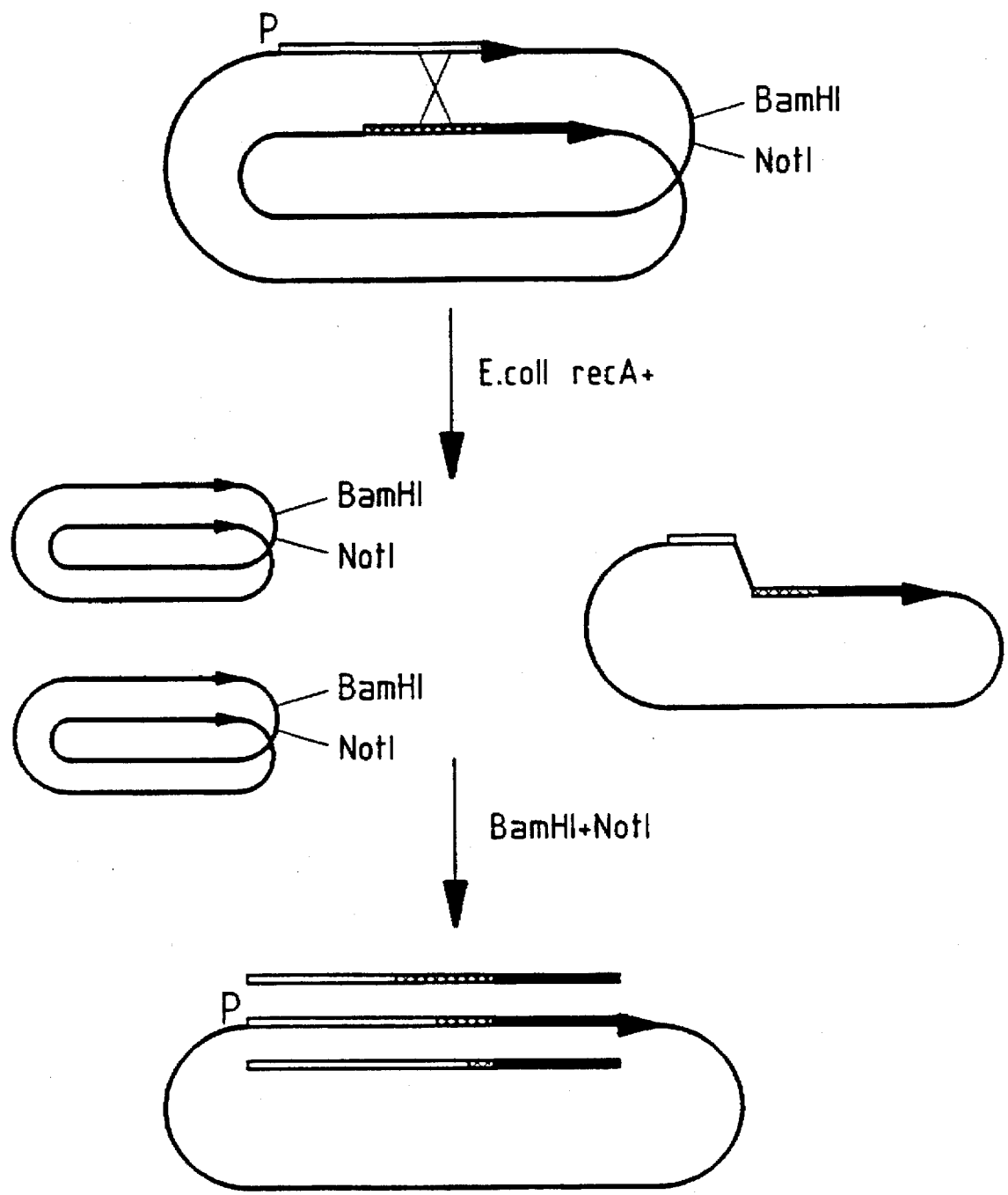

United States Patent [19]

Bosch et al.

[11] Patent Number: 5,736,131
[45] Date of Patent: Apr. 7, 1998

[54] HYBRID TOXIN

[75] Inventors: Hendrik Jan Bosch, Utrecht; Willem Johannes Stiekema, Wageningen, both of Netherlands

[73] Assignee: Sandoz Ltd., Basel, Switzerland

[21] Appl. No.: 602,737

[22] PCT Filed: Sep. 1, 1994

[86] PCT No.: PCT/EP94/02909

§ 371 Date: Feb. 21, 1996

§ 102(e) Date: Feb. 21, 1996

[87] PCT Pub. No.: WO95/06730

PCT Pub. Date: Mar. 9, 1995

[30] Foreign Application Priority Data

Sep. 2, 1993 [GB] United Kingdom ............... 9318207

[51] Int. Cl.$^6$ .................... A01N 63/00; A01N 37/18; C07K 14/325; C12P 21/02
[52] U.S. Cl. .................... 424/93.2; 424/94.461; 424/93.1; 514/12; 514/2; 435/69.7; 435/172.3; 435/320.1; 435/252.3; 435/252.31; 435/254.11; 800/200; 800/205; 800/230; 800/250; 530/350; 536/23.71; 536/23.4
[58] Field of Search .................... 435/69.7, 69.1, 435/320.1, 252.3, 252.31, 254.11; 536/23.4, 23.71; 800/200, 205, 230, 250; 530/350, 825; 424/93.7, 93.2, 93.461, 93.5; 514/2, 12

[56] References Cited

PUBLICATIONS

Honee et al. The C–terminal domain of the toxic fragment of a *Bacillus thuringiensis* crystal protein determines receptor binding. Molecular Microbiology 5(11)2799–2806, 1991.

Nakamura et al. Construction of chimeric insecticidal crystal proteins between the 130 kda amd 135 kda proteins of *Bacillus thuringiensis* subsp. aizawai for analysis of structure–function relationship. Agric. Biol. Chem. 54(3): 715–724 Mar. 1990.

Ge et al. Location of the Bombyx mori specificity domain on a *Bacillus thuringiensis* δo–endotoxin protein. Proc. Nat. Acad. Sci., USA 86: 4037–4041, Jun. 1989.

Bosch et al. Recombinant *Bacillus thuringiensis* crystal proteins with new properties: possibilities for resistance management. Bio/technology 12: 915–918, Sep. 12, 1994.

Visser et al. Domian—function studies of *Bacillus thuringiensis* crystal proteins: a genetic approach. in *Bacillus thuringiensis*, an environmental biopesticide: theory and practice. (eds, Entwistle et al.) Chicester: Wiley & Sons 1993.

*Primary Examiner*—Robert A. Wax
*Assistant Examiner*—Gabriele E. Bugalsky
*Attorney, Agent, or Firm*—Lynn Marcus-Wyner

[57] ABSTRACT

The present invention provides, inter allia, a *B.t.* hybrid toxin fragment comprising at its C-terminal domain III of a first Cry protein or a part of the domain or a protein substantially similar to the domain, with the proviso that the N-terminal region of the fragment is the N-terminal region of a second Cry protein or a part of the region or a protein substantially similar to the region.

18 Claims, 5 Drawing Sheets

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 3567 base pairs

-continued ( B ) TYPE: nucleic acid
( C ) STRANDEDNESS: single
( D ) TOPOLOGY: unknown ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Bacillus thuringiensis ( i x ) FEATURE:
( A ) NAME/KEY: CDS
( B ) LOCATION: 1..3567

( x i ) SEQUENCE DESCRIPTION: SEQ ID NO: 1:

ATG GAG GAA AAT AAT CAA AAT CAA TGC ATA CCT TAC AAT TGT TTA AGT 48
Met Glu Glu Asn Asn Gln Asn Gln Cys Ile Pro Tyr Asn Cys Leu Ser
1 5 10 15

AAT CCT GAA GAA GTA CTT TTG GAT GGA GAA CGG ATA TCA ACT GGT AAT 96
Asn Pro Glu Glu Val Leu Leu Asp Gly Glu Arg Ile Ser Thr Gly Asn
20 25 30

TCA TCA ATT GAT ATT TCT CTG TCA CTT GTT CAG TTT CTG GTA TCT AAC 144
Ser Ser Ile Asp Ile Ser Leu Ser Leu Val Gln Phe Leu Val Ser Asn
35 40 45

TTT GTA CCA GGG GGA GGA TTT TTA GTT GGA TTA ATA GAT TTT GTA TGG 192
Phe Val Pro Gly Gly Gly Phe Leu Val Gly Leu Ile Asp Phe Val Trp
50 55 60

GGA ATA GTT GGC CCT TCT CAA TGG GAT GCA TTT CTA GTA CAA ATT GAA 240
Gly Ile Val Gly Pro Ser Gln Trp Asp Ala Phe Leu Val Gln Ile Glu
65 70 75 80

CAA TTA ATT AAT GAA AGA ATA GCT GAA TTT GCT AGG AAT GCT GCT ATT 288
Gln Leu Ile Asn Glu Arg Ile Ala Glu Phe Ala Arg Asn Ala Ala Ile
85 90 95

GCT AAT TTA GAA GGA TTA GGA AAC AAT TTC AAT ATA TAT GTG GAA GCA 336
Ala Asn Leu Glu Gly Leu Gly Asn Asn Phe Asn Ile Tyr Val Glu Ala
100 105 110

TTT AAA GAA TGG GAA GAA GAT CCT AAT AAT CCA GAA ACC AGG ACC AGA 384
Phe Lys Glu Trp Glu Glu Asp Pro Asn Asn Pro Glu Thr Arg Thr Arg
115 120 125

GTA ATT GAT CGC TTT CGT ATA CTT GAT GGG CTA CTT GAA AGG GAC ATT 432
Val Ile Asp Arg Phe Arg Ile Leu Asp Gly Leu Leu Glu Arg Asp Ile
130 135 140

CCT TCG TTT CGA ATT TCT GGA TTT GAA GTA CCC CTT TTA TCC GTT TAT 480
Pro Ser Phe Arg Ile Ser Gly Phe Glu Val Pro Leu Leu Ser Val Tyr
145 150 155 160

GCT CAA GCG GCC AAT CTG CAT CTA GCT ATA TTA AGA GAT TCT GTA ATT 528
Ala Gln Ala Ala Asn Leu His Leu Ala Ile Leu Arg Asp Ser Val Ile
165 170 175

TTT GGA GAA AGA TGG GGA TTG ACA ACG ATA AAT GTC AAT GAA AAC TAT 576
Phe Gly Glu Arg Trp Gly Leu Thr Thr Ile Asn Val Asn Glu Asn Tyr
180 185 190

AAT AGA CTA ATT AGG CAT ATT GAT GAA TAT GCT GAT CAC TGT GCA AAT 624
Asn Arg Leu Ile Arg His Ile Asp Glu Tyr Ala Asp His Cys Ala Asn
195 200 205

ACG TAT AAT CGG GGA TTA AAT AAT TTA CCG AAA TCT ACG TAT CAA GAT 672
Thr Tyr Asn Arg Gly Leu Asn Asn Leu Pro Lys Ser Thr Tyr Gln Asp
210 215 220

TGG ATA ACA TAT AAT CGA TTA CGG AGA GAC TTA ACA TTG ACT GTA TTA 720
Trp Ile Thr Tyr Asn Arg Leu Arg Arg Asp Leu Thr Leu Thr Val Leu
225 230 235 240

GAT ATC GCC GCT TTC TTT CCA AAC TAT GAC AAT AGG AGA TAT CCA ATT 768

-continued

```
Asp Ile Ala Ala Phe Phe Pro Asn Tyr Asp Asn Arg Arg Tyr Pro Ile
            245                 250                 255

CAG CCA GTT GGT CAA CTA ACA AGG GAA GTT TAT ACG GAC CCA TTA ATT      816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC      864
Asn Phe Asn Pro Gln Leu Gln Ser Val Ala Gln Leu Pro Thr Phe Asn
            275                 280                 285

GTT ATG GAG AGC AGC GCA ATT AGA AAT CCT CAT TTA TTT GAT ATA TTG      912
Val Met Glu Ser Ser Ala Ile Arg Asn Pro His Leu Phe Asp Ile Leu
            290                 295                 300

AAT AAT CTT ACA ATC TTT ACG GAT TGG TTT AGT GTT GGA CGC AAT TTT      960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC     1008
Tyr Trp Gly Gly His Arg Val Ile Ser Ser Leu Ile Gly Gly Gly Asn
            325                 330                 335

ATA ACA TCT CCT ATA TAT GGA AGA GAG GCG AAC CAG GAG CCT CCA AGA     1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT     1104
Ser Phe Thr Phe Asn Gly Pro Val Phe Arg Thr Leu Ser Asn Pro Thr
            355                 360                 365

TTA CGA TTA TTA CAG CAA CCT TGG CCA GCG CCA CCA TTT AAT TTA CGT     1152
Leu Arg Leu Leu Gln Gln Pro Trp Pro Ala Pro Pro Phe Asn Leu Arg
            370                 375                 380

GGT GTT GAA GGA GTA GAA TTT TCT ACA CCT ACA AAT AGC TTT ACG TAT     1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT     1248
Arg Gly Arg Gly Thr Val Asp Ser Leu Thr Glu Leu Pro Pro Glu Asp
            405                 410                 415

AAT AGT GTG CCA CCT CGC GAA GGA TAT AGT CAT CGT TTA TGT CAT GCA     1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA     1344
Thr Phe Val Gln Arg Ser Gly Thr Pro Phe Leu Thr Thr Gly Val Val
            435                 440                 445

TTT TCT TGG ACG CAT CGT AGT GCA ACT CTT ACA AAT ACA ATT GAT CCA     1392
Phe Ser Trp Thr His Arg Ser Ala Thr Leu Thr Asn Thr Ile Asp Pro
            450                 455                 460

GAG AGA ATT AAT CAA ATA CCT TTA GTG AAA GGA TTT AGA GTT TGG GGG     1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT     1488
Gly Thr Ser Val Ile Thr Gly Pro Gly Phe Thr Gly Gly Asp Ile Leu
            485                 490                 495

CGA AGA AAT ACC TTT GGT GAT TTT GTA TCT CTA CAA GTC AAT ATT AAT     1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT     1584
Ser Pro Ile Thr Gln Arg Tyr Arg Leu Arg Phe Arg Tyr Ala Ser Ser
            515                 520                 525

AGG GAT GCA CGA GTT ATA GTA TTA ACA GGA GCG GCA TCC ACA GGA GTG     1632
Arg Asp Ala Arg Val Ile Val Leu Thr Gly Ala Ala Ser Thr Gly Val
530                 535                 540

GGA GGC CAA GTT AGT GTA AAT ATG CCT CTT CAG AAA ACT ATG GAA ATA     1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT     1728
```

-continued

| | | | | | | | | | | | | | | | |
|---|---|---|---|---|---|---|---|---|---|---|---|---|---|---|---|
| Gly | Glu | Asn | Leu | Thr 565 | Ser | Arg | Thr | Phe 570 | Arg | Tyr | Thr | Asp | Phe 575 | Ser | Asn |

| CCT | TTT | TCA | TTT | AGA | GCT | AAT | CCA | GAT | ATA | ATT | GGG | ATA | AGT | GAA | CAA | 1776 |
|---|---|---|---|---|---|---|---|---|---|---|---|---|---|---|---|---|
| Pro | Phe | Ser | Phe 580 | Arg | Ala | Asn | Pro 585 | Asp | Ile | Ile | Gly | Ile 590 | Ser | Glu | Gln | |

| CCT | CTA | TTT | GGT | GCA | GGT | TCT | ATT | AGT | AGC | GGT | GAA | CTT | TAT | ATA | GAT | 1824 |
|---|---|---|---|---|---|---|---|---|---|---|---|---|---|---|---|---|
| Pro | Leu | Phe 595 | Gly | Ala | Gly | Ser | Ile 600 | Ser | Ser | Gly | Glu | Leu 605 | Tyr | Ile | Asp | |

| AAA | ATT | GAA | ATT | ATT | CTA | GCA | GAT | GCA | ACA | TTT | GAA | GCA | GAA | TCT | GAT | 1872 |
|---|---|---|---|---|---|---|---|---|---|---|---|---|---|---|---|---|
| Lys | Ile 610 | Glu | Ile | Ile | Leu | Ala 615 | Asp | Ala | Thr | Phe | Glu 620 | Ala | Glu | Ser | Asp | |

| TTA | GAA | AGA | GCA | CAA | AAG | GCG | GTG | AAT | GCC | CTG | TTT | ACT | TCT | TCC | AAT | 1920 |
|---|---|---|---|---|---|---|---|---|---|---|---|---|---|---|---|---|
| Leu 625 | Glu | Arg | Ala | Gln | Lys 630 | Ala | Val | Asn | Ala | Leu 635 | Phe | Thr | Ser | Ser | Asn 640 | |

| CAA | ATC | GGG | TTA | AAA | ACC | GAT | GTG | ACG | GAT | TAT | CAT | ATT | GAT | CAA | GTA | 1968 |
|---|---|---|---|---|---|---|---|---|---|---|---|---|---|---|---|---|
| Gln | Ile | Gly | Leu | Lys 645 | Thr | Asp | Val | Thr | Asp 650 | Tyr | His | Ile | Asp | Gln 655 | Val | |

| TCC | AAT | TTA | GTG | GAT | TGT | TTA | TCA | GAT | GAA | TTT | TGT | CTG | GAT | GAA | AAG | 2016 |
|---|---|---|---|---|---|---|---|---|---|---|---|---|---|---|---|---|
| Ser | Asn | Leu | Val 660 | Asp | Cys | Leu | Ser | Asp 665 | Glu | Phe | Cys | Leu | Asp 670 | Glu | Lys | |

| CGA | GAA | TTG | TCC | GAG | AAA | GTC | AAA | CAT | GCG | AAG | CGA | CTC | AGT | GAT | GAG | 2064 |
|---|---|---|---|---|---|---|---|---|---|---|---|---|---|---|---|---|
| Arg | Glu | Leu | Ser 675 | Glu | Lys | Val | Lys 680 | His | Ala | Lys | Arg | Leu 685 | Ser | Asp | Glu | |

| CGG | AAT | TTA | CTT | CAA | GAT | CCA | AAC | TTC | AGA | GGG | ATC | AAT | AGA | CAA | CCA | 2112 |
|---|---|---|---|---|---|---|---|---|---|---|---|---|---|---|---|---|
| Arg | Asn 690 | Leu | Leu | Gln | Asp | Pro 695 | Asn | Phe | Arg | Gly | Ile 700 | Asn | Arg | Gln | Pro | |

| GAC | CGT | GGC | TGG | AGA | GGA | AGT | ACA | GAT | ATT | ACC | ATC | CAA | GGA | GGA | GAT | 2160 |
|---|---|---|---|---|---|---|---|---|---|---|---|---|---|---|---|---|
| Asp | Arg | Gly | Trp | Arg 705 | Gly | Ser | Thr | Asp | Ile 710 | Thr | Ile | Gln | Gly | Gly 715 | Asp 720 | |

| GAC | GTA | TTC | AAA | GAG | AAT | TAC | GTC | ACA | CTA | CCG | GGT | ACC | GTT | GAT | GAG | 2208 |
|---|---|---|---|---|---|---|---|---|---|---|---|---|---|---|---|---|
| Asp | Val | Phe | Lys | Glu 725 | Asn | Tyr | Val | Thr | Leu 730 | Pro | Gly | Thr | Val | Asp 735 | Glu | |

| TGC | TAT | CCA | ACG | TAT | TTA | TAT | CAG | AAA | ATA | GAT | GAG | TCG | AAA | TTA | AAA | 2256 |
|---|---|---|---|---|---|---|---|---|---|---|---|---|---|---|---|---|
| Cys | Tyr | Pro | Thr 740 | Tyr | Leu | Tyr | Gln | Lys 745 | Ile | Asp | Glu | Ser | Lys 750 | Leu | Lys | |

| GCT | TAT | ACC | CGT | TAT | GAA | TTA | AGA | GGG | TAT | ATC | GAA | GAT | AGT | CAA | GAC | 2304 |
|---|---|---|---|---|---|---|---|---|---|---|---|---|---|---|---|---|
| Ala | Tyr | Thr 755 | Arg | Tyr | Glu | Leu | Arg 760 | Gly | Tyr | Ile | Glu | Asp 765 | Ser | Gln | Asp | |

| TTA | GAA | ATC | TAT | TTG | ATC | CGT | TAC | AAT | GCA | AAA | CAC | GAA | ATA | GTA | AAT | 2352 |
|---|---|---|---|---|---|---|---|---|---|---|---|---|---|---|---|---|
| Leu | Glu 770 | Ile | Tyr | Leu | Ile | Arg 775 | Tyr | Asn | Ala | Lys | His 780 | Glu | Ile | Val | Asn | |

| GTG | CCA | GGC | ACG | GGT | TCC | TTA | TGG | CCG | CTT | TCA | GCC | CAA | AGT | CCA | ATC | 2400 |
|---|---|---|---|---|---|---|---|---|---|---|---|---|---|---|---|---|
| Val | Pro 785 | Gly | Thr | Gly | Ser | Leu 790 | Trp | Pro | Leu | Ser | Ala 795 | Gln | Ser | Pro | Ile 800 | |

| GGA | AAG | TGT | GGA | GAA | CCG | AAT | CGA | TGC | GCG | CCA | CAC | CTT | GAA | TGG | AAT | 2448 |
|---|---|---|---|---|---|---|---|---|---|---|---|---|---|---|---|---|
| Gly | Lys | Cys | Gly | Glu | Pro 805 | Asn | Arg | Cys | Ala | Pro 810 | His | Leu | Glu | Trp | Asn 815 | |

| CCT | GAT | CTA | GAT | TGT | TCC | TGC | AGA | GAC | GGG | GAA | AAA | TGT | GCA | CAT | CAT | 2496 |
|---|---|---|---|---|---|---|---|---|---|---|---|---|---|---|---|---|
| Pro | Asp | Leu | Asp 820 | Cys | Ser | Cys | Arg | Asp 825 | Gly | Glu | Lys | Cys | Ala 830 | His | His | |

| TCC | CAT | CAT | TTC | ACC | TTG | GAT | ATT | GAT | GTT | GGA | TGT | ACA | GAC | TTA | AAT | 2544 |
|---|---|---|---|---|---|---|---|---|---|---|---|---|---|---|---|---|
| Ser | His | His 835 | Phe | Thr | Leu | Asp | Ile 840 | Asp | Val | Gly | Cys | Thr 845 | Asp | Leu | Asn | |

| GAG | GAC | TTA | GGT | GTA | TGG | GTG | ATA | TTC | AAG | ATT | AAG | ACG | CAA | GAT | GGC | 2592 |
|---|---|---|---|---|---|---|---|---|---|---|---|---|---|---|---|---|
| Glu | Asp 850 | Leu | Gly | Val | Trp | Val 855 | Ile | Phe | Lys | Ile | Lys 860 | Thr | Gln | Asp | Gly | |

| CAT | GCA | AGA | CTA | GGG | AAT | CTA | GAG | TTT | CTC | GAA | GAG | AAA | CCA | TTA | TTA | 2640 |
|---|---|---|---|---|---|---|---|---|---|---|---|---|---|---|---|---|
| His | Ala 865 | Arg | Leu | Gly | Asn 870 | Leu | Glu | Phe | Leu | Glu 875 | Glu | Lys | Pro | Leu | Leu 880 | |

| GGG | GAA | GCA | CTA | GCT | CGT | GTG | AAA | AGA | GCG | GAG | AAG | AAG | TGG | AGA | GAC | 2688 |
|---|---|---|---|---|---|---|---|---|---|---|---|---|---|---|---|---|

|     |     |     |     |     |     |     |     |     |     |     |     |     |     |     |      |
|-----|-----|-----|-----|-----|-----|-----|-----|-----|-----|-----|-----|-----|-----|-----|------|
| Gly | Glu | Ala | Leu | Ala | Arg | Val | Lys | Arg | Ala | Glu | Lys | Lys | Trp | Arg | Asp  |
|     |     |     |     | 885 |     |     |     | 890 |     |     |     |     | 895 |     |      |

| AAA | CGA | GAG | AAA | CTG | CAG | TTG | GAA | ACA | AAT | ATT | GTT | TAT | AAA | GAG | GCA | 2736 |
|-----|-----|-----|-----|-----|-----|-----|-----|-----|-----|-----|-----|-----|-----|-----|-----|------|
| Lys | Arg | Glu | Lys | Leu | Gln | Leu | Glu | Thr | Asn | Ile | Val | Tyr | Lys | Glu | Ala |      |
|     |     |     | 900 |     |     |     |     | 905 |     |     |     |     | 910 |     |     |      |

| AAA | GAA | TCT | GTA | GAT | GCT | TTA | TTT | GTA | AAC | TCT | CAA | TAT | GAT | AGA | TTA | 2784 |
|-----|-----|-----|-----|-----|-----|-----|-----|-----|-----|-----|-----|-----|-----|-----|-----|------|
| Lys | Glu | Ser | Val | Asp | Ala | Leu | Phe | Val | Asn | Ser | Gln | Tyr | Asp | Arg | Leu |      |
|     |     | 915 |     |     |     |     | 920 |     |     |     |     | 925 |     |     |     |      |

| CAA | GTG | GAT | ACG | AAC | ATC | GCG | ATG | ATT | CAT | GCG | GCA | GAT | AAA | CGC | GTT | 2832 |
|-----|-----|-----|-----|-----|-----|-----|-----|-----|-----|-----|-----|-----|-----|-----|-----|------|
| Gln | Val | Asp | Thr | Asn | Ile | Ala | Met | Ile | His | Ala | Ala | Asp | Lys | Arg | Val |      |
|     | 930 |     |     |     |     | 935 |     |     |     |     | 940 |     |     |     |     |      |

| CAT | AGA | ATC | CGG | GAA | GCG | TAT | CTG | CCA | GAG | TTG | TCT | GTG | ATT | CCA | GGT | 2880 |
|-----|-----|-----|-----|-----|-----|-----|-----|-----|-----|-----|-----|-----|-----|-----|-----|------|
| His | Arg | Ile | Arg | Glu | Ala | Tyr | Leu | Pro | Glu | Leu | Ser | Val | Ile | Pro | Gly |      |
| 945 |     |     |     |     | 950 |     |     |     |     | 955 |     |     |     |     | 960 |      |

| GTC | AAT | GCG | GCC | ATT | TTC | GAA | GAA | TTA | GAG | GGA | CGT | ATT | TTT | ACA | GCG | 2928 |
|-----|-----|-----|-----|-----|-----|-----|-----|-----|-----|-----|-----|-----|-----|-----|-----|------|
| Val | Asn | Ala | Ala | Ile | Phe | Glu | Glu | Leu | Glu | Gly | Arg | Ile | Phe | Thr | Ala |      |
|     |     |     |     | 965 |     |     |     |     | 970 |     |     |     |     | 975 |     |      |

| TAT | TCC | TTA | TAT | GAT | GCG | AGA | AAT | GTC | ATT | AAA | AAT | GGC | GAT | TTC | AAT | 2976 |
|-----|-----|-----|-----|-----|-----|-----|-----|-----|-----|-----|-----|-----|-----|-----|-----|------|
| Tyr | Ser | Leu | Tyr | Asp | Ala | Arg | Asn | Val | Ile | Lys | Asn | Gly | Asp | Phe | Asn |      |
|     |     |     | 980 |     |     |     |     | 985 |     |     |     |     | 990 |     |     |      |

| AAT | GGC | TTA | TTA | TGC | TGG | AAC | GTG | AAA | GGT | CAT | GTA | GAT | GTA | GAA | GAG | 3024 |
|-----|-----|-----|-----|-----|-----|-----|-----|-----|-----|-----|-----|-----|-----|-----|-----|------|
| Asn | Gly | Leu | Leu | Cys | Trp | Asn | Val | Lys | Gly | His | Val | Asp | Val | Glu | Glu |      |
|     |     |     | 995 |     |     |     |     | 1000|     |     |     |     | 1005|     |     |      |

| CAA | AAC | AAC | CAC | CGT | TCG | GTC | CTT | GTT | ATC | CCA | GAA | TGG | GAG | GCA | GAA | 3072 |
|-----|-----|-----|-----|-----|-----|-----|-----|-----|-----|-----|-----|-----|-----|-----|-----|------|
| Gln | Asn | Asn | His | Arg | Ser | Val | Leu | Val | Ile | Pro | Glu | Trp | Glu | Ala | Glu |      |
|     |     |     | 1010|     |     |     |     | 1015|     |     |     |     | 1020|     |     |      |

| GTG | TCA | CAA | GAG | GTT | CGT | GTC | TGT | CCA | GGT | CGT | GGC | TAT | ATC | CTT | CGT | 3120 |
|-----|-----|-----|-----|-----|-----|-----|-----|-----|-----|-----|-----|-----|-----|-----|-----|------|
| Val | Ser | Gln | Glu | Val | Arg | Val | Cys | Pro | Gly | Arg | Gly | Tyr | Ile | Leu | Arg |      |
| 1025|     |     |     | 1030|     |     |     | 1035|     |     |     |     |     |     | 1040|      |

| GTC | ACA | GCA | TAT | AAA | GAG | GGA | TAT | GGA | GAG | GGC | TGC | GTA | ACG | ATC | CAT | 3168 |
|-----|-----|-----|-----|-----|-----|-----|-----|-----|-----|-----|-----|-----|-----|-----|-----|------|
| Val | Thr | Ala | Tyr | Lys | Glu | Gly | Tyr | Gly | Glu | Gly | Cys | Val | Thr | Ile | His |      |
|     |     |     |     | 1045|     |     |     |     | 1050|     |     |     |     | 1055|     |      |

| GAG | ATC | GAA | GAC | AAT | ACA | GAC | GAA | CTG | AAA | TTC | AGC | AAC | TGT | GTA | GAA | 3216 |
|-----|-----|-----|-----|-----|-----|-----|-----|-----|-----|-----|-----|-----|-----|-----|-----|------|
| Glu | Ile | Glu | Asp | Asn | Thr | Asp | Glu | Leu | Lys | Phe | Ser | Asn | Cys | Val | Glu |      |
|     |     |     |     | 1060|     |     |     |     | 1065|     |     |     |     | 1070|     |      |

| GAG | GAA | GTA | TAT | CCA | AAC | AAC | ACA | GTA | ACG | TGT | AAT | AAT | TAT | ACT | GGG | 3264 |
|-----|-----|-----|-----|-----|-----|-----|-----|-----|-----|-----|-----|-----|-----|-----|-----|------|
| Glu | Glu | Val | Tyr | Pro | Asn | Asn | Thr | Val | Thr | Cys | Asn | Asn | Tyr | Thr | Gly |      |
|     |     |     | 1075|     |     |     |     | 1080|     |     |     |     | 1085|     |     |      |

| ACT | CAA | GAA | GAA | TAT | GAG | GGT | ACG | TAC | ACT | TCT | CGT | AAT | CAA | GGA | TAT | 3312 |
|-----|-----|-----|-----|-----|-----|-----|-----|-----|-----|-----|-----|-----|-----|-----|-----|------|
| Thr | Gln | Glu | Glu | Tyr | Glu | Gly | Thr | Tyr | Thr | Ser | Arg | Asn | Gln | Gly | Tyr |      |
|     |     | 1090|     |     |     |     | 1095|     |     |     |     | 1100|     |     |     |      |

| GAC | GAA | GCC | TAT | GGT | AAT | AAC | CCT | TCC | GTA | CCA | GCT | GAT | TAC | GCT | TCA | 3360 |
|-----|-----|-----|-----|-----|-----|-----|-----|-----|-----|-----|-----|-----|-----|-----|-----|------|
| Asp | Glu | Ala | Tyr | Gly | Asn | Asn | Pro | Ser | Val | Pro | Ala | Asp | Tyr | Ala | Ser |      |
| 1105|     |     |     |     | 1110|     |     |     |     | 1115|     |     |     |     | 1120|      |

| GTC | TAT | GAA | GAA | AAA | TCG | TAT | ACA | GAT | GGA | CGA | AGA | GAG | AAT | CCT | TGT | 3408 |
|-----|-----|-----|-----|-----|-----|-----|-----|-----|-----|-----|-----|-----|-----|-----|-----|------|
| Val | Tyr | Glu | Glu | Lys | Ser | Tyr | Thr | Asp | Gly | Arg | Arg | Glu | Asn | Pro | Cys |      |
|     |     |     |     | 1125|     |     |     |     | 1130|     |     |     |     | 1135|     |      |

| GAA | TCT | AAC | AGA | GGC | TAT | GGG | GAT | TAC | ACA | CCA | CTA | CCG | GCT | GGT | TAT | 3456 |
|-----|-----|-----|-----|-----|-----|-----|-----|-----|-----|-----|-----|-----|-----|-----|-----|------|
| Glu | Ser | Asn | Arg | Gly | Tyr | Gly | Asp | Tyr | Thr | Pro | Leu | Pro | Ala | Gly | Tyr |      |
|     |     |     | 1140|     |     |     |     | 1145|     |     |     |     | 1150|     |     |      |

| GTA | ACA | AAG | GAT | TTA | GAG | TAC | TTC | CCA | GAG | ACC | GAT | AAG | GTA | TGG | ATT | 3504 |
|-----|-----|-----|-----|-----|-----|-----|-----|-----|-----|-----|-----|-----|-----|-----|-----|------|
| Val | Thr | Lys | Asp | Leu | Glu | Tyr | Phe | Pro | Glu | Thr | Asp | Lys | Val | Trp | Ile |      |
|     |     | 1155|     |     |     |     | 1160|     |     |     |     | 1165|     |     |     |      |

| GAG | ATC | GGA | GAA | ACA | GAA | GGA | ACA | TTC | ATC | GTG | GAT | AGC | GTG | GAA | TTA | 3552 |
|-----|-----|-----|-----|-----|-----|-----|-----|-----|-----|-----|-----|-----|-----|-----|-----|------|
| Glu | Ile | Gly | Glu | Thr | Glu | Gly | Thr | Phe | Ile | Val | Asp | Ser | Val | Glu | Leu |      |
|     |     | 1170|     |     |     |     | 1175|     |     |     |     | 1180|     |     |     |      |

| CTC | CTT | ATG | GAG | GAA |     |     |     |     |     |     |     |     |     |     |     | 3567 |
|-----|-----|-----|-----|-----|-----|-----|-----|-----|-----|-----|-----|-----|-----|-----|-----|------|
| Leu | Leu | Met | Glu | Glu |     |     |     |     |     |     |     |     |     |     |     |      |
| 1185|     |     |     |     |     |     |     |     |     |     |     |     |     |     |     |      |

( 2 ) INFORMATION FOR SEQ ID NO: 2:

( i ) SEQUENCE CHARACTERISTICS:
        ( A ) LENGTH: 1189 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Glu  Glu  Asn  Asn  Gln  Asn  Gln  Cys  Ile  Pro  Tyr  Asn  Cys  Leu  Ser
 1              5                        10                        15
Asn  Pro  Glu  Glu  Val  Leu  Leu  Asp  Gly  Glu  Arg  Ile  Ser  Thr  Gly  Asn
              20                        25                        30
Ser  Ser  Ile  Asp  Ile  Ser  Leu  Ser  Leu  Val  Gln  Phe  Leu  Val  Ser  Asn
         35                        40                        45
Phe  Val  Pro  Gly  Gly  Gly  Phe  Leu  Val  Gly  Leu  Ile  Asp  Phe  Val  Trp
         50                        55                        60
Gly  Ile  Val  Gly  Pro  Ser  Gln  Trp  Asp  Ala  Phe  Leu  Val  Gln  Ile  Glu
 65                        70                        75                        80
Gln  Leu  Ile  Asn  Glu  Arg  Ile  Ala  Glu  Phe  Ala  Arg  Asn  Ala  Ala  Ile
                   85                        90                        95
Ala  Asn  Leu  Glu  Gly  Leu  Gly  Asn  Asn  Phe  Asn  Ile  Tyr  Val  Glu  Ala
              100                       105                       110
Phe  Lys  Glu  Trp  Glu  Glu  Asp  Pro  Asn  Asn  Pro  Glu  Thr  Arg  Thr  Arg
              115                       120                       125
Val  Ile  Asp  Arg  Phe  Arg  Ile  Leu  Asp  Gly  Leu  Leu  Glu  Arg  Asp  Ile
         130                       135                       140
Pro  Ser  Phe  Arg  Ile  Ser  Gly  Phe  Glu  Val  Pro  Leu  Leu  Ser  Val  Tyr
145                       150                       155                       160
Ala  Gln  Ala  Ala  Asn  Leu  His  Leu  Ala  Ile  Leu  Arg  Asp  Ser  Val  Ile
                   165                       170                       175
Phe  Gly  Glu  Arg  Trp  Gly  Leu  Thr  Thr  Ile  Asn  Val  Asn  Glu  Asn  Tyr
              180                       185                       190
Asn  Arg  Leu  Ile  Arg  His  Ile  Asp  Glu  Tyr  Ala  Asp  His  Cys  Ala  Asn
         195                       200                       205
Thr  Tyr  Asn  Arg  Gly  Leu  Asn  Asn  Leu  Pro  Lys  Ser  Thr  Tyr  Gln  Asp
     210                       215                       220
Trp  Ile  Thr  Tyr  Asn  Arg  Leu  Arg  Arg  Asp  Leu  Thr  Leu  Thr  Val  Leu
225                       230                       235                       240
Asp  Ile  Ala  Ala  Phe  Phe  Pro  Asn  Tyr  Asp  Asn  Arg  Arg  Tyr  Pro  Ile
                   245                       250                       255
Gln  Pro  Val  Gly  Gln  Leu  Thr  Arg  Glu  Val  Tyr  Thr  Asp  Pro  Leu  Ile
              260                       265                       270
Asn  Phe  Asn  Pro  Gln  Leu  Gln  Ser  Val  Ala  Gln  Leu  Pro  Thr  Phe  Asn
         275                       280                       285
Val  Met  Glu  Ser  Ser  Ala  Ile  Arg  Asn  Pro  His  Leu  Phe  Asp  Ile  Leu
     290                       295                       300
Asn  Asn  Leu  Thr  Ile  Phe  Thr  Asp  Trp  Phe  Ser  Val  Gly  Arg  Asn  Phe
305                       310                       315                       320
Tyr  Trp  Gly  Gly  His  Arg  Val  Ile  Ser  Ser  Leu  Ile  Gly  Gly  Gly  Asn
                   325                       330                       335
Ile  Thr  Ser  Pro  Ile  Tyr  Gly  Arg  Glu  Ala  Asn  Gln  Glu  Pro  Pro  Arg
              340                       345                       350
Ser  Phe  Thr  Phe  Asn  Gly  Pro  Val  Phe  Arg  Thr  Leu  Ser  Asn  Pro  Thr
         355                       360                       365
```

```
Leu Arg Leu Leu Gln Gln Pro Trp Pro Ala Pro Pro Phe Asn Leu Arg
    370             375             380
Gly Val Glu Gly Val Glu Phe Ser Thr Pro Thr Asn Ser Phe Thr Tyr
385             390             395             400
Arg Gly Arg Gly Thr Val Asp Ser Leu Thr Glu Leu Pro Pro Glu Asp
            405             410             415
Asn Ser Val Pro Pro Arg Glu Gly Tyr Ser His Arg Leu Cys His Ala
        420             425             430
Thr Phe Val Gln Arg Ser Gly Thr Pro Phe Leu Thr Thr Gly Val Val
        435             440             445
Phe Ser Trp Thr His Arg Ser Ala Thr Leu Thr Asn Thr Ile Asp Pro
    450             455             460
Glu Arg Ile Asn Gln Ile Pro Leu Val Lys Gly Phe Arg Val Trp Gly
465             470             475             480
Gly Thr Ser Val Ile Thr Gly Pro Gly Phe Thr Gly Gly Asp Ile Leu
            485             490             495
Arg Arg Asn Thr Phe Gly Asp Phe Val Ser Leu Gln Val Asn Ile Asn
        500             505             510
Ser Pro Ile Thr Gln Arg Tyr Arg Leu Arg Phe Arg Tyr Ala Ser Ser
        515             520             525
Arg Asp Ala Arg Val Ile Val Leu Thr Gly Ala Ala Ser Thr Gly Val
    530             535             540
Gly Gly Gln Val Ser Val Asn Met Pro Leu Gln Lys Thr Met Glu Ile
545             550             555             560
Gly Glu Asn Leu Thr Ser Arg Thr Phe Arg Tyr Thr Asp Phe Ser Asn
            565             570             575
Pro Phe Ser Phe Arg Ala Asn Pro Asp Ile Ile Gly Ile Ser Glu Gln
        580             585             590
Pro Leu Phe Gly Ala Gly Ser Ile Ser Ser Gly Glu Leu Tyr Ile Asp
        595             600             605
Lys Ile Glu Ile Ile Leu Ala Asp Ala Thr Phe Glu Ala Glu Ser Asp
    610             615             620
Leu Glu Arg Ala Gln Lys Ala Val Asn Ala Leu Phe Thr Ser Ser Asn
625             630             635             640
Gln Ile Gly Leu Lys Thr Asp Val Thr Asp Tyr His Ile Asp Gln Val
            645             650             655
Ser Asn Leu Val Asp Cys Leu Ser Asp Glu Phe Cys Leu Asp Glu Lys
        660             665             670
Arg Glu Leu Ser Glu Lys Val Lys His Ala Lys Arg Leu Ser Asp Glu
        675             680             685
Arg Asn Leu Leu Gln Asp Pro Asn Phe Arg Gly Ile Asn Arg Gln Pro
    690             695             700
Asp Arg Gly Trp Arg Gly Ser Thr Asp Ile Thr Ile Gln Gly Gly Asp
705             710             715             720
Asp Val Phe Lys Glu Asn Tyr Val Thr Leu Pro Gly Thr Val Asp Glu
            725             730             735
Cys Tyr Pro Thr Tyr Leu Tyr Gln Lys Ile Asp Glu Ser Lys Leu Lys
        740             745             750
Ala Tyr Thr Arg Tyr Glu Leu Arg Gly Tyr Ile Glu Asp Ser Gln Asp
        755             760             765
Leu Glu Ile Tyr Leu Ile Arg Tyr Asn Ala Lys His Glu Ile Val Asn
    770             775             780
Val Pro Gly Thr Gly Ser Leu Trp Pro Leu Ser Ala Gln Ser Pro Ile
785             790             795             800
```

```
Gly Lys Cys Gly Glu Pro Asn Arg Cys Ala Pro His Leu Glu Trp Asn
            805                 810                 815
Pro Asp Leu Asp Cys Ser Cys Arg Asp Gly Glu Lys Cys Ala His His
            820                 825                 830
Ser His His Phe Thr Leu Asp Ile Asp Val Gly Cys Thr Asp Leu Asn
            835                 840                 845
Glu Asp Leu Gly Val Trp Val Ile Phe Lys Ile Lys Thr Gln Asp Gly
    850                 855                 860
His Ala Arg Leu Gly Asn Leu Glu Phe Leu Glu Lys Pro Leu Leu
865                 870                 875                 880
Gly Glu Ala Leu Ala Arg Val Lys Arg Ala Glu Lys Lys Trp Arg Asp
                885                 890                 895
Lys Arg Glu Lys Leu Gln Leu Glu Thr Asn Ile Val Tyr Lys Glu Ala
            900                 905                 910
Lys Glu Ser Val Asp Ala Leu Phe Val Asn Ser Gln Tyr Asp Arg Leu
            915                 920                 925
Gln Val Asp Thr Asn Ile Ala Met Ile His Ala Ala Asp Lys Arg Val
    930                 935                 940
His Arg Ile Arg Glu Ala Tyr Leu Pro Glu Leu Ser Val Ile Pro Gly
945                 950                 955                 960
Val Asn Ala Ala Ile Phe Glu Glu Leu Glu Gly Arg Ile Phe Thr Ala
                965                 970                 975
Tyr Ser Leu Tyr Asp Ala Arg Asn Val Ile Lys Asn Gly Asp Phe Asn
            980                 985                 990
Asn Gly Leu Leu Cys Trp Asn Val Lys Gly His Val Asp Val Glu Glu
            995                 1000                1005
Gln Asn Asn His Arg Ser Val Leu Val Ile Pro Glu Trp Glu Ala Glu
    1010                1015                1020
Val Ser Gln Glu Val Arg Val Cys Pro Gly Arg Gly Tyr Ile Leu Arg
1025                1030                1035                1040
Val Thr Ala Tyr Lys Glu Gly Tyr Gly Glu Gly Cys Val Thr Ile His
            1045                1050                1055
Glu Ile Glu Asp Asn Thr Asp Glu Leu Lys Phe Ser Asn Cys Val Glu
            1060                1065                1070
Glu Glu Val Tyr Pro Asn Asn Thr Val Thr Cys Asn Asn Tyr Thr Gly
    1075                1080                1085
Thr Gln Glu Glu Tyr Glu Gly Thr Tyr Thr Ser Arg Asn Gln Gly Tyr
    1090                1095                1100
Asp Glu Ala Tyr Gly Asn Asn Pro Ser Val Pro Ala Asp Tyr Ala Ser
1105                1110                1115                1120
Val Tyr Glu Glu Lys Ser Tyr Thr Asp Gly Arg Arg Glu Asn Pro Cys
            1125                1130                1135
Glu Ser Asn Arg Gly Tyr Gly Asp Tyr Thr Pro Leu Pro Ala Gly Tyr
            1140                1145                1150
Val Thr Lys Asp Leu Glu Tyr Phe Pro Glu Thr Asp Lys Val Trp Ile
            1155                1160                1165
Glu Ile Gly Glu Thr Glu Gly Thr Phe Ile Val Asp Ser Val Glu Leu
    1170                1175                1180
Leu Leu Met Glu Glu
1185
```

( 2 ) INFORMATION FOR SEQ ID NO: 3:

( i ) SEQUENCE CHARACTERISTICS:

5,736,131

-continued (A) LENGTH: 3513 base pairs
(B) TYPE: nucleic acid
(C) STRANDEDNESS: single
(D) TOPOLOGY: unknown (ii) MOLECULE TYPE: cDNA (iii) HYPOTHETICAL: NO (iii) ANTI-SENSE: NO (vi) ORIGINAL SOURCE:
    (A) ORGANISM: Bacillus thuringiensis (ix) FEATURE:
    (A) NAME/KEY: CDS
    (B) LOCATION: 1..3513

(xi) SEQUENCE DESCRIPTION: SEQ ID NO: 3:

|

```
GAT ATT ATT TCT TTT TTC AGA AAT TAC GAT TCT AGA TTA TAT CCA ATT          768
Asp Ile Ile Ser Phe Phe Arg Asn Tyr Asp Ser Arg Leu Tyr Pro Ile
            245                 250                 255

CCA ACA AGC TCC CAA TTA ACG CGG GAA GTA TAT ACA GAT CCG GTA ATT          816
Pro Thr Ser Ser Gln Leu Thr Arg Glu Val Tyr Thr Asp Pro Val Ile
        260                 265                 270

AAT ATA ACT GAC TAT AGA GTT GGC CCC AGC TTC GAG AAT ATT GAG AAC          864
Asn Ile Thr Asp Tyr Arg Val Gly Pro Ser Phe Glu Asn Ile Glu Asn
        275                 280                 285

TCA GCC ATT AGA AGC CCC CAC CTT ATG GAC TTC TTA AAT AAT TTG ACC          912
Ser Ala Ile Arg Ser Pro His Leu Met Asp Phe Leu Asn Asn Leu Thr
        290                 295                 300

ATT GAT ACG GAT TTG ATT AGA GGT GTT CAC TAT TGG GCA GGG CAT CGT          960
Ile Asp Thr Asp Leu Ile Arg Gly Val His Tyr Trp Ala Gly His Arg
305                 310                 315                 320

GTA ACT TCT CAT TTT ACA GGT AGT TCT CAA GTG ATA ACA ACC CCT CAA         1008
Val Thr Ser His Phe Thr Gly Ser Ser Gln Val Ile Thr Thr Pro Gln
                325                 330                 335

TAT GGG ATA ACC GCA AAT GCG GAA CCA AGA CGA ACT ATT GCT CCT AGT         1056
Tyr Gly Ile Thr Ala Asn Ala Glu Pro Arg Arg Thr Ile Ala Pro Ser
            340                 345                 350

ACT TTT CCA GGT CTT AAC CTA TTT TAT AGA ACA TTA TCA AAT CCT TTC         1104
Thr Phe Pro Gly Leu Asn Leu Phe Tyr Arg Thr Leu Ser Asn Pro Phe
        355                 360                 365

TTC CGA AGA TCA GAA AAT ATT ACT CCT ACC TTA GGG ATA AAT GTA GTA         1152
Phe Arg Arg Ser Glu Asn Ile Thr Pro Thr Leu Gly Ile Asn Val Val
370                 375                 380

CAG GGA GTA GGG TTC ATT CAA CCA AAT AAT GCT GAA GTT CTA TAT AGA         1200
Gln Gly Val Gly Phe Ile Gln Pro Asn Asn Ala Glu Val Leu Tyr Arg
385                 390                 395                 400

AGT AGG GGG ACA GTA GAT TCT CTT AAT GAG TTA CCA ATT GAT GGT GAG         1248
Ser Arg Gly Thr Val Asp Ser Leu Asn Glu Leu Pro Ile Asp Gly Glu
                405                 410                 415

AAT TCA TTA GTT GGA TAT AGT CAT CGA TTA AGT CAT GTT ACA CTA ACC         1296
Asn Ser Leu Val Gly Tyr Ser His Arg Leu Ser His Val Thr Leu Thr
            420                 425                 430

AGG TCG TTA TAT AAT ACT AAT ATA ACT AGC CTG CCA ACA TTT GTT TGG         1344
Arg Ser Leu Tyr Asn Thr Asn Ile Thr Ser Leu Pro Thr Phe Val Trp
        435                 440                 445

ACA CAT CAC AGT GCT ACT AAT ACA AAT ACA ATT AAT CCA GAT ATT ATT         1392
Thr His His Ser Ala Thr Asn Thr Asn Thr Ile Asn Pro Asp Ile Ile
450                 455                 460

ACA CAA ATA CCT TTA GTG AAA GGA TTT AGA CTT GGT GGT GGC ACC TCT         1440
Thr Gln Ile Pro Leu Val Lys Gly Phe Arg Leu Gly Gly Gly Thr Ser
465                 470                 475                 480

GTC ATT AAA GGA CCA GGA TTT ACA GGA GGG GAT ATC CTT CGA AGA AAT         1488
Val Ile Lys Gly Pro Gly Phe Thr Gly Gly Asp Ile Leu Arg Arg Asn
                485                 490                 495

ACC ATT GGT GAG TTT GTG TCT TTA CAA GTC AAT ATT AAC TCA CCA ATT         1536
Thr Ile Gly Glu Phe Val Ser Leu Gln Val Asn Ile Asn Ser Pro Ile
            500                 505                 510

ACC CAA AGA TAC CGT TTA AGA TTT CGT TAT GCT TCC AGT AGG GAT GCA         1584
Thr Gln Arg Tyr Arg Leu Arg Phe Arg Tyr Ala Ser Ser Arg Asp Ala
        515                 520                 525

CGA ATT ACT GTA GCG ATA GGA GGA CAA ATT AGA GTA GAT ATG ACC CTT         1632
Arg Ile Thr Val Ala Ile Gly Gly Gln Ile Arg Val Asp Met Thr Leu
530                 535                 540

GAA AAA ACC ATG GAA ATT GGG GAG AGC TTA ACA TCT AGA ACA TTT AGC         1680
Glu Lys Thr Met Glu Ile Gly Glu Ser Leu Thr Ser Arg Thr Phe Ser
545                 550                 555                 560
```

| | | | | | | | | | | | | | | | | |
|---|---|---|---|---|---|---|---|---|---|---|---|---|---|---|---|---|
| TAT | ACC | AAT | TTT | AGT | AAT | CCT | TTT | TCA | TTT | AGG | GCT | AAT | CCA | GAT | ATA | 1728 |
| Tyr | Thr | Asn | Phe | Ser | Asn | Pro | Phe | Ser | Phe | Arg | Ala | Asn | Pro | Asp | Ile | |
| | | | | 565 | | | | 570 | | | | | 575 | | | |
| ATT | AGA | ATA | GCT | GAA | GAA | CTT | CCT | ATT | CGT | GGT | GGT | GAG | CTT | TAT | ATA | 1776 |
| Ile | Arg | Ile | Ala | Glu | Glu | Leu | Pro | Ile | Arg | Gly | Gly | Glu | Leu | Tyr | Ile | |
| | | | 580 | | | | | 585 | | | | | 590 | | | |
| GAT | AAA | ATT | GAA | CTT | ATT | CTA | GCA | GAT | GCA | ACA | TTT | GAA | GAA | GAA | TAT | 1824 |
| Asp | Lys | Ile | Glu | Leu | Ile | Leu | Ala | Asp | Ala | Thr | Phe | Glu | Glu | Glu | Tyr | |
| | | 595 | | | | 600 | | | | 605 | | | | | | |
| GAT | TTG | GAA | AGA | GCA | CAG | AAG | GCG | GTG | AAT | GCC | CTG | TTT | ACT | TCT | ACA | 1872 |
| Asp | Leu | Glu | Arg | Ala | Gln | Lys | Ala | Val | Asn | Ala | Leu | Phe | Thr | Ser | Thr | |
| | 610 | | | | 615 | | | | 620 | | | | | | | |
| AAT | CAA | CTA | GGG | CTA | AAA | ACA | GAT | GTG | ACG | GAT | TAT | CAT | ATT | GAT | CAA | 1920 |
| Asn | Gln | Leu | Gly | Leu | Lys | Thr | Asp | Val | Thr | Asp | Tyr | His | Ile | Asp | Gln | |
| 625 | | | | 630 | | | | 635 | | | | | 640 | | | |
| GTT | TCC | AAT | TTA | GTT | GAG | TGT | TTA | TCG | GAT | GAA | TTT | TGT | CTG | GAT | GAA | 1968 |
| Val | Ser | Asn | Leu | Val | Glu | Cys | Leu | Ser | Asp | Glu | Phe | Cys | Leu | Asp | Glu | |
| | | | | 645 | | | | 650 | | | | | 655 | | | |
| AAG | AGA | GAA | TTA | TCC | GAG | AAA | GTC | AAA | CAT | GCG | AAG | CGA | CTC | AGT | GAT | 2016 |
| Lys | Arg | Glu | Leu | Ser | Glu | Lys | Val | Lys | His | Ala | Lys | Arg | Leu | Ser | Asp | |
| | | | 660 | | | | | 665 | | | | | 670 | | | |
| GAA | CGG | AAT | TTA | CTT | CAA | GAT | CCA | AAC | TTC | AGA | GGG | ATC | AAT | AGG | CAA | 2064 |
| Glu | Arg | Asn | Leu | Leu | Gln | Asp | Pro | Asn | Phe | Arg | Gly | Ile | Asn | Arg | Gln | |
| | | 675 | | | | 680 | | | | 685 | | | | | | |
| CCA | GAC | CGT | GGC | TGG | AGA | GGA | AGC | ACG | GAT | ATT | ACT | ATC | CAA | GGT | GGA | 2112 |
| Pro | Asp | Arg | Gly | Trp | Arg | Gly | Ser | Thr | Asp | Ile | Thr | Ile | Gln | Gly | Gly | |
| | 690 | | | | 695 | | | | 700 | | | | | | | |
| GAT | GAC | GTA | TTC | AAA | GAG | AAT | TAC | GTC | ACA | TTA | CCG | GGT | ACC | TTT | GAT | 2160 |
| Asp | Asp | Val | Phe | Lys | Glu | Asn | Tyr | Val | Thr | Leu | Pro | Gly | Thr | Phe | Asp | |
| 705 | | | | 710 | | | | 715 | | | | | 720 | | | |
| GAG | TGC | TAT | CCA | ACG | TAT | TTA | TAT | CAA | AAA | ATA | GAT | GAG | TCG | AAG | TTA | 2208 |
| Glu | Cys | Tyr | Pro | Thr | Tyr | Leu | Tyr | Gln | Lys | Ile | Asp | Glu | Ser | Lys | Leu | |
| | | | | 725 | | | | 730 | | | | | 735 | | | |
| AAA | GCT | TAT | ACC | CGC | TAT | GAA | TTA | AGA | GGG | TAT | ATC | GAG | GAT | AGT | CAA | 2256 |
| Lys | Ala | Tyr | Thr | Arg | Tyr | Glu | Leu | Arg | Gly | Tyr | Ile | Glu | Asp | Ser | Gln | |
| | | | 740 | | | | | 745 | | | | | 750 | | | |
| GAC | TTA | GAA | ATC | TAT | TTA | ATT | CGC | TAC | AAT | GCA | AAA | CAC | GAG | ACA | GTA | 2304 |
| Asp | Leu | Glu | Ile | Tyr | Leu | Ile | Arg | Tyr | Asn | Ala | Lys | His | Glu | Thr | Val | |
| | | | 755 | | | | 760 | | | | | 765 | | | | |
| AAC | GTG | CCA | GGT | ACG | GGT | TCC | TTA | TGG | CCG | CTT | TCA | GCC | CAA | AGT | CCA | 2352 |
| Asn | Val | Pro | Gly | Thr | Gly | Ser | Leu | Trp | Pro | Leu | Ser | Ala | Gln | Ser | Pro | |
| | 770 | | | | 775 | | | | 780 | | | | | | | |
| ATC | GGA | AAG | TGT | GGA | GAA | CCG | AAT | CGA | TGC | GCG | CCA | CAC | CTT | GAA | TGG | 2400 |
| Ile | Gly | Lys | Cys | Gly | Glu | Pro | Asn | Arg | Cys | Ala | Pro | His | Leu | Glu | Trp | |
| 785 | | | | 790 | | | | 795 | | | | | 800 | | | |
| AAT | CCT | AAT | CTA | GAT | TGC | TCC | TGC | AGA | GAC | GGG | GAA | AAA | TGT | GCC | CAT | 2448 |
| Asn | Pro | Asn | Leu | Asp | Cys | Ser | Cys | Arg | Asp | Gly | Glu | Lys | Cys | Ala | His | |
| | | | | 805 | | | | 810 | | | | | 815 | | | |
| CAT | TCC | CAT | CAT | TTC | TCC | TTG | GAC | ATT | GAT | GTT | GGA | TGT | ACA | GAC | TTA | 2496 |
| His | Ser | His | His | Phe | Ser | Leu | Asp | Ile | Asp | Val | Gly | Cys | Thr | Asp | Leu | |
| | | | 820 | | | | | 825 | | | | | 830 | | | |
| AAT | GAG | GAC | TTA | GGT | GTA | TGG | GTG | ATA | TTC | AAG | ATT | AAG | ACA | CAA | GAT | 2544 |
| Asn | Glu | Asp | Leu | Gly | Val | Trp | Val | Ile | Phe | Lys | Ile | Lys | Thr | Gln | Asp | |
| | | | 835 | | | | 840 | | | | | 845 | | | | |
| GGC | TAT | GCA | AGA | CTA | GGA | AAT | CTA | GAG | TTT | CTC | GAA | GAG | AAC | CCA | CTA | 2592 |
| Gly | Tyr | Ala | Arg | Leu | Gly | Asn | Leu | Glu | Phe | Leu | Glu | Glu | Asn | Pro | Leu | |
| | 850 | | | | 855 | | | | 860 | | | | | | | |
| TTA | GGG | GAA | GCA | CTA | GCT | CGT | GTG | AAA | AGA | GCG | GAG | AAA | AAA | TGG | AGA | 2640 |
| Leu | Gly | Glu | Ala | Leu | Ala | Arg | Val | Lys | Arg | Ala | Glu | Lys | Lys | Trp | Arg | |
| 865 | | | | 870 | | | | 875 | | | | | 880 | | | |

| | | | | | | | | | | | | | | | | |
|---|---|---|---|---|---|---|---|---|---|---|---|---|---|---|---|---|
| GAC | AAA | TGC | GAA | AAA | TTG | GAA | TGG | GAA | ACA | AAT | ATT | GTT | TAT | AAA | GAG | 2688 |
| Asp | Lys | Cys | Glu | Lys | Leu | Glu | Trp | Glu | Thr | Asn | Ile | Val | Tyr | Lys | Glu | |
| | | | | 885 | | | | 890 | | | | | | 895 | | |
| GCA | AAA | GAA | TCT | GTA | GAT | GCT | TTA | TTT | GTA | AAC | TCT | CAA | TAT | GAT | AGA | 2736 |
| Ala | Lys | Glu | Ser | Val | Asp | Ala | Leu | Phe | Val | Asn | Ser | Gln | Tyr | Asp | Arg | |
| | 900 | | | | | 905 | | | | | 910 | | | | | |
| TTA | CAA | GCG | GAT | ACG | AAT | ATC | GCG | ATG | ATT | CAT | GCG | GCA | GAT | AAA | CGC | 2784 |
| Leu | Gln | Ala | Asp | Thr | Asn | Ile | Ala | Met | Ile | His | Ala | Ala | Asp | Lys | Arg | |
| | | 915 | | | | | 920 | | | | | 925 | | | | |
| GTT | CAT | AGC | ATT | CGA | GAA | GCG | TAT | CTG | CCA | GAG | CTG | TCT | GTG | ATT | CCG | 2832 |
| Val | His | Ser | Ile | Arg | Glu | Ala | Tyr | Leu | Pro | Glu | Leu | Ser | Val | Ile | Pro | |
| | 930 | | | | | 935 | | | | | 940 | | | | | |
| GGT | GTC | AAT | GCG | GCT | ATT | TTT | GAA | GAA | TTA | GAA | GGG | CGT | ATT | TTC | ACT | 2880 |
| Gly | Val | Asn | Ala | Ala | Ile | Phe | Glu | Glu | Leu | Glu | Gly | Arg | Ile | Phe | Thr | |
| 945 | | | | | 950 | | | | | 955 | | | | | 960 | |
| GCA | TTC | TCC | CTA | TAT | GAT | GCG | AGA | AAT | GTC | ATT | AAA | AAT | GGC | GAT | TTC | 2928 |
| Ala | Phe | Ser | Leu | Tyr | Asp | Ala | Arg | Asn | Val | Ile | Lys | Asn | Gly | Asp | Phe | |
| | | | | 965 | | | | 970 | | | | | 975 | | | |
| AAT | AAT | GGC | TTA | TCA | TGC | TGG | AAC | GTG | AAA | GGG | CAT | GTA | GAT | GTA | GAA | 2976 |
| Asn | Asn | Gly | Leu | Ser | Cys | Trp | Asn | Val | Lys | Gly | His | Val | Asp | Val | Glu | |
| | | | 980 | | | | | 985 | | | | | 990 | | | |
| GAA | CAG | AAC | AAC | CAT | CGT | TCG | GTC | CTT | GTT | GTT | CCA | GAA | TGG | GAA | GCA | 3024 |
| Glu | Gln | Asn | Asn | His | Arg | Ser | Val | Leu | Val | Val | Pro | Glu | Trp | Glu | Ala | |
| | | 995 | | | | | 1000 | | | | | 1005 | | | | |
| GAA | GTG | TCA | CAA | GAA | GTT | CGT | GTT | TGT | CCG | GGT | CGT | GGC | TAT | ATC | CTT | 3072 |
| Glu | Val | Ser | Gln | Glu | Val | Arg | Val | Cys | Pro | Gly | Arg | Gly | Tyr | Ile | Leu | |
| | 1010 | | | | | 1015 | | | | | 1020 | | | | | |
| CGT | GTT | ACA | GCG | TAC | AAA | GAG | GGA | TAT | GGA | GAG | GGC | TGT | GTA | ACG | ATT | 3120 |
| Arg | Val | Thr | Ala | Tyr | Lys | Glu | Gly | Tyr | Gly | Glu | Gly | Cys | Val | Thr | Ile | |
| 1025 | | | | | 1030 | | | | | 1035 | | | | | 1040 | |
| CAT | GAG | ATC | GAA | GAC | AAT | ACA | GAC | GAA | CTG | AAA | TTC | AGC | AAC | TGT | GTA | 3168 |
| His | Glu | Ile | Glu | Asp | Asn | Thr | Asp | Glu | Leu | Lys | Phe | Ser | Asn | Cys | Val | |
| | | | | 1045 | | | | 1050 | | | | | 1055 | | | |
| GAA | GAG | GAA | GTA | TAT | CCA | AAC | AAC | ACG | GTA | ACG | TGT | AAT | AAT | TAT | ACT | 3216 |
| Glu | Glu | Glu | Val | Tyr | Pro | Asn | Asn | Thr | Val | Thr | Cys | Asn | Asn | Tyr | Thr | |
| | | | 1060 | | | | | 1065 | | | | | 1070 | | | |
| GCG | ACT | CAA | GAA | GAA | CAT | GAG | GGT | ACG | TAC | ACT | TCC | CGT | AAT | CGA | GGA | 3264 |
| Ala | Thr | Gln | Glu | Glu | His | Glu | Gly | Thr | Tyr | Thr | Ser | Arg | Asn | Arg | Gly | |
| | | 1075 | | | | | 1080 | | | | | 1085 | | | | |
| TAT | GAC | GAA | GCC | TAT | GAA | AGC | AAT | TCT | TCT | GTA | CAT | GCG | TCA | GTC | TAT | 3312 |
| Tyr | Asp | Glu | Ala | Tyr | Glu | Ser | Asn | Ser | Ser | Val | His | Ala | Ser | Val | Tyr | |
| | 1090 | | | | | 1095 | | | | | 1100 | | | | | |
| GAA | GAA | AAA | TCG | TAT | ACA | GAT | AGA | CGA | AGA | GAG | AAT | CCT | TGT | GAA | TCT | 3360 |
| Glu | Glu | Lys | Ser | Tyr | Thr | Asp | Arg | Arg | Arg | Glu | Asn | Pro | Cys | Glu | Ser | |
| 1105 | | | | | 1110 | | | | | 1115 | | | | | 1120 | |
| AAC | AGA | GGA | TAT | GGG | GAT | TAC | ACA | CCA | CTA | CCA | GCT | GGC | TAT | GTG | ACA | 3408 |
| Asn | Arg | Gly | Tyr | Gly | Asp | Tyr | Thr | Pro | Leu | Pro | Ala | Gly | Tyr | Val | Thr | |
| | | | | 1125 | | | | 1130 | | | | | 1135 | | | |
| AAA | GAA | TTA | GAG | TAC | TTC | CCA | GAA | ACC | GAT | AAG | GTA | TGG | ATT | GAG | ATC | 3456 |
| Lys | Glu | Leu | Glu | Tyr | Phe | Pro | Glu | Thr | Asp | Lys | Val | Trp | Ile | Glu | Ile | |
| | | | | 1140 | | | | 1145 | | | | | 1150 | | | |
| GGA | GAA | ACG | GAA | GGA | ACA | TTC | ATC | GTG | GAC | AGC | GTG | GAA | TTA | CTT | CTT | 3504 |
| Gly | Glu | Thr | Glu | Gly | Thr | Phe | Ile | Val | Asp | Ser | Val | Glu | Leu | Leu | Leu | |
| | | | 1155 | | | | | 1160 | | | | | 1165 | | | |
| ATG | GAG | GAA | | | | | | | | | | | | | | 3513 |
| Met | Glu | Glu | | | | | | | | | | | | | | |
| | 1170 | | | | | | | | | | | | | | | |

( 2 ) INFORMATION FOR SEQ ID NO: 4:

( i ) SEQUENCE CHARACTERISTICS:

( A ) LENGTH: 1171 amino acids
( B ) TYPE: amino acid
( D ) TOPOLOGY: linear ( i i ) MOLECULE TYPE: protein ( x i ) SEQUENCE DESCRIPTION: SEQ ID NO: 4:

| Met | Glu | Ile | Val | Asn | Asn | Gln | Asn | Gln | Cys | Val | Pro | Tyr | Asn | Cys | Leu |
|---|---|---|---|---|---|---|---|---|---|---|---|---|---|---|---|
| 1 | | | | 5 | | | | | 10 | | | | | 15 | |
| Asn | Asn | Pro | Glu | Asn | Glu | Ile | Leu | Asp | Ile | Glu | Arg | Ser | Asn | Ser | Thr |
| | | | 20 | | | | | 25 | | | | | 30 | | |
| Val | Ala | Thr | Asn | Ile | Ala | Leu | Glu | Ile | Ser | Arg | Leu | Leu | Ala | Ser | Ala |
| | | 35 | | | | | 40 | | | | | 45 | | | |
| Thr | Pro | Ile | Gly | Gly | Ile | Leu | Leu | Gly | Leu | Phe | Asp | Ala | Ile | Trp | Gly |
| | 50 | | | | | 55 | | | | | 60 | | | | |
| Ser | Ile | Gly | Pro | Ser | Gln | Trp | Asp | Leu | Phe | Leu | Glu | Gln | Ile | Glu | Leu |
| 65 | | | | | 70 | | | | 75 | | | | | | 80 |
| Leu | Ile | Asp | Gln | Lys | Ile | Glu | Glu | Phe | Ala | Arg | Asn | Gln | Ala | Ile | Ser |
| | | | | 85 | | | | | 90 | | | | | 95 | |
| Arg | Leu | Glu | Gly | Ile | Ser | Ser | Leu | Tyr | Gly | Ile | Tyr | Thr | Glu | Ala | Phe |
| | | | | 100 | | | | | 105 | | | | | 110 | |
| Arg | Glu | Trp | Glu | Ala | Asp | Pro | Thr | Asn | Pro | Ala | Leu | Lys | Glu | Glu | Met |
| | | | 115 | | | | | 120 | | | | | 125 | | |
| Arg | Thr | Gln | Phe | Asn | Asp | Met | Asn | Ser | Ile | Leu | Val | Thr | Ala | Ile | Pro |
| | 130 | | | | | 135 | | | | | 140 | | | | |
| Leu | Phe | Ser | Val | Gln | Asn | Tyr | Gln | Val | Pro | Phe | Leu | Ser | Val | Tyr | Val |
| 145 | | | | | 150 | | | | | 155 | | | | | 160 |
| Gln | Ala | Ala | Asn | Leu | His | Leu | Ser | Val | Leu | Arg | Asp | Val | Ser | Val | Phe |
| | | | | 165 | | | | | 170 | | | | | 175 | |
| Gly | Gln | Ala | Trp | Gly | Phe | Asp | Ile | Ala | Thr | Ile | Asn | Ser | Arg | Tyr | Asn |
| | | | 180 | | | | | 185 | | | | | 190 | | |
| Asp | Leu | Thr | Arg | Leu | Ile | Pro | Ile | Tyr | Thr | Asp | Tyr | Ala | Val | Arg | Trp |
| | | 195 | | | | | 200 | | | | | 205 | | | |
| Tyr | Asn | Thr | Gly | Leu | Asp | Arg | Leu | Pro | Arg | Thr | Gly | Gly | Leu | Arg | Asn |
| | 210 | | | | | 215 | | | | | 220 | | | | |
| Trp | Ala | Arg | Phe | Asn | Gln | Phe | Arg | Arg | Glu | Leu | Thr | Ile | Ser | Val | Leu |
| 225 | | | | | 230 | | | | | 235 | | | | | 240 |
| Asp | Ile | Ile | Ser | Phe | Phe | Arg | Asn | Tyr | Asp | Ser | Arg | Leu | Tyr | Pro | Ile |
| | | | | 245 | | | | | 250 | | | | | 255 | |
| Pro | Thr | Ser | Ser | Gln | Leu | Thr | Arg | Glu | Val | Tyr | Thr | Asp | Pro | Val | Ile |
| | | | 260 | | | | | 265 | | | | | 270 | | |
| Asn | Ile | Thr | Asp | Tyr | Arg | Val | Gly | Pro | Ser | Phe | Glu | Asn | Ile | Glu | Asn |
| | | 275 | | | | | 280 | | | | | 285 | | | |
| Ser | Ala | Ile | Arg | Ser | Pro | His | Leu | Met | Asp | Phe | Leu | Asn | Asn | Leu | Thr |
| | 290 | | | | | 295 | | | | | 300 | | | | |
| Ile | Asp | Thr | Asp | Leu | Ile | Arg | Gly | Val | His | Tyr | Trp | Ala | Gly | His | Arg |
| 305 | | | | | 310 | | | | | 315 | | | | | 320 |
| Val | Thr | Ser | His | Phe | Thr | Gly | Ser | Ser | Gln | Val | Ile | Thr | Thr | Pro | Gln |
| | | | | 325 | | | | | 330 | | | | | 335 | |
| Tyr | Gly | Ile | Thr | Ala | Asn | Ala | Glu | Pro | Arg | Arg | Thr | Ile | Ala | Pro | Ser |
| | | | 340 | | | | | 345 | | | | | 350 | | |
| Thr | Phe | Pro | Gly | Leu | Asn | Leu | Phe | Tyr | Arg | Thr | Leu | Ser | Asn | Pro | Phe |
| | | 355 | | | | | 360 | | | | | 365 | | | |
| Phe | Arg | Arg | Ser | Glu | Asn | Ile | Thr | Pro | Thr | Leu | Gly | Ile | Asn | Val | Val |
| | 370 | | | | | 375 | | | | | 380 | | | | |

-continued

```
Gln Gly Val Gly Phe Ile Gln Pro Asn Asn Ala Glu Val Leu Tyr Arg
385                 390                 395                 400

Ser Arg Gly Thr Val Asp Ser Leu Asn Glu Leu Pro Ile Asp Gly Glu
                405                 410                 415

Asn Ser Leu Val Gly Tyr Ser His Arg Leu Ser His Val Thr Leu Thr
            420                 425                 430

Arg Ser Leu Tyr Asn Thr Asn Ile Thr Ser Leu Pro Thr Phe Val Trp
        435                 440                 445

Thr His His Ser Ala Thr Asn Thr Asn Thr Ile Asn Pro Asp Ile Ile
    450                 455                 460

Thr Gln Ile Pro Leu Val Lys Gly Phe Arg Leu Gly Gly Gly Thr Ser
465                 470                 475                 480

Val Ile Lys Gly Pro Gly Phe Thr Gly Gly Asp Ile Leu Arg Arg Asn
                485                 490                 495

Thr Ile Gly Glu Phe Val Ser Leu Gln Val Asn Ile Asn Ser Pro Ile
            500                 505                 510

Thr Gln Arg Tyr Arg Leu Arg Phe Arg Tyr Ala Ser Ser Arg Asp Ala
        515                 520                 525

Arg Ile Thr Val Ala Ile Gly Gly Gln Ile Arg Val Asp Met Thr Leu
    530                 535                 540

Glu Lys Thr Met Glu Ile Gly Glu Ser Leu Thr Ser Arg Thr Phe Ser
545                 550                 555                 560

Tyr Thr Asn Phe Ser Asn Pro Phe Ser Phe Arg Ala Asn Pro Asp Ile
                565                 570                 575

Ile Arg Ile Ala Glu Glu Leu Pro Ile Arg Gly Gly Glu Leu Tyr Ile
            580                 585                 590

Asp Lys Ile Glu Leu Ile Leu Ala Asp Ala Thr Phe Glu Glu Tyr
        595                 600                 605

Asp Leu Glu Arg Ala Gln Lys Ala Val Asn Ala Leu Phe Thr Ser Thr
    610                 615                 620

Asn Gln Leu Gly Leu Lys Thr Asp Val Thr Asp Tyr His Ile Asp Gln
625                 630                 635                 640

Val Ser Asn Leu Val Glu Cys Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Pro Asn Phe Arg Gly Ile Asn Arg Gln
        675                 680                 685

Pro Asp Arg Gly Trp Arg Gly Ser Thr Asp Ile Thr Ile Gln Gly Gly
    690                 695                 700

Asp Asp Val Phe Lys Glu Asn Tyr Val Thr Leu Pro Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Tyr Thr Arg Tyr Glu Leu Arg Gly Tyr Ile Glu Asp Ser Gln
            740                 745                 750

Asp Leu Glu Ile Tyr Leu Ile Arg Tyr Asn Ala Lys His Glu Thr Val
        755                 760                 765

Asn Val Pro Gly Thr Gly Ser Leu Trp Pro Leu Ser Ala Gln Ser Pro
    770                 775                 780

Ile Gly Lys Cys Gly Glu Pro Asn Arg Cys Ala Pro His Leu Glu Trp
785                 790                 795                 800

Asn Pro Asn Leu Asp Cys Ser Cys Arg Asp Gly Glu Lys Cys Ala His
                805                 810                 815
```

His Ser His His Phe Ser Leu Asp Ile Asp Val Gly Cys Thr Asp Leu
          820                     825                     830

Asn Glu Asp Leu Gly Val Trp Val Ile Phe Lys Ile Lys Thr Gln Asp
        835                     840                     845

Gly Tyr Ala Arg Leu Gly Asn Leu Glu Phe Leu Glu Glu Asn Pro Leu
    850                     855                     860

Leu Gly Glu Ala Leu Ala Arg Val Lys Arg Ala Glu Lys Lys Trp Arg
865                     870                     875                 880

Asp Lys Cys Glu Lys Leu Glu Trp Glu Thr Asn Ile Val Tyr Lys Glu
            885                     890                     895

Ala Lys Glu Ser Val Asp Ala Leu Phe Val Asn Ser Gln Tyr Asp Arg
                900                     905                     910

Leu Gln Ala Asp Thr Asn Ile Ala Met Ile His Ala Ala Asp Lys Arg
        915                     920                     925

Val His Ser Ile Arg Glu Ala Tyr Leu Pro Glu Leu Ser Val Ile Pro
    930                     935                     940

Gly Val Asn Ala Ala Ile Phe Glu Glu Leu Glu Gly Arg Ile Phe Thr
945                     950                     955                 960

Ala Phe Ser Leu Tyr Asp Ala Arg Asn Val Ile Lys Asn Gly Asp Phe
                965                     970                     975

Asn Asn Gly Leu Ser Cys Trp Asn Val Lys Gly His Val Asp Val Glu
            980                     985                     990

Glu Gln Asn Asn His Arg Ser Val Leu Val Val Pro Glu Trp Glu Ala
        995                     1000                    1005

Glu Val Ser Gln Glu Val Arg Val Cys Pro Gly Arg Gly Tyr Ile Leu
    1010                    1015                    1020

Arg Val Thr Ala Tyr Lys Glu Gly Tyr Gly Glu Gly Cys Val Thr Ile
1025                    1030                    1035                1040

His Glu Ile Glu Asp Asn Thr Asp Glu Leu Lys Phe Ser Asn Cys Val
            1045                    1050                    1055

Glu Glu Glu Val Tyr Pro Asn Asn Thr Val Thr Cys Asn Asn Tyr Thr
                1060                    1065                    1070

Ala Thr Gln Glu Glu His Glu Gly Thr Tyr Thr Ser Arg Asn Arg Gly
        1075                    1080                    1085

Tyr Asp Glu Ala Tyr Glu Ser Asn Ser Ser Val His Ala Ser Val Tyr
    1090                    1095                    1100

Glu Glu Lys Ser Tyr Thr Asp Arg Arg Arg Glu Asn Pro Cys Glu Ser
1105                    1110                    1115                1120

Asn Arg Gly Tyr Gly Asp Tyr Thr Pro Leu Pro Ala Gly Tyr Val Thr
                1125                    1130                    1135

Lys Glu Leu Glu Tyr Phe Pro Glu Thr Asp Lys Val Trp Ile Glu Ile
            1140                    1145                    1150

Gly Glu Thr Glu Gly Thr Phe Ile Val Asp Ser Val Glu Leu Leu Leu
        1155                    1160                    1165

Met Glu Glu
    1170

(2) INFORMATION FOR SEQ ID NO: 5:

(i) SEQUENCE CHARACTERISTICS:
        (A) LENGTH: 3558 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iii) ANTI-SENSE: NO (vi) ORIGINAL SOURCE:
    (A) ORGANISM: Hybrid sequence (ix) FEATURE:
    (A) NAME/KEY: CDS
    (B) LOCATION: 1..3558

(xi) SEQUENCE DESCRIPTION: SEQ ID NO: 5:

| | | | | | | | | | | | | | | | | |
|---|---|---|---|---|---|---|---|---|---|---|---|---|---|---|---|---|
| ATG | GAG | ATA | GTG | AAT | AAT | CAG | AAT | CAA | TGC | GTG | CCT | TAT | AAT | TGT | TTA | 48 |
| Met | Glu | Ile | Val | Asn | Asn | Gln | Asn | Gln | Cys | Val | Pro | Tyr | Asn | Cys | Leu | |
| 1 | | | | 5 | | | | | 10 | | | | | 15 | | |
| AAT | AAT | CCT | GAA | AAT | GAG | ATA | TTA | GAT | ATT | GAA | AGG | TCA | AAT | AGT | ACT | 96 |
| Asn | Asn | Pro | Glu | Asn | Glu | Ile | Leu | Asp | Ile | Glu | Arg | Ser | Asn | Ser | Thr | |
| | | | 20 | | | | | 25 | | | | | 30 | | | |
| GTA | GCA | ACA | AAC | ATC | GCC | TTG | GAG | ATT | AGT | CGT | CTG | CTC | GCT | TCC | GCA | 144 |
| Val | Ala | Thr | Asn | Ile | Ala | Leu | Glu | Ile | Ser | Arg | Leu | Leu | Ala | Ser | Ala | |
| | | 35 | | | | | 40 | | | | | 45 | | | | |
| ACT | CCA | ATA | GGG | GGG | ATT | TTA | TTA | GGA | TTG | TTT | GAT | GCA | ATA | TGG | GGG | 192 |
| Thr | Pro | Ile | Gly | Gly | Ile | Leu | Leu | Gly | Leu | Phe | Asp | Ala | Ile | Trp | Gly | |
| | 50 | | | | | 55 | | | | | 60 | | | | | |
| TCT | ATA | GGC | CCT | TCA | CAA | TGG | GAT | TTA | TTT | TTA | GAG | CAA | ATT | GAG | CTA | 240 |
| Ser | Ile | Gly | Pro | Ser | Gln | Trp | Asp | Leu | Phe | Leu | Glu | Gln | Ile | Glu | Leu | |
| 65 | | | | | 70 | | | | | 75 | | | | | 80 | |
| TTG | ATT | GAC | CAA | AAA | ATA | GAG | GAA | TTC | GCT | AGA | AAC | CAG | GCA | ATT | TCT | 288 |
| Leu | Ile | Asp | Gln | Lys | Ile | Glu | Glu | Phe | Ala | Arg | Asn | Gln | Ala | Ile | Ser | |
| | | | | 85 | | | | | 90 | | | | | 95 | | |
| AGA | TTG | GAA | GGG | ATA | AGC | AGT | CTG | TAC | GGA | ATT | TAT | ACA | GAA | GCT | TTT | 336 |
| Arg | Leu | Glu | Gly | Ile | Ser | Ser | Leu | Tyr | Gly | Ile | Tyr | Thr | Glu | Ala | Phe | |
| | | | 100 | | | | | 105 | | | | | 110 | | | |
| AGA | GAG | TGG | GAA | GCA | GAT | CCT | ACT | AAT | CCA | GCA | TTA | AAA | GAA | GAG | ATG | 384 |
| Arg | Glu | Trp | Glu | Ala | Asp | Pro | Thr | Asn | Pro | Ala | Leu | Lys | Glu | Glu | Met | |
| | | 115 | | | | | 120 | | | | | 125 | | | | |
| CGT | ACT | CAA | TTT | AAT | GAC | ATG | AAC | AGT | ATT | CTT | GTA | ACA | GCT | ATT | CCT | 432 |
| Arg | Thr | Gln | Phe | Asn | Asp | Met | Asn | Ser | Ile | Leu | Val | Thr | Ala | Ile | Pro | |
| | 130 | | | | | 135 | | | | | 140 | | | | | |
| CTT | TTT | TCA | GTT | CAA | AAT | TAT | CAA | GTC | CCA | TTT | TTA | TCA | GTA | TAT | GTT | 480 |
| Leu | Phe | Ser | Val | Gln | Asn | Tyr | Gln | Val | Pro | Phe | Leu | Ser | Val | Tyr | Val | |
| 145 | | | | | 150 | | | | | 155 | | | | | 160 | |
| CAA | GCT | GCA | AAT | TTA | CAT | TTA | TCG | GTT | TTG | AGA | GAT | GTT | TCA | GTG | TTT | 528 |
| Gln | Ala | Ala | Asn | Leu | His | Leu | Ser | Val | Leu | Arg | Asp | Val | Ser | Val | Phe | |
| | | | | 165 | | | | | 170 | | | | | 175 | | |
| GGG | CAG | GCT | TGG | GGA | TTT | GAT | ATA | GCA | ACA | ATA | AAT | AGT | CGT | TAT | AAT | 576 |
| Gly | Gln | Ala | Trp | Gly | Phe | Asp | Ile | Ala | Thr | Ile | Asn | Ser | Arg | Tyr | Asn | |
| | | | 180 | | | | | 185 | | | | | 190 | | | |
| GAT | CTG | ACT | AGA | CTT | ATT | CCT | ATA | TAT | ACA | GAT | TAT | GCT | GTA | CGC | TGG | 624 |
| Asp | Leu | Thr | Arg | Leu | Ile | Pro | Ile | Tyr | Thr | Asp | Tyr | Ala | Val | Arg | Trp | |
| | | 195 | | | | | 200 | | | | | 205 | | | | |
| TAC | AAT | ACG | GGA | TTA | GAT | CGC | TTA | CCA | CGA | ACT | GGT | GGG | CTG | CGA | AAC | 672 |
| Tyr | Asn | Thr | Gly | Leu | Asp | Arg | Leu | Pro | Arg | Thr | Gly | Gly | Leu | Arg | Asn | |
| | 210 | | | | | 215 | | | | | 220 | | | | | |
| TGG | GCA | AGA | TTT | AAT | CAG | TTT | AGA | AGA | GAG | TTA | ACA | ATA | TCA | GTA | TTA | 720 |
| Trp | Ala | Arg | Phe | Asn | Gln | Phe | Arg | Arg | Glu | Leu | Thr | Ile | Ser | Val | Leu | |
| 225 | | | | | 230 | | | | | 235 | | | | | 240 | |
| GAT | ATT | ATT | TCT | TTT | TTC | AGA | AAT | TAC | GAT | TCT | AGA | TTA | TAT | CCA | ATT | 768 |
| Asp | Ile | Ile | Ser | Phe | Phe | Arg | Asn | Tyr | Asp | Ser | Arg | Leu | Tyr | Pro | Ile | |
| | | | | 245 | | | | | 250 | | | | | 255 | | |
| CCA | ACA | AGC | TCC | CAA | TTA | ACG | CGG | GAA | GTA | TAT | ACA | GAT | CCG | GTA | ATT | 816 |
| Pro | Thr | Ser | Ser | Gln | Leu | Thr | Arg | Glu | Val | Tyr | Thr | Asp | Pro | Val | Ile | |

-continued

|   |   |   | 260 |   |   |   |   | 265 |   |   |   |   | 270 |   |   |   |
|---|---|---|---|---|---|---|---|---|---|---|---|---|---|---|---|---|
| AAT | ATA | ACT | GAC | TAT | AGA | GTT | GGC | CCC | AGC | TTC | GAG | AAT | ATT | GAG | AAC | 864 |
| Asn | Ile | Thr | Asp | Tyr | Arg | Val | Gly | Pro | Ser | Phe | Glu | Asn | Ile | Glu | Asn |   |
|   |   | 275 |   |   |   |   | 280 |   |   |   |   | 285 |   |   |   |   |
| TCA | GCC | ATT | AGA | AGC | CCC | CAC | CTT | ATG | GAC | TTC | TTA | AAT | AAT | TTG | ACC | 912 |
| Ser | Ala | Ile | Arg | Ser | Pro | His | Leu | Met | Asp | Phe | Leu | Asn | Asn | Leu | Thr |   |
|   |   | 290 |   |   |   |   | 295 |   |   |   |   | 300 |   |   |   |   |
| ATT | GAT | ACG | GAT | TTG | ATT | AGA | GGT | GTT | CAC | TAT | TGG | GCA | GGG | CAT | CGT | 960 |
| Ile | Asp | Thr | Asp | Leu | Ile | Arg | Gly | Val | His | Tyr | Trp | Ala | Gly | His | Arg |   |
| 305 |   |   |   |   | 310 |   |   |   |   | 315 |   |   |   |   | 320 |   |
| GTA | ACT | TCT | CAT | TTT | ACA | GGT | AGT | TCT | CAA | GTG | ATA | ACA | ACC | CCT | CAA | 1008 |
| Val | Thr | Ser | His | Phe | Thr | Gly | Ser | Ser | Gln | Val | Ile | Thr | Thr | Pro | Gln |   |
|   |   |   |   | 325 |   |   |   |   | 330 |   |   |   |   | 335 |   |   |
| TAT | GGG | ATA | ACC | GCA | AAT | GCG | GAA | CCA | AGA | CGA | ACT | ATT | GCT | CCT | AGT | 1056 |
| Tyr | Gly | Ile | Thr | Ala | Asn | Ala | Glu | Pro | Arg | Arg | Thr | Ile | Ala | Pro | Ser |   |
|   |   |   | 340 |   |   |   |   | 345 |   |   |   |   | 350 |   |   |   |
| ACT | TTT | CCA | GGT | CTT | AAC | CTA | TTT | TAT | AGA | ACA | TTA | TCA | AAT | CCT | TTC | 1104 |
| Thr | Phe | Pro | Gly | Leu | Asn | Leu | Phe | Tyr | Arg | Thr | Leu | Ser | Asn | Pro | Phe |   |
|   |   | 355 |   |   |   |   | 360 |   |   |   |   | 365 |   |   |   |   |
| TTC | CGA | AGA | TCA | GAA | AAT | ATT | ACT | CCT | ACC | TTA | GGG | ATA | AAT | GTA | GTA | 1152 |
| Phe | Arg | Arg | Ser | Glu | Asn | Ile | Thr | Pro | Thr | Leu | Gly | Ile | Asn | Val | Val |   |
| 370 |   |   |   |   | 375 |   |   |   |   | 380 |   |   |   |   |   |   |
| CAG | GGA | GTA | GGG | TTC | ATT | CAA | CCA | AAT | AAT | GCT | GAA | GTT | CTA | TAT | AGA | 1200 |
| Gln | Gly | Val | Gly | Phe | Ile | Gln | Pro | Asn | Asn | Ala | Glu | Val | Leu | Tyr | Arg |   |
| 385 |   |   |   |   | 390 |   |   |   |   | 395 |   |   |   |   | 400 |   |
| AGT | AGG | GGG | ACA | GTA | GAT | TCT | CTT | AAT | GAG | TTA | CCA | ATT | GAT | GGT | GAG | 1248 |
| Ser | Arg | Gly | Thr | Val | Asp | Ser | Leu | Asn | Glu | Leu | Pro | Ile | Asp | Gly | Glu |   |
|   |   |   |   | 405 |   |   |   |   | 410 |   |   |   |   | 415 |   |   |
| AAT | TCA | TTA | GTT | GGA | TAT | AGT | CAT | CGA | TTA | AGT | CAT | GTT | ACA | CTA | ACC | 1296 |
| Asn | Ser | Leu | Val | Gly | Tyr | Ser | His | Arg | Leu | Ser | His | Val | Thr | Leu | Thr |   |
|   |   |   | 420 |   |   |   |   | 425 |   |   |   |   | 430 |   |   |   |
| AGG | TCG | TTA | TAT | AAT | ACT | AAT | ATA | ACT | AGC | CTG | CCA | ACA | TTT | GTT | TGG | 1344 |
| Arg | Ser | Leu | Tyr | Asn | Thr | Asn | Ile | Thr | Ser | Leu | Pro | Thr | Phe | Val | Trp |   |
|   |   | 435 |   |   |   |   | 440 |   |   |   |   | 445 |   |   |   |   |
| ACA | CAT | CAC | AGT | GCT | ACT | AAT | ACA | AAT | ACA | ATT | AAT | CCA | GAT | ATT | ATT | 1392 |
| Thr | His | His | Ser | Ala | Thr | Asn | Thr | Asn | Thr | Ile | Asn | Pro | Asp | Ile | Ile |   |
|   |   | 450 |   |   |   |   | 455 |   |   |   |   | 460 |   |   |   |   |
| ACA | CAA | ATA | CCT | TTA | GTG | AAA | GGA | TTT | AGA | GTT | TGG | GGG | GGC | ACC | TCT | 1440 |
| Thr | Gln | Ile | Pro | Leu | Val | Lys | Gly | Phe | Arg | Val | Trp | Gly | Gly | Thr | Ser |   |
| 465 |   |   |   |   | 470 |   |   |   |   | 475 |   |   |   |   | 480 |   |
| GTC | ATT | ACA | GGA | CCA | GGA | TTT | ACA | GGA | GGG | GAT | ATC | CTT | CGA | AGA | AAT | 1488 |
| Val | Ile | Thr | Gly | Pro | Gly | Phe | Thr | Gly | Gly | Asp | Ile | Leu | Arg | Arg | Asn |   |
|   |   |   |   | 485 |   |   |   |   | 490 |   |   |   |   | 495 |   |   |
| ACC | TTT | GGT | GAT | TTT | GTA | TCT | CTA | CAA | GTC | AAT | ATT | AAT | TCA | CCA | ATT | 1536 |
| Thr | Phe | Gly | Asp | Phe | Val | Ser | Leu | Gln | Val | Asn | Ile | Asn | Ser | Pro | Ile |   |
|   |   |   | 500 |   |   |   |   | 505 |   |   |   |   | 510 |   |   |   |
| ACC | CAA | AGA | TAC | CGT | TTA | AGA | TTT | CGT | TAC | GCT | TCC | AGT | AGG | GAT | GCA | 1584 |
| Thr | Gln | Arg | Tyr | Arg | Leu | Arg | Phe | Arg | Tyr | Ala | Ser | Ser | Arg | Asp | Ala |   |
|   |   | 515 |   |   |   |   | 520 |   |   |   |   | 525 |   |   |   |   |
| CGA | GTT | ATA | GTA | TTA | ACA | GGA | GCG | GCA | TCC | ACA | GGA | GTG | GGA | GGC | CAA | 1632 |
| Arg | Val | Ile | Val | Leu | Thr | Gly | Ala | Ala | Ser | Thr | Gly | Val | Gly | Gly | Gln |   |
|   |   | 530 |   |   |   |   | 535 |   |   |   |   | 540 |   |   |   |   |
| GTT | AGT | GTA | AAT | ATG | CCT | CTT | CAG | AAA | ACT | ATG | GAA | ATA | GGG | GAG | AAC | 1680 |
| Val | Ser | Val | Asn | Met | Pro | Leu | Gln | Lys | Thr | Met | Glu | Ile | Gly | Glu | Asn |   |
| 545 |   |   |   |   | 550 |   |   |   |   | 555 |   |   |   |   | 560 |   |
| TTA | ACA | TCT | AGA | ACA | TTT | AGA | TAT | ACC | GAT | TTT | AGT | AAT | CCT | TTT | TCA | 1728 |
| Leu | Thr | Ser | Arg | Thr | Phe | Arg | Tyr | Thr | Asp | Phe | Ser | Asn | Pro | Phe | Ser |   |
|   |   |   |   | 565 |   |   |   |   | 570 |   |   |   |   | 575 |   |   |
| TTT | AGA | GCT | AAT | CCA | GAT | ATA | ATT | GGG | ATA | AGT | GAA | CAA | CCT | CTA | TTT | 1776 |
| Phe | Arg | Ala | Asn | Pro | Asp | Ile | Ile | Gly | Ile | Ser | Glu | Gln | Pro | Leu | Phe |   |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 580 |     |     |     |     | 585 |     |     |     |     | 590 |     |     |     |      |
| GGT | GCA | GGT | TCT | ATT | AGT | AGC | GGT | GAA | CTT | TAT | ATA | GAT | AAA | ATT | GAA | 1824 |
| Gly | Ala | Gly | Ser | Ile | Ser | Ser | Gly | Glu | Leu | Tyr | Ile | Asp | Lys | Ile | Glu |      |
|     |     | 595 |     |     |     | 600 |     |     |     |     | 605 |     |     |     |     |      |
| ATT | ATT | CTA | GCA | GAT | GCA | ACA | TTT | GAA | GCA | GAA | TCT | GAT | TTA | GAA | AGA | 1872 |
| Ile | Ile | Leu | Ala | Asp | Ala | Thr | Phe | Glu | Ala | Glu | Ser | Asp | Leu | Glu | Arg |      |
|     | 610 |     |     |     |     | 615 |     |     |     |     | 620 |     |     |     |     |      |
| GCA | CAA | AAG | GCG | GTG | AAT | GCC | CTG | TTT | ACT | TCT | TCC | AAT | CAA | ATC | GGG | 1920 |
| Ala | Gln | Lys | Ala | Val | Asn | Ala | Leu | Phe | Thr | Ser | Ser | Asn | Gln | Ile | Gly |      |
| 625 |     |     |     |     | 630 |     |     |     |     | 635 |     |     |     |     | 640 |      |
| TTA | AAA | ACC | GAT | GTG | ACG | GAT | TAT | CAT | ATT | GAT | CAA | GTA | TCC | AAT | TTA | 1968 |
| Leu | Lys | Thr | Asp | Val | Thr | Asp | Tyr | His | Ile | Asp | Gln | Val | Ser | Asn | Leu |      |
|     |     |     |     | 645 |     |     |     |     | 650 |     |     |     |     | 655 |     |      |
| GTG | GAT | TGT | TTA | TCA | GAT | GAA | TTT | TGT | CTG | GAT | GAA | AAG | CGA | GAA | TTG | 2016 |
| Val | Asp | Cys | Leu | Ser | Asp | Glu | Phe | Cys | Leu | Asp | Glu | Lys | Arg | Glu | Leu |      |
|     |     |     | 660 |     |     |     |     | 665 |     |     |     |     | 670 |     |     |      |
| TCC | GAG | AAA | GTC | AAA | CAT | GCG | AAG | CGA | CTC | AGT | GAT | GAG | CGG | AAT | TTA | 2064 |
| Ser | Glu | Lys | Val | Lys | His | Ala | Lys | Arg | Leu | Ser | Asp | Glu | Arg | Asn | Leu |      |
|     | 675 |     |     |     |     | 680 |     |     |     |     | 685 |     |     |     |     |      |
| CTT | CAA | GAT | CCA | AAC | TTC | AGA | GGG | ATC | AAT | AGA | CAA | CCA | GAC | CGT | GGC | 2112 |
| Leu | Gln | Asp | Pro | Asn | Phe | Arg | Gly | Ile | Asn | Arg | Gln | Pro | Asp | Arg | Gly |      |
| 690 |     |     |     |     | 695 |     |     |     |     | 700 |     |     |     |     |     |      |
| TGG | AGA | GGA | AGT | ACA | GAT | ATT | ACC | ATC | CAA | GGA | GGA | GAT | GAC | GTA | TTC | 2160 |
| Trp | Arg | Gly | Ser | Thr | Asp | Ile | Thr | Ile | Gln | Gly | Gly | Asp | Asp | Val | Phe |      |
| 705 |     |     |     | 710 |     |     |     |     | 715 |     |     |     |     | 720 |     |      |
| AAA | GAG | AAT | TAC | GTC | ACA | CTA | CCG | GGT | ACC | GTT | GAT | GAG | TGC | TAT | CCA | 2208 |
| Lys | Glu | Asn | Tyr | Val | Thr | Leu | Pro | Gly | Thr | Val | Asp | Glu | Cys | Tyr | Pro |      |
|     |     |     |     | 725 |     |     |     |     | 730 |     |     |     |     | 735 |     |      |
| ACG | TAT | TTA | TAT | CAG | AAA | ATA | GAT | GAG | TCG | AAA | TTA | AAA | GCT | TAT | ACC | 2256 |
| Thr | Tyr | Leu | Tyr | Gln | Lys | Ile | Asp | Glu | Ser | Lys | Leu | Lys | Ala | Tyr | Thr |      |
|     |     | 740 |     |     |     |     | 745 |     |     |     |     | 750 |     |     |     |      |
| CGT | TAT | GAA | TTA | AGA | GGG | TAT | ATC | GAA | GAT | AGT | CAA | GAC | TTA | GAA | ATC | 2304 |
| Arg | Tyr | Glu | Leu | Arg | Gly | Tyr | Ile | Glu | Asp | Ser | Gln | Asp | Leu | Glu | Ile |      |
|     | 755 |     |     |     |     | 760 |     |     |     |     | 765 |     |     |     |     |      |
| TAT | TTG | ATC | CGT | TAC | AAT | GCA | AAA | CAC | GAA | ATA | GTA | AAT | GTG | CCA | GGC | 2352 |
| Tyr | Leu | Ile | Arg | Tyr | Asn | Ala | Lys | His | Glu | Ile | Val | Asn | Val | Pro | Gly |      |
| 770 |     |     |     |     | 775 |     |     |     |     | 780 |     |     |     |     |     |      |
| ACG | GGT | TCC | TTA | TGG | CCG | CTT | TCA | GCC | CAA | AGT | CCA | ATC | GGA | AAG | TGT | 2400 |
| Thr | Gly | Ser | Leu | Trp | Pro | Leu | Ser | Ala | Gln | Ser | Pro | Ile | Gly | Lys | Cys |      |
| 785 |     |     |     | 790 |     |     |     |     | 795 |     |     |     |     | 800 |     |      |
| GGA | GAA | CCG | AAT | CGA | TGC | GCG | CCA | CAC | CTT | GAA | TGG | AAT | CCT | GAT | CTA | 2448 |
| Gly | Glu | Pro | Asn | Arg | Cys | Ala | Pro | His | Leu | Glu | Trp | Asn | Pro | Asp | Leu |      |
|     |     |     |     | 805 |     |     |     |     | 810 |     |     |     |     | 815 |     |      |
| GAT | TGT | TCC | TGC | AGA | GAC | GGG | GAA | AAA | TGT | GCA | CAT | CAT | TCC | CAT | CAT | 2496 |
| Asp | Cys | Ser | Cys | Arg | Asp | Gly | Glu | Lys | Cys | Ala | His | His | Ser | His | His |      |
|     |     | 820 |     |     |     |     | 825 |     |     |     |     | 830 |     |     |     |      |
| TTC | ACC | TTG | GAT | ATT | GAT | GTT | GGA | TGT | ACA | GAC | TTA | AAT | GAG | GAC | TTA | 2544 |
| Phe | Thr | Leu | Asp | Ile | Asp | Val | Gly | Cys | Thr | Asp | Leu | Asn | Glu | Asp | Leu |      |
|     | 835 |     |     |     |     | 840 |     |     |     |     | 845 |     |     |     |     |      |
| GGT | GTA | TGG | GTG | ATA | TTC | AAG | ATT | AAG | ACG | CAA | GAT | GGC | CAT | GCA | AGA | 2592 |
| Gly | Val | Trp | Val | Ile | Phe | Lys | Ile | Lys | Thr | Gln | Asp | Gly | His | Ala | Arg |      |
| 850 |     |     |     |     | 855 |     |     |     |     | 860 |     |     |     |     |     |      |
| CTA | GGG | AAT | CTA | GAG | TTT | CTC | GAA | GAG | AAA | CCA | TTA | TTA | GGG | GAA | GCA | 2640 |
| Leu | Gly | Asn | Leu | Glu | Phe | Leu | Glu | Glu | Lys | Pro | Leu | Leu | Gly | Glu | Ala |      |
| 865 |     |     |     | 870 |     |     |     |     | 875 |     |     |     |     | 880 |     |      |
| CTA | GCT | CGT | GTG | AAA | AGA | GCG | GAG | AAG | AAG | TGG | AGA | GAC | AAA | CGA | GAG | 2688 |
| Leu | Ala | Arg | Val | Lys | Arg | Ala | Glu | Lys | Lys | Trp | Arg | Asp | Lys | Arg | Glu |      |
|     |     |     |     | 885 |     |     |     |     | 890 |     |     |     |     | 895 |     |      |
| AAA | CTG | CAG | TTG | GAA | ACA | AAT | ATT | GTT | TAT | AAA | GAG | GCA | AAA | GAA | TCT | 2736 |
| Lys | Leu | Gln | Leu | Glu | Thr | Asn | Ile | Val | Tyr | Lys | Glu | Ala | Lys | Glu | Ser |      |

|  |  |  | 900 |  |  |  | 905 |  |  |  | 910 |  |  |  |  |
|---|---|---|---|---|---|---|---|---|---|---|---|---|---|---|---|
| GTA | GAT | GCT | TTA | TTT | GTA | AAC | TCT | CAA | TAT | GAT | AGA | TTA | CAA | GTG | GAT | 2784 |
| Val | Asp | Ala | Leu | Phe | Val | Asn | Ser | Gln | Tyr | Asp | Arg | Leu | Gln | Val | Asp |  |
|  |  | 915 |  |  |  |  | 920 |  |  |  |  | 925 |  |  |  |  |
| ACG | AAC | ATC | GCG | ATG | ATT | CAT | GCG | GCA | GAT | AAA | CGC | GTT | CAT | AGA | ATC | 2832 |
| Thr | Asn | Ile | Ala | Met | Ile | His | Ala | Ala | Asp | Lys | Arg | Val | His | Arg | Ile |  |
|  | 930 |  |  |  |  | 935 |  |  |  |  | 940 |  |  |  |  |  |
| CGG | GAA | GCG | TAT | CTG | CCA | GAG | TTG | TCT | GTG | ATT | CCA | GGT | GTC | AAT | GCG | 2880 |
| Arg | Glu | Ala | Tyr | Leu | Pro | Glu | Leu | Ser | Val | Ile | Pro | Gly | Val | Asn | Ala |  |
| 945 |  |  |  |  | 950 |  |  |  |  | 955 |  |  |  |  | 960 |  |
| GCC | ATT | TTC | GAA | GAA | TTA | GAG | GGA | CGT | ATT | TTT | ACA | GCG | TAT | TCC | TTA | 2928 |
| Ala | Ile | Phe | Glu | Glu | Leu | Glu | Gly | Arg | Ile | Phe | Thr | Ala | Tyr | Ser | Leu |  |
|  |  |  |  | 965 |  |  |  |  | 970 |  |  |  |  | 975 |  |  |
| TAT | GAT | GCG | AGA | AAT | GTC | ATT | AAA | AAT | GGC | GAT | TTC | AAT | AAT | GGC | TTA | 2976 |
| Tyr | Asp | Ala | Arg | Asn | Val | Ile | Lys | Asn | Gly | Asp | Phe | Asn | Asn | Gly | Leu |  |
|  |  |  | 980 |  |  |  |  | 985 |  |  |  |  | 990 |  |  |  |
| TTA | TGC | TGG | AAC | GTG | AAA | GGT | CAT | GTA | GAT | GTA | GAA | GAG | CAA | AAC | AAC | 3024 |
| Leu | Cys | Trp | Asn | Val | Lys | Gly | His | Val | Asp | Val | Glu | Glu | Gln | Asn | Asn |  |
|  |  | 995 |  |  |  |  | 1000 |  |  |  |  | 1005 |  |  |  |  |
| CAC | CGT | TCG | GTC | CTT | GTT | ATC | CCA | GAA | TGG | GAG | GCA | GAA | GTG | TCA | CAA | 3072 |
| His | Arg | Ser | Val | Leu | Val | Ile | Pro | Glu | Trp | Glu | Ala | Glu | Val | Ser | Gln |  |
|  | 1010 |  |  |  |  | 1015 |  |  |  |  | 1020 |  |  |  |  |  |
| GAG | GTT | CGT | GTC | TGT | CCA | GGT | CGT | GGC | TAT | ATC | CTT | CGT | GTC | ACA | GCA | 3120 |
| Glu | Val | Arg | Val | Cys | Pro | Gly | Arg | Gly | Tyr | Ile | Leu | Arg | Val | Thr | Ala |  |
| 1025 |  |  |  |  | 1030 |  |  |  |  | 1035 |  |  |  |  | 1040 |  |
| TAT | AAA | GAG | GGA | TAT | GGA | GAG | GGC | TGC | GTA | ACG | ATC | CAT | GAG | ATC | GAA | 3168 |
| Tyr | Lys | Glu | Gly | Tyr | Gly | Glu | Gly | Cys | Val | Thr | Ile | His | Glu | Ile | Glu |  |
|  |  |  |  | 1045 |  |  |  |  | 1050 |  |  |  |  | 1055 |  |  |
| GAC | AAT | ACA | GAC | GAA | CTG | AAA | TTC | AGC | AAC | TGT | GTA | GAA | GAG | GAA | GTA | 3216 |
| Asp | Asn | Thr | Asp | Glu | Leu | Lys | Phe | Ser | Asn | Cys | Val | Glu | Glu | Glu | Val |  |
|  |  |  | 1060 |  |  |  |  | 1065 |  |  |  |  | 1070 |  |  |  |
| TAT | CCA | AAC | AAC | ACA | GTA | ACG | TGT | AAT | AAT | TAT | ACT | GGG | ACT | CAA | GAA | 3264 |
| Tyr | Pro | Asn | Asn | Thr | Val | Thr | Cys | Asn | Asn | Tyr | Thr | Gly | Thr | Gln | Glu |  |
|  |  | 1075 |  |  |  |  | 1080 |  |  |  |  | 1085 |  |  |  |  |
| GAA | TAT | GAG | GGT | ACG | TAC | ACT | TCT | CGT | AAT | CAA | GGA | TAT | GAC | GAA | GCC | 3312 |
| Glu | Tyr | Glu | Gly | Thr | Tyr | Thr | Ser | Arg | Asn | Gln | Gly | Tyr | Asp | Glu | Ala |  |
|  | 1090 |  |  |  |  | 1095 |  |  |  |  | 1100 |  |  |  |  |  |
| TAT | GGT | AAT | AAC | CCT | TCC | GTA | CCA | GCT | GAT | TAC | GCT | TCA | GTC | TAT | GAA | 3360 |
| Tyr | Gly | Asn | Asn | Pro | Ser | Val | Pro | Ala | Asp | Tyr | Ala | Ser | Val | Tyr | Glu |  |
| 1105 |  |  |  |  | 1110 |  |  |  |  | 1115 |  |  |  |  | 1120 |  |
| GAA | AAA | TCG | TAT | ACA | GAT | GGA | CGA | AGA | GAG | AAT | CCT | TGT | GAA | TCT | AAC | 3408 |
| Glu | Lys | Ser | Tyr | Thr | Asp | Gly | Arg | Arg | Glu | Asn | Pro | Cys | Glu | Ser | Asn |  |
|  |  |  |  | 1125 |  |  |  |  | 1130 |  |  |  |  | 1135 |  |  |
| AGA | GGC | TAT | GGG | GAT | TAC | ACA | CCA | CTA | CCG | GCT | GGT | TAT | GTA | ACA | AAG | 3456 |
| Arg | Gly | Tyr | Gly | Asp | Tyr | Thr | Pro | Leu | Pro | Ala | Gly | Tyr | Val | Thr | Lys |  |
|  |  |  | 1140 |  |  |  |  | 1145 |  |  |  |  | 1150 |  |  |  |
| GAT | TTA | GAG | TAC | TTC | CCA | GAG | ACC | GAT | AAG | GTA | TGG | ATT | GAG | ATC | GGA | 3504 |
| Asp | Leu | Glu | Tyr | Phe | Pro | Glu | Thr | Asp | Lys | Val | Trp | Ile | Glu | Ile | Gly |  |
|  |  | 1155 |  |  |  |  | 1160 |  |  |  |  | 1165 |  |  |  |  |
| GAA | ACA | GAA | GGA | ACA | TTC | ATC | GTG | GAT | AGC | GTG | GAA | TTA | CTC | CTT | ATG | 3552 |
| Glu | Thr | Glu | Gly | Thr | Phe | Ile | Val | Asp | Ser | Val | Glu | Leu | Leu | Leu | Met |  |
|  | 1170 |  |  |  |  | 1175 |  |  |  |  | 1180 |  |  |  |  |  |
| GAG | GAA |  |  |  |  |  |  |  |  |  |  |  |  |  |  | 3558 |
| Glu | Glu |  |  |  |  |  |  |  |  |  |  |  |  |  |  |  |
| 1185 |  |  |  |  |  |  |  |  |  |  |  |  |  |  |  |  |

( 2 ) INFORMATION FOR SEQ ID NO: 6:

( i ) SEQUENCE CHARACTERISTICS:

( A ) LENGTH: 1186 amino acids ( B ) TYPE: amino acid ( D ) TOPOLOGY: linear ( i i ) MOLECULE TYPE: protein ( x i ) SEQUENCE DESCRIPTION: SEQ ID NO: 6:

```
Met Glu Ile Val Asn Asn Gln Asn Gln Cys Val Pro Tyr Asn Cys Leu
 1               5                  10                  15
Asn Asn Pro Glu Asn Glu Ile Leu Asp Ile Glu Arg Ser Asn Ser Thr
            20                  25                  30
Val Ala Thr Asn Ile Ala Leu Glu Ile Ser Arg Leu Leu Ala Ser Ala
        35                  40                  45
Thr Pro Ile Gly Gly Ile Leu Leu Gly Leu Phe Asp Ala Ile Trp Gly
    50                  55                  60
Ser Ile Gly Pro Ser Gln Trp Asp Leu Phe Leu Glu Gln Ile Glu Leu
65                  70                  75                  80
Leu Ile Asp Gln Lys Ile Glu Glu Phe Ala Arg Asn Gln Ala Ile Ser
                85                  90                  95
Arg Leu Glu Gly Ile Ser Ser Leu Tyr Gly Ile Tyr Thr Glu Ala Phe
            100                 105                 110
Arg Glu Trp Glu Ala Asp Pro Thr Asn Pro Ala Leu Lys Glu Glu Met
        115                 120                 125
Arg Thr Gln Phe Asn Asp Met Asn Ser Ile Leu Val Thr Ala Ile Pro
    130                 135                 140
Leu Phe Ser Val Gln Asn Tyr Gln Val Pro Phe Leu Ser Val Tyr Val
145                 150                 155                 160
Gln Ala Ala Asn Leu His Leu Ser Val Leu Arg Asp Val Ser Val Phe
                165                 170                 175
Gly Gln Ala Trp Gly Phe Asp Ile Ala Thr Ile Asn Ser Arg Tyr Asn
            180                 185                 190
Asp Leu Thr Arg Leu Ile Pro Ile Tyr Thr Asp Tyr Ala Val Arg Trp
        195                 200                 205
Tyr Asn Thr Gly Leu Asp Arg Leu Pro Arg Thr Gly Gly Leu Arg Asn
    210                 215                 220
Trp Ala Arg Phe Asn Gln Phe Arg Arg Glu Leu Thr Ile Ser Val Leu
225                 230                 235                 240
Asp Ile Ile Ser Phe Phe Arg Asn Tyr Asp Ser Arg Leu Tyr Pro Ile
                245                 250                 255
Pro Thr Ser Ser Gln Leu Thr Arg Glu Val Tyr Thr Asp Pro Val Ile
            260                 265                 270
Asn Ile Thr Asp Tyr Arg Val Gly Pro Ser Phe Glu Asn Ile Glu Asn
        275                 280                 285
Ser Ala Ile Arg Ser Pro His Leu Met Asp Phe Leu Asn Asn Leu Thr
    290                 295                 300
Ile Asp Thr Asp Leu Ile Arg Gly Val His Tyr Trp Ala Gly His Arg
305                 310                 315                 320
Val Thr Ser His Phe Thr Gly Ser Ser Gln Val Ile Thr Thr Pro Gln
                325                 330                 335
Tyr Gly Ile Thr Ala Asn Ala Glu Pro Arg Arg Thr Ile Ala Pro Ser
            340                 345                 350
Thr Phe Pro Gly Leu Asn Leu Phe Tyr Arg Thr Leu Ser Asn Pro Phe
        355                 360                 365
Phe Arg Arg Ser Glu Asn Ile Thr Pro Thr Leu Gly Ile Asn Val Val
    370                 375                 380
Gln Gly Val Gly Phe Ile Gln Pro Asn Asn Ala Glu Val Leu Tyr Arg
385                 390                 395                 400
```

```
Ser  Arg  Gly  Thr  Val  Asp  Ser  Leu  Asn  Glu  Leu  Pro  Ile  Asp  Gly  Glu
               405                      410                      415

Asn  Ser  Leu  Val  Gly  Tyr  Ser  His  Arg  Leu  Ser  His  Val  Thr  Leu  Thr
               420                      425                      430

Arg  Ser  Leu  Tyr  Asn  Thr  Asn  Ile  Thr  Ser  Leu  Pro  Thr  Phe  Val  Trp
               435                      440                      445

Thr  His  His  Ser  Ala  Thr  Asn  Thr  Asn  Thr  Ile  Asn  Pro  Asp  Ile  Ile
     450                      455                      460

Thr  Gln  Ile  Pro  Leu  Val  Lys  Gly  Phe  Arg  Val  Trp  Gly  Gly  Thr  Ser
465                 470                      475                           480

Val  Ile  Thr  Gly  Pro  Gly  Phe  Thr  Gly  Gly  Asp  Ile  Leu  Arg  Arg  Asn
                    485                      490                      495

Thr  Phe  Gly  Asp  Phe  Val  Ser  Leu  Gln  Val  Asn  Ile  Asn  Ser  Pro  Ile
               500                      505                      510

Thr  Gln  Arg  Tyr  Arg  Leu  Arg  Phe  Arg  Tyr  Ala  Ser  Ser  Arg  Asp  Ala
               515                      520                      525

Arg  Val  Ile  Val  Leu  Thr  Gly  Ala  Ala  Ser  Thr  Gly  Val  Gly  Gly  Gln
     530                      535                      540

Val  Ser  Val  Asn  Met  Pro  Leu  Gln  Lys  Thr  Met  Glu  Ile  Gly  Glu  Asn
545                      550                      555                      560

Leu  Thr  Ser  Arg  Thr  Phe  Arg  Tyr  Thr  Asp  Phe  Ser  Asn  Pro  Phe  Ser
               565                      570                      575

Phe  Arg  Ala  Asn  Pro  Asp  Ile  Ile  Gly  Ile  Ser  Glu  Gln  Pro  Leu  Phe
               580                      585                      590

Gly  Ala  Gly  Ser  Ile  Ser  Ser  Gly  Glu  Leu  Tyr  Ile  Asp  Lys  Ile  Glu
          595                      600                      605

Ile  Ile  Leu  Ala  Asp  Ala  Thr  Phe  Glu  Ala  Glu  Ser  Asp  Leu  Glu  Arg
     610                      615                      620

Ala  Gln  Lys  Ala  Val  Asn  Ala  Leu  Phe  Thr  Ser  Ser  Asn  Gln  Ile  Gly
625                      630                      635                      640

Leu  Lys  Thr  Asp  Val  Thr  Asp  Tyr  His  Ile  Asp  Gln  Val  Ser  Asn  Leu
               645                      650                      655

Val  Asp  Cys  Leu  Ser  Asp  Glu  Phe  Cys  Leu  Asp  Glu  Lys  Arg  Glu  Leu
          660                      665                      670

Ser  Glu  Lys  Val  Lys  His  Ala  Lys  Arg  Leu  Ser  Asp  Glu  Arg  Asn  Leu
          675                      680                      685

Leu  Gln  Asp  Pro  Asn  Phe  Arg  Gly  Ile  Asn  Arg  Gln  Pro  Asp  Arg  Gly
     690                      695                      700

Trp  Arg  Gly  Ser  Thr  Asp  Ile  Thr  Ile  Gln  Gly  Gly  Asp  Asp  Val  Phe
705                 710                      715                           720

Lys  Glu  Asn  Tyr  Val  Thr  Leu  Pro  Gly  Thr  Val  Asp  Glu  Cys  Tyr  Pro
               725                      730                      735

Thr  Tyr  Leu  Tyr  Gln  Lys  Ile  Asp  Glu  Ser  Lys  Leu  Lys  Ala  Tyr  Thr
               740                      745                      750

Arg  Tyr  Glu  Leu  Arg  Gly  Tyr  Ile  Glu  Asp  Ser  Gln  Asp  Leu  Glu  Ile
          755                      760                      765

Tyr  Leu  Ile  Arg  Tyr  Asn  Ala  Lys  His  Glu  Ile  Val  Asn  Val  Pro  Gly
     770                      775                      780

Thr  Gly  Ser  Leu  Trp  Pro  Leu  Ser  Ala  Gln  Ser  Pro  Ile  Gly  Lys  Cys
785                      790                      795                      800

Gly  Glu  Pro  Asn  Arg  Cys  Ala  Pro  His  Leu  Glu  Trp  Asn  Pro  Asp  Leu
               805                      810                      815

Asp  Cys  Ser  Cys  Arg  Asp  Gly  Glu  Lys  Cys  Ala  His  His  Ser  His  His
```

```
                              820                          825                            830
Phe  Thr  Leu  Asp  Ile  Asp  Val  Gly  Cys  Thr  Asp  Leu  Asn  Glu  Asp  Leu
               835                          840                     845
Gly  Val  Trp  Val  Ile  Phe  Lys  Ile  Lys  Thr  Gln  Asp  Gly  His  Ala  Arg
     850                          855                     860
Leu  Gly  Asn  Leu  Glu  Phe  Leu  Glu  Glu  Lys  Pro  Leu  Leu  Gly  Glu  Ala
865                      870                     875                          880
Leu  Ala  Arg  Val  Lys  Arg  Ala  Glu  Lys  Lys  Trp  Arg  Asp  Lys  Arg  Glu
                    885                     890                     895
Lys  Leu  Gln  Leu  Glu  Thr  Asn  Ile  Val  Tyr  Lys  Glu  Ala  Lys  Glu  Ser
               900                     905                     910
Val  Asp  Ala  Leu  Phe  Val  Asn  Ser  Gln  Tyr  Asp  Arg  Leu  Gln  Val  Asp
               915                     920                     925
Thr  Asn  Ile  Ala  Met  Ile  His  Ala  Ala  Asp  Lys  Arg  Val  His  Arg  Ile
          930                     935                     940
Arg  Glu  Ala  Tyr  Leu  Pro  Glu  Leu  Ser  Val  Ile  Pro  Gly  Val  Asn  Ala
945                          950                     955                     960
Ala  Ile  Phe  Glu  Glu  Leu  Glu  Gly  Arg  Ile  Phe  Thr  Ala  Tyr  Ser  Leu
                    965                     970                     975
Tyr  Asp  Ala  Arg  Asn  Val  Ile  Lys  Asn  Gly  Asp  Phe  Asn  Asn  Gly  Leu
               980                     985                     990
Leu  Cys  Trp  Asn  Val  Lys  Gly  His  Val  Asp  Val  Glu  Glu  Gln  Asn  Asn
          995                     1000                    1005
His  Arg  Ser  Val  Leu  Val  Ile  Pro  Glu  Trp  Glu  Ala  Glu  Val  Ser  Gln
     1010                         1015                    1020
Glu  Val  Arg  Val  Cys  Pro  Gly  Arg  Gly  Tyr  Ile  Leu  Arg  Val  Thr  Ala
1025                         1030                    1035                    1040
Tyr  Lys  Glu  Gly  Tyr  Gly  Glu  Gly  Cys  Val  Thr  Ile  His  Glu  Ile  Glu
                    1045                         1050                    1055
Asp  Asn  Thr  Asp  Glu  Leu  Lys  Phe  Ser  Asn  Cys  Val  Glu  Glu  Glu  Val
               1060                         1065                    1070
Tyr  Pro  Asn  Asn  Thr  Val  Thr  Cys  Asn  Asn  Tyr  Thr  Gly  Thr  Gln  Glu
               1075                    1080                    1085
Glu  Tyr  Glu  Gly  Thr  Tyr  Thr  Ser  Arg  Asn  Gln  Gly  Tyr  Asp  Glu  Ala
          1090                    1095                    1100
Tyr  Gly  Asn  Asn  Pro  Ser  Val  Pro  Ala  Asp  Tyr  Ala  Ser  Val  Tyr  Glu
1105                     1110                    1115                         1120
Glu  Lys  Ser  Tyr  Thr  Asp  Gly  Arg  Arg  Glu  Asn  Pro  Cys  Glu  Ser  Asn
               1125                    1130                    1135
Arg  Gly  Tyr  Gly  Asp  Tyr  Thr  Pro  Leu  Pro  Ala  Gly  Tyr  Val  Thr  Lys
                    1140                    1145                    1150
Asp  Leu  Glu  Tyr  Phe  Pro  Glu  Thr  Asp  Lys  Val  Trp  Ile  Glu  Ile  Gly
               1155                    1160                    1165
Glu  Thr  Glu  Gly  Thr  Phe  Ile  Val  Asp  Ser  Val  Glu  Leu  Leu  Leu  Met
          1170                    1175                    1180
Glu  Glu
1185
```

( 2 ) INFORMATION FOR SEQ ID NO: 7:

( i ) SEQUENCE CHARACTERISTICS:
        ( A ) LENGTH: 3579 base pairs
        ( B ) TYPE: nucleic acid
        ( C ) STRANDEDNESS: single
        ( D ) TOPOLOGY: unknown ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: Hybrid toxin ( i x ) FEATURE:
    ( A ) NAME/KEY: CDS
    ( B ) LOCATION: 1..3579

( x i ) SEQUENCE DESCRIPTION: SEQ ID NO: 7:

| | | | | | | | | | | | | | | | | |
|---|---|---|---|---|---|---|---|---|---|---|---|---|---|---|---|---|
| ATG | GAT | AAC | AAT | CCG | AAC | ATC | AAT | GAA | TGC | ATT | CCT | TAT | AAT | TGT | TTA | 48 |
| Met | Asp | Asn | Asn | Pro | Asn | Ile | Asn | Glu | Cys | Ile | Pro | Tyr | Asn | Cys | Leu | |
| 1 | | | | 5 | | | | | 10 | | | | | | 15 | |
| AGT | AAC | CCT | GAA | GTA | GAA | GTA | TTA | GGT | GGA | GAA | AGA | ATA | GAA | ACT | GGT | 96 |
| Ser | Asn | Pro | Glu | Val | Glu | Val | Leu | Gly | Gly | Glu | Arg | Ile | Glu | Thr | Gly | |
| | | | 20 | | | | | 25 | | | | | 30 | | | |
| TAC | ACC | CCA | ATC | GAT | ATT | TCC | TTG | TCG | CTA | ACG | CAA | TTT | CTT | TTG | AGT | 144 |
| Tyr | Thr | Pro | Ile | Asp | Ile | Ser | Leu | Ser | Leu | Thr | Gln | Phe | Leu | Leu | Ser | |
| | | 35 | | | | | 40 | | | | | 45 | | | | |
| GAA | TTT | GTT | CCC | GGT | GCT | GGA | TTT | GTG | TTA | GGA | CTA | GTT | GAT | ATA | ATA | 192 |
| Glu | Phe | Val | Pro | Gly | Ala | Gly | Phe | Val | Leu | Gly | Leu | Val | Asp | Ile | Ile | |
| | | 50 | | | | | 55 | | | | | 60 | | | | |
| TGG | GGA | ATT | TTT | GGT | CCC | TCT | CAA | TGG | GAC | GCA | TTT | CTT | GTA | CAA | ATT | 240 |
| Trp | Gly | Ile | Phe | Gly | Pro | Ser | Gln | Trp | Asp | Ala | Phe | Leu | Val | Gln | Ile | |
| 65 | | | | | 70 | | | | | 75 | | | | | 80 | |
| GAA | CAG | TTA | ATT | AAC | CAA | AGA | ATA | GAA | GAA | TTC | GCT | AGG | AAC | CAA | GCC | 288 |
| Glu | Gln | Leu | Ile | Asn | Gln | Arg | Ile | Glu | Glu | Phe | Ala | Arg | Asn | Gln | Ala | |
| | | | | 85 | | | | | 90 | | | | | 95 | | |
| ATT | TCT | AGA | TTA | GAA | GGA | CTA | AGC | AAT | CTT | TAT | CAA | ATT | TAC | GCA | GAA | 336 |
| Ile | Ser | Arg | Leu | Glu | Gly | Leu | Ser | Asn | Leu | Tyr | Gln | Ile | Tyr | Ala | Glu | |
| | | | 100 | | | | | 105 | | | | | 110 | | | |
| TCT | TTT | AGA | GAG | TGG | GAA | GCA | GAT | CCT | ACT | AAT | CCA | GCA | TTA | AGA | GAA | 384 |
| Ser | Phe | Arg | Glu | Trp | Glu | Ala | Asp | Pro | Thr | Asn | Pro | Ala | Leu | Arg | Glu | |
| | | 115 | | | | | 120 | | | | | 125 | | | | |
| GAG | ATG | CGT | ATT | CAA | TTC | AAT | GAC | ATG | AAC | AGT | GCC | CTT | ACA | ACC | GCT | 432 |
| Glu | Met | Arg | Ile | Gln | Phe | Asn | Asp | Met | Asn | Ser | Ala | Leu | Thr | Thr | Ala | |
| | 130 | | | | | 135 | | | | | 140 | | | | | |
| ATT | CCT | CTT | TTT | GCA | GTT | CAA | AAT | TAT | CAA | GTT | CCT | CTT | TTA | TCA | GTA | 480 |
| Ile | Pro | Leu | Phe | Ala | Val | Gln | Asn | Tyr | Gln | Val | Pro | Leu | Leu | Ser | Val | |
| 145 | | | | | 150 | | | | | 155 | | | | | 160 | |
| TAT | GTT | CAA | GCT | GCA | AAT | TTA | CAT | TTA | TCA | GTT | TTG | AGA | GAT | GTT | TCA | 528 |
| Tyr | Val | Gln | Ala | Ala | Asn | Leu | His | Leu | Ser | Val | Leu | Arg | Asp | Val | Ser | |
| | | | | 165 | | | | | 170 | | | | | 175 | | |
| GTG | TTT | GGA | CAA | AGG | TGG | GGA | TTT | GAT | GCC | GCG | ACT | ATC | AAT | AGT | CGT | 576 |
| Val | Phe | Gly | Gln | Arg | Trp | Gly | Phe | Asp | Ala | Ala | Thr | Ile | Asn | Ser | Arg | |
| | | | 180 | | | | | 185 | | | | | 190 | | | |
| TAT | AAT | GAT | TTA | ACT | AGG | CTT | ATT | GGC | AAC | TAT | ACA | GAT | CAT | GCT | GTA | 624 |
| Tyr | Asn | Asp | Leu | Thr | Arg | Leu | Ile | Gly | Asn | Tyr | Thr | Asp | His | Ala | Val | |
| | | 195 | | | | | 200 | | | | | 205 | | | | |
| CGC | TGG | TAC | AAT | ACG | GGA | TTA | GAG | CGT | GTA | TGG | GGA | CCG | GAT | TCT | AGA | 672 |
| Arg | Trp | Tyr | Asn | Thr | Gly | Leu | Glu | Arg | Val | Trp | Gly | Pro | Asp | Ser | Arg | |
| | 210 | | | | | 215 | | | | | 220 | | | | | |
| GAT | TGG | ATA | AGA | TAT | AAT | CAA | TTT | AGA | AGA | GAA | TTA | ACA | CTA | ACT | GTA | 720 |
| Asp | Trp | Ile | Arg | Tyr | Asn | Gln | Phe | Arg | Arg | Glu | Leu | Thr | Leu | Thr | Val | |
| 225 | | | | | 230 | | | | | 235 | | | | | 240 | |
| TTA | GAT | ATC | GTT | TCT | CTA | TTT | CCG | AAC | TAT | GAT | AGT | AGA | ACG | TAT | CCA | 768 |
| Leu | Asp | Ile | Val | Ser | Leu | Phe | Pro | Asn | Tyr | Asp | Ser | Arg | Thr | Tyr | Pro | |
| | | | | 245 | | | | | 250 | | | | | 255 | | |
| ATT | CGA | ACA | GTT | TCC | CAA | TTA | ACA | AGA | GAA | ATT | TAT | ACA | AAC | CCA | GTA | 816 |

```
Ile Arg Thr Val Ser Gln Leu Thr Arg Glu Ile Tyr Thr Asn Pro Val
        260                 265                 270

TTA GAA AAT TTT GAT GGT AGT TTT CGA GGC TCG GCT CAG GGC ATA GAA     864
Leu Glu Asn Phe Asp Gly Ser Phe Arg Gly Ser Ala Gln Gly Ile Glu
        275                 280                 285

GGA AGT ATT AGG AGT CCA CAT TTG ATG GAT ATA CTT AAC AGT ATA ACC     912
Gly Ser Ile Arg Ser Pro His Leu Met Asp Ile Leu Asn Ser Ile Thr
        290                 295                 300

ATC TAT ACG GAT GCT CAT AGA GGA GAA TAT TAT TGG TCA GGG CAT CAA     960
Ile Tyr Thr Asp Ala His Arg Gly Glu Tyr Tyr Trp Ser Gly His Gln
305                 310                 315                 320

ATA ATG GCT TCT CCT GTA GGG TTT TCG GGG CCA GAA TTC ACT TTT CCG    1008
Ile Met Ala Ser Pro Val Gly Phe Ser Gly Pro Glu Phe Thr Phe Pro
                325                 330                 335

CTA TAT GGA ACT ATG GGA AAT GCA GCT CCA CAA CAA CGT ATT GTT GCT    1056
Leu Tyr Gly Thr Met Gly Asn Ala Ala Pro Gln Gln Arg Ile Val Ala
            340                 345                 350

CAA CTA GGT CAG GGC GTG TAT AGA ACA TTA TCG TCC ACT TTA TAT AGA    1104
Gln Leu Gly Gln Gly Val Tyr Arg Thr Leu Ser Ser Thr Leu Tyr Arg
        355                 360                 365

AGA CCT TTT AAT ATA GGG ATA AAT AAT CAA CAA CTA TCT GTT CTT GAC    1152
Arg Pro Phe Asn Ile Gly Ile Asn Asn Gln Gln Leu Ser Val Leu Asp
    370                 375                 380

GGG ACA GAA TTT GCT TAT GGA ACC TCC TCA AAT TTG CCA TCC GCT GTA    1200
Gly Thr Glu Phe Ala Tyr Gly Thr Ser Ser Asn Leu Pro Ser Ala Val
385                 390                 395                 400

TAC AGA AAA AGC GGA ACG GTA GAT TCG CTG GAT GAA ATA CCG CCA CAG    1248
Tyr Arg Lys Ser Gly Thr Val Asp Ser Leu Asp Glu Ile Pro Pro Gln
                405                 410                 415

AAT AAC AAC GTG CCA CCT AGG CAA GGA TTT AGT CAT CGA TTA AGC CAT    1296
Asn Asn Asn Val Pro Pro Arg Gln Gly Phe Ser His Arg Leu Ser His
            420                 425                 430

GTT TCA ATG TTT CGT TCA GGC TTT AGT AAT AGT AGT GTA AGT ATA ATA    1344
Val Ser Met Phe Arg Ser Gly Phe Ser Asn Ser Ser Val Ser Ile Ile
        435                 440                 445

AGA GCT CCT ATG TTC TCT TGG ATA CAT CGT AGT GCA ACT CTT ACA AAT    1392
Arg Ala Pro Met Phe Ser Trp Ile His Arg Ser Ala Thr Leu Thr Asn
    450                 455                 460

ACA ATT GAT CCA GAG AGA ATT AAT CAA ATA CCT TTA GTG AAA GGA TTT    1440
Thr Ile Asp Pro Glu Arg Ile Asn Gln Ile Pro Leu Val Lys Gly Phe
465                 470                 475                 480

AGA GTT TGG GGG GGC ACC TCT GTC ATT ACA GGA CCA GGA TTT ACA GGA    1488
Arg Val Trp Gly Gly Thr Ser Val Ile Thr Gly Pro Gly Phe Thr Gly
                485                 490                 495

GGG GAT ATC CTT CGA AGA AAT ACC TTT GGT GAT TTT GTA TCT CTA CAA    1536
Gly Asp Ile Leu Arg Arg Asn Thr Phe Gly Asp Phe Val Ser Leu Gln
            500                 505                 510

GTC AAT ATT AAT TCA CCA ATT ACC CAA AGA TAC CGT TTA AGA TTT CGT    1584
Val Asn Ile Asn Ser Pro Ile Thr Gln Arg Tyr Arg Leu Arg Phe Arg
        515                 520                 525

TAC GCT TCC AGT AGG GAT GCA CGA GTT ATA GTA TTA ACA GGA GCG GCA    1632
Tyr Ala Ser Ser Arg Asp Ala Arg Val Ile Val Leu Thr Gly Ala Ala
    530                 535                 540

TCC ACA GGA GTG GGA GGC CAA GTT AGT GTA AAT ATG CCT CTT CAG AAA    1680
Ser Thr Gly Val Gly Gly Gln Val Ser Val Asn Met Pro Leu Gln Lys
545                 550                 555                 560

ACT ATG GAA ATA GGG GAG AAC TTA ACA TCT AGA ACA TTT AGA TAT ACC    1728
Thr Met Glu Ile Gly Glu Asn Leu Thr Ser Arg Thr Phe Arg Tyr Thr
                565                 570                 575

GAT TTT AGT AAT CCT TTT TCA TTT AGA GCT AAT CCA GAT ATA ATT GGG    1776
```

```
Asp Phe Ser Asn Pro Phe Ser Phe Arg Ala Asn Pro Asp Ile Ile Gly
            580             585             590

ATA AGT GAA CAA CCT CTA TTT GGT GCA GGT TCT ATT AGT AGC GGT GAA      1824
Ile Ser Glu Gln Pro Leu Phe Gly Ala Gly Ser Ile Ser Ser Gly Glu
        595             600             605

CTT TAT ATA GAT AAA ATT GAA ATT ATT CTA GCA GAT GCA ACA TTT GAA      1872
Leu Tyr Ile Asp Lys Ile Glu Ile Ile Leu Ala Asp Ala Thr Phe Glu
        610             615             620

GCA GAA TCT GAT TTA GAA AGA GCA CAA AAG GCG GTG AAT GCC CTG TTT      1920
Ala Glu Ser Asp Leu Glu Arg Ala Gln Lys Ala Val Asn Ala Leu Phe
625             630             635             640

ACT TCT TCC AAT CAA ATC GGG TTA AAA ACC GAT GTG ACG GAT TAT CAT      1968
Thr Ser Ser Asn Gln Ile Gly Leu Lys Thr Asp Val Thr Asp Tyr His
        645             650             655

ATT GAT CAA GTA TCC AAT TTA GTG GAT TGT TTA TCA GAT GAA TTT TGT      2016
Ile Asp Gln Val Ser Asn Leu Val Asp Cys Leu Ser Asp Glu Phe Cys
        660             665             670

CTG GAT GAA AAG CGA GAA TTG TCC GAG AAA GTC AAA CAT GCG AAG CGA      2064
Leu Asp Glu Lys Arg Glu Leu Ser Glu Lys Val Lys His Ala Lys Arg
        675             680             685

CTC AGT GAT GAG CGG AAT TTA CTT CAA GAT CCA AAC TTC AGA GGG ATC      2112
Leu Ser Asp Glu Arg Asn Leu Leu Gln Asp Pro Asn Phe Arg Gly Ile
        690             695             700

AAT AGA CAA CCA GAC CGT GGC TGG AGA GGA AGT ACA GAT ATT ACC ATC      2160
Asn Arg Gln Pro Asp Arg Gly Trp Arg Gly Ser Thr Asp Ile Thr Ile
705             710             715             720

CAA GGA GGA GAT GAC GTA TTC AAA GAG AAT TAC GTC ACA CTA CCG GGT      2208
Gln Gly Gly Asp Asp Val Phe Lys Glu Asn Tyr Val Thr Leu Pro Gly
                725             730             735

ACC GTT GAT GAG TGC TAT CCA ACG TAT TTA TAT CAG AAA ATA GAT GAG      2256
Thr Val Asp Glu Cys Tyr Pro Thr Tyr Leu Tyr Gln Lys Ile Asp Glu
            740             745             750

TCG AAA TTA AAA GCT TAT ACC CGT TAT GAA TTA AGA GGG TAT ATC GAA      2304
Ser Lys Leu Lys Ala Tyr Thr Arg Tyr Glu Leu Arg Gly Tyr Ile Glu
        755             760             765

GAT AGT CAA GAC TTA GAA ATC TAT TTG ATC CGT TAC AAT GCA AAA CAC      2352
Asp Ser Gln Asp Leu Glu Ile Tyr Leu Ile Arg Tyr Asn Ala Lys His
770             775             780

GAA ATA GTA AAT GTG CCA GGC ACG GGT TCC TTA TGG CCG CTT TCA GCC      2400
Glu Ile Val Asn Val Pro Gly Thr Gly Ser Leu Trp Pro Leu Ser Ala
785             790             795             800

CAA AGT CCA ATC GGA AAG TGT GGA GAA CCG AAT CGA TGC GCG CCA CAC      2448
Gln Ser Pro Ile Gly Lys Cys Gly Glu Pro Asn Arg Cys Ala Pro His
        805             810             815

CTT GAA TGG AAT CCT GAT CTA GAT TGT TCC TGC AGA GAC GGG GAA AAA      2496
Leu Glu Trp Asn Pro Asp Leu Asp Cys Ser Cys Arg Asp Gly Glu Lys
        820             825             830

TGT GCA CAT CAT TCC CAT CAT TTC ACC TTG GAT ATT GAT GTT GGA TGT      2544
Cys Ala His His Ser His His Phe Thr Leu Asp Ile Asp Val Gly Cys
        835             840             845

ACA GAC TTA AAT GAG GAC TTA GGT GTA TGG GTG ATA TTC AAG ATT AAG      2592
Thr Asp Leu Asn Glu Asp Leu Gly Val Trp Val Ile Phe Lys Ile Lys
850             855             860

ACG CAA GAT GGC CAT GCA AGA CTA GGG AAT CTA GAG TTT CTC GAA GAG      2640
Thr Gln Asp Gly His Ala Arg Leu Gly Asn Leu Glu Phe Leu Glu Glu
865             870             875             880

AAA CCA TTA TTA GGG GAA GCA CTA GCT CGT GTG AAA AGA GCG GAG AAG      2688
Lys Pro Leu Leu Gly Glu Ala Leu Ala Arg Val Lys Arg Ala Glu Lys
            885             890             895

AAG TGG AGA GAC AAA CGA GAG AAA CTG CAG TTG GAA ACA AAT ATT GTT      2736
```

```
Lys Trp Arg Asp Lys Arg Glu Lys Leu Gln Leu Glu Thr Asn Ile Val
            900             905                 910
TAT AAA GAG GCA AAA GAA TCT GTA GAT GCT TTA TTT GTA AAC TCT CAA    2784
Tyr Lys Glu Ala Lys Glu Ser Val Asp Ala Leu Phe Val Asn Ser Gln
        915             920                 925
TAT GAT AGA TTA CAA GTG GAT ACG AAC ATC GCG ATG ATT CAT GCG GCA    2832
Tyr Asp Arg Leu Gln Val Asp Thr Asn Ile Ala Met Ile His Ala Ala
        930             935                 940
GAT AAA CGC GTT CAT AGA ATC CGG GAA GCG TAT CTG CCA GAG TTG TCT    2880
Asp Lys Arg Val His Arg Ile Arg Glu Ala Tyr Leu Pro Glu Leu Ser
945             950                 955                 960
GTG ATT CCA GGT GTC AAT GCG GCC ATT TTC GAA GAA TTA GAG GGA CGT    2928
Val Ile Pro Gly Val Asn Ala Ala Ile Phe Glu Glu Leu Glu Gly Arg
                965                 970                 975
ATT TTT ACA GCG TAT TCC TTA TAT GAT GCG AGA AAT GTC ATT AAA AAT    2976
Ile Phe Thr Ala Tyr Ser Leu Tyr Asp Ala Arg Asn Val Ile Lys Asn
            980             985                 990
GGC GAT TTC AAT AAT GGC TTA TTA TGC TGG AAC GTG AAA GGT CAT GTA    3024
Gly Asp Phe Asn Asn Gly Leu Leu Cys Trp Asn Val Lys Gly His Val
        995                 1000                1005
GAT GTA GAA GAG CAA AAC AAC CAC CGT TCG GTC CTT GTT ATC CCA GAA    3072
Asp Val Glu Glu Gln Asn Asn His Arg Ser Val Leu Val Ile Pro Glu
1010                1015                1020
TGG GAG GCA GAA GTG TCA CAA GAG GTT CGT GTC TGT CCA GGT CGT GGC    3120
Trp Glu Ala Glu Val Ser Gln Glu Val Arg Val Cys Pro Gly Arg Gly
1025                1030                1035                1040
TAT ATC CTT CGT GTC ACA GCA TAT AAA GAG GGA TAT GGA GAG GGC TGC    3168
Tyr Ile Leu Arg Val Thr Ala Tyr Lys Glu Gly Tyr Gly Glu Gly Cys
            1045                1050                1055
GTA ACG ATC CAT GAG ATC GAA GAC AAT ACA GAC GAA CTG AAA TTC AGC    3216
Val Thr Ile His Glu Ile Glu Asp Asn Thr Asp Glu Leu Lys Phe Ser
        1060                1065                1070
AAC TGT GTA GAA GAG GAA GTA TAT CCA AAC AAC ACA GTA ACG TGT AAT    3264
Asn Cys Val Glu Glu Glu Val Tyr Pro Asn Asn Thr Val Thr Cys Asn
        1075                1080                1085
AAT TAT ACT GGG ACT CAA GAA GAA TAT GAG GGT ACG TAC ACT TCT CGT    3312
Asn Tyr Thr Gly Thr Gln Glu Glu Tyr Glu Gly Thr Tyr Thr Ser Arg
1090                1095                1100
AAT CAA GGA TAT GAC GAA GCC TAT GGT AAT AAC CCT TCC GTA CCA GCT    3360
Asn Gln Gly Tyr Asp Glu Ala Tyr Gly Asn Asn Pro Ser Val Pro Ala
1105                1110                1115                1120
GAT TAC GCT TCA GTC TAT GAA GAA AAA TCG TAT ACA GAT GGA CGA AGA    3408
Asp Tyr Ala Ser Val Tyr Glu Glu Lys Ser Tyr Thr Asp Gly Arg Arg
            1125                1130                1135
GAG AAT CCT TGT GAA TCT AAC AGA GGC TAT GGG GAT TAC ACA CCA CTA    3456
Glu Asn Pro Cys Glu Ser Asn Arg Gly Tyr Gly Asp Tyr Thr Pro Leu
        1140                1145                1150
CCG GCT GGT TAT GTA ACA AAG GAT TTA GAG TAC TTC CCA GAG ACC GAT    3504
Pro Ala Gly Tyr Val Thr Lys Asp Leu Glu Tyr Phe Pro Glu Thr Asp
        1155                1160                1165
AAG GTA TGG ATT GAG ATC GGA GAA ACA GAA GGA ACA TTC ATC GTG GAT    3552
Lys Val Trp Ile Glu Ile Gly Glu Thr Glu Gly Thr Phe Ile Val Asp
        1170                1175                1180
AGC GTG GAA TTA CTC CTT ATG GAG GAA                                3579
Ser Val Glu Leu Leu Leu Met Glu Glu
1185                1190
```

( 2 ) INFORMATION FOR SEQ ID NO: 8:

( i ) SEQUENCE CHARACTERISTICS:

( A ) LENGTH: 1193 amino acids ( B ) TYPE: amino acid
( D ) TOPOLOGY: linear ( i i ) MOLECULE TYPE: protein ( x i ) SEQUENCE DESCRIPTION: SEQ ID NO: 8:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
               20                  25                  30

Tyr Thr Pro Ile Asp Ile Ser Leu Ser Leu Thr Gln Phe Leu Leu Ser
           35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65              70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
             100                 105                 110

Ser Phe Arg Glu Trp Glu Ala Asp Pro Thr Asn Pro Ala Leu Arg Glu
         115                 120                 125

Glu Met Arg Ile Gln Phe Asn Asp Met Asn Ser Ala Leu Thr Thr Ala
     130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                 165                 170                 175

Val Phe Gly Gln Arg Trp Gly Phe Asp Ala Ala Thr Ile Asn Ser Arg
             180                 185                 190

Tyr Asn Asp Leu Thr Arg Leu Ile Gly Asn Tyr Thr Asp His Ala Val
         195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
```

-continued

```
385                         390                         395                         400
Tyr  Arg  Lys  Ser  Gly  Thr  Val  Asp  Ser  Leu  Asp  Glu  Ile  Pro  Pro  Gln
                         405                      410                      415

Asn  Asn  Asn  Val  Pro  Pro  Arg  Gln  Gly  Phe  Ser  His  Arg  Leu  Ser  His
               420                      425                           430

Val  Ser  Met  Phe  Arg  Ser  Gly  Phe  Ser  Asn  Ser  Ser  Val  Ser  Ile  Ile
          435                      440                     445

Arg  Ala  Pro  Met  Phe  Ser  Trp  Ile  His  Arg  Ser  Ala  Thr  Leu  Thr  Asn
     450                      455                     460

Thr  Ile  Asp  Pro  Glu  Arg  Ile  Asn  Gln  Ile  Pro  Leu  Val  Lys  Gly  Phe
465                      470                      475                         480

Arg  Val  Trp  Gly  Gly  Thr  Ser  Val  Ile  Thr  Gly  Pro  Gly  Phe  Thr  Gly
                    485                      490                         495

Gly  Asp  Ile  Leu  Arg  Arg  Asn  Thr  Phe  Gly  Asp  Phe  Val  Ser  Leu  Gln
               500                      505                          510

Val  Asn  Ile  Asn  Ser  Pro  Ile  Thr  Gln  Arg  Tyr  Arg  Leu  Arg  Phe  Arg
          515                      520                          525

Tyr  Ala  Ser  Ser  Arg  Asp  Ala  Arg  Val  Ile  Val  Leu  Thr  Gly  Ala  Ala
     530                      535                          540

Ser  Thr  Gly  Val  Gly  Gly  Gln  Val  Ser  Val  Asn  Met  Pro  Leu  Gln  Lys
545                      550                       555                          560

Thr  Met  Glu  Ile  Gly  Glu  Asn  Leu  Thr  Ser  Arg  Thr  Phe  Arg  Tyr  Thr
                    565                      570                          575

Asp  Phe  Ser  Asn  Pro  Phe  Ser  Phe  Arg  Ala  Asn  Pro  Asp  Ile  Ile  Gly
               580                      585                          590

Ile  Ser  Glu  Gln  Pro  Leu  Phe  Gly  Ala  Gly  Ser  Ile  Ser  Ser  Gly  Glu
          595                      600                          605

Leu  Tyr  Ile  Asp  Lys  Ile  Glu  Ile  Ile  Leu  Ala  Asp  Ala  Thr  Phe  Glu
     610                      615                          620

Ala  Glu  Ser  Asp  Leu  Glu  Arg  Ala  Gln  Lys  Ala  Val  Asn  Ala  Leu  Phe
625                      630                       635                          640

Thr  Ser  Ser  Asn  Gln  Ile  Gly  Leu  Lys  Thr  Asp  Val  Thr  Asp  Tyr  His
               645                      650                          655

Ile  Asp  Gln  Val  Ser  Asn  Leu  Val  Asp  Cys  Leu  Ser  Asp  Glu  Phe  Cys
          660                      665                          670

Leu  Asp  Glu  Lys  Arg  Glu  Leu  Ser  Glu  Lys  Val  Lys  His  Ala  Lys  Arg
          675                      680                          685

Leu  Ser  Asp  Glu  Arg  Asn  Leu  Leu  Gln  Asp  Pro  Asn  Phe  Arg  Gly  Ile
     690                      695                          700

Asn  Arg  Gln  Pro  Asp  Arg  Gly  Trp  Arg  Gly  Ser  Thr  Asp  Ile  Thr  Ile
705                      710                       715                          720

Gln  Gly  Gly  Asp  Asp  Val  Phe  Lys  Glu  Asn  Tyr  Val  Thr  Leu  Pro  Gly
               725                      730                          735

Thr  Val  Asp  Glu  Cys  Tyr  Pro  Thr  Tyr  Leu  Tyr  Gln  Lys  Ile  Asp  Glu
          740                      745                          750

Ser  Lys  Leu  Lys  Ala  Tyr  Thr  Arg  Tyr  Glu  Leu  Arg  Gly  Tyr  Ile  Glu
          755                      760                          765

Asp  Ser  Gln  Asp  Leu  Glu  Ile  Tyr  Leu  Ile  Arg  Tyr  Asn  Ala  Lys  His
     770                      775                          780

Glu  Ile  Val  Asn  Val  Pro  Gly  Thr  Gly  Ser  Leu  Trp  Pro  Leu  Ser  Ala
785                      790                       795                          800

Gln  Ser  Pro  Ile  Gly  Lys  Cys  Gly  Glu  Pro  Asn  Arg  Cys  Ala  Pro  His
                    805                      810                          815
```

| | | | | | | | | | | | | | |
|---|---|---|---|---|---|---|---|---|---|---|---|---|---|
|Leu|Glu|Trp|Asn 820|Pro|Asp|Leu|Asp|Cys 825|Ser|Cys|Arg|Asp|Gly 830|Glu|Lys|
|Cys|Ala|His 835|His|Ser|His|His|Phe 840|Thr|Leu|Asp|Ile|Asp 845|Val|Gly|Cys|
|Thr|Asp 850|Leu|Asn|Glu|Asp|Leu 855|Gly|Val|Trp|Val|Ile 860|Phe|Lys|Ile|Lys|
|Thr 865|Gln|Asp|Gly|His|Ala 870|Arg|Leu|Gly|Asn|Leu 875|Glu|Phe|Leu|Glu|Glu 880|
|Lys|Pro|Leu|Leu|Gly 885|Glu|Ala|Leu|Ala|Arg 890|Val|Lys|Arg|Ala|Glu 895|Lys|
|Lys|Trp|Arg|Asp 900|Lys|Arg|Glu|Lys|Leu 905|Gln|Leu|Glu|Thr|Asn 910|Ile|Val|
|Tyr|Lys|Glu 915|Ala|Lys|Glu|Ser|Val 920|Asp|Ala|Leu|Phe|Val 925|Asn|Ser|Gln|
|Tyr|Asp 930|Arg|Leu|Gln|Val|Asp 935|Thr|Asn|Ile|Ala|Met 940|Ile|His|Ala|Ala|
|Asp 945|Lys|Arg|Val|His|Arg 950|Ile|Arg|Glu|Ala|Tyr 955|Leu|Pro|Glu|Leu|Ser 960|
|Val|Ile|Pro|Gly|Val 965|Asn|Ala|Ala|Ile|Phe 970|Glu|Glu|Leu|Glu|Gly 975|Arg|
|Ile|Phe|Thr|Ala 980|Tyr|Ser|Leu|Tyr|Asp 985|Ala|Arg|Asn|Val|Ile 990|Lys|Asn|
|Gly|Asp|Phe 995|Asn|Asn|Gly|Leu|Leu 1000|Cys|Trp|Asn|Val|Lys 1005|Gly|His|Val|
|Asp|Val|Glu 1010|Glu|Gln|Asn|Asn|His 1015|Arg|Ser|Val|Leu|Val 1020|Ile|Pro|Glu|
|Trp|Glu 1025|Ala|Glu|Val|Ser|Gln 1030|Glu|Val|Arg|Val|Cys 1035|Pro|Gly|Arg|Gly 1040|
|Tyr|Ile|Leu|Arg|Val 1045|Thr|Ala|Tyr|Lys|Glu 1050|Gly|Tyr|Gly|Glu|Gly 1055|Cys|
|Val|Thr|Ile|His 1060|Glu|Ile|Glu|Asp|Asn 1065|Thr|Asp|Glu|Leu|Lys 1070|Phe|Ser|
|Asn|Cys|Val 1075|Glu|Glu|Glu|Val|Tyr 1080|Pro|Asn|Asn|Thr|Val 1085|Thr|Cys|Asn|
|Asn|Tyr|Thr 1090|Gly|Thr|Gln|Glu|Glu 1095|Tyr|Glu|Gly|Thr|Tyr 1100|Thr|Ser|Arg|
|Asn 1105|Gln|Gly|Tyr|Asp|Glu 1110|Ala|Tyr|Gly|Asn|Asn 1115|Pro|Ser|Val|Pro|Ala 1120|
|Asp|Tyr|Ala|Ser|Val 1125|Tyr|Glu|Glu|Lys|Ser 1130|Tyr|Thr|Asp|Gly|Arg 1135|Arg|
|Glu|Asn|Pro|Cys 1140|Glu|Ser|Asn|Arg|Gly 1145|Tyr|Gly|Asp|Tyr|Thr 1150|Pro|Leu|
|Pro|Ala|Gly|Tyr 1155|Val|Thr|Lys|Asp|Leu 1160|Glu|Tyr|Phe|Pro|Glu 1165|Thr|Asp|
|Lys|Val|Trp 1170|Ile|Glu|Ile|Gly|Glu 1175|Thr|Glu|Gly|Thr|Phe 1180|Ile|Val|Asp|
|Ser 1185|Val|Glu|Leu|Leu|Leu 1190|Met|Glu|Glu| | | | | | | |

HYBRID TOXIN

The present invention relates to hybrid toxin figments, and toxins comprising them, derived from *Bacillus thuringiensis* insecticidal crystal proteins.

*Bacillus thuringiensis* (hereinafter *B.t.*) is capable of producing proteins that accumulate intracellularly as crystals. These crystal proteins are toxic to a number of insect larvae. Based on sequence homology and insecticidal specificity, crystal proteins have been categorized into different classes. Best studied are the CryI class of proteins which are produced as 140 kDa pro-toxins and are active towards lepidopterans.

To some extent the mode of action of crystal proteins has been elucidated. After oral uptake the crystals dissolve in the alkaline environment of the larval midgut. The solubilized proteins are subsequently processed by midgut proteinases to a proteinase-resistant toxic fragment of about 65 kDa which binds to receptors on epithelial cells of the insect midgut and penetrates the cell membrane. This eventually leads to bursting of the cells and death of the larvae.

The activity spectrum of a particular crystal protein is to a large extent determined by the occurrence of receptors on the midgut epithelial cells of susceptible insects. The said spectrum is co-determined by the efficiency of solubilization of the crystal protein and its proteolytic activation in vivo. The importance of the binding of the crystal protein to midgut epithelial receptors is further demonstrated where insects have developed resistance to one of the crystal proteins in that the binding of crystal proteins to midgut epithelial cells in resistant insects is significantly reduced.

Toxic fragments of crystal proteins are thought to be composed of three distinct structural domains. Domain I, the most N-terminal domain, consists of 7 α-helices. Domain II comprises 3 β-sheets and domain III (the most C-terminal) folds into a β-sandwich. If projected on CryI sequences, domain I runs from about amino acid residue 28 to 260; domain II from about 260 to 460 and domain III from about 460 to 600.

The present invention concerns hybrid crystal proteins particularly, though not exclusively, involving CryIC and CryIE or CryIA. The nucleotide sequence of the CryIC gene from *B.t.* sub.sp. *entomocidus* 60.5 is given in SEQ ID. No. 1, and the corresponding amino acid sequence of the protein encoded by the said nucleotide sequence is given in SEQ ID No. 2. The nucleotide sequence of the CryIE gene from *B.t.* sub. sp. *kenyae* 4FI is given in SEQ ID. No. 3, and the corresponding amino acid sequence of the protein encoded by the said nucleotide sequence is given in SEQ ID No. 4. These proteins are toxic to lepidopterans, but within this order of insects, each protein has different specificity. CryIC is particularly active against *S. exigua* and *M. brassicae*.

According to the present invention there is provided a *B.t.* hybrid toxin fragment comprising at its C-terminal domain III of a first Cry protein or a part of the domain or a protein substantially similar to the domain, with the proviso that the N-terminal region of the fragment is the N-terminal region of a second Cry protein or a part of the region or a protein substantially similar to the region. A preferred fragment is one which does not bind to the CryIC binding site in an insect gut when it comprises at its C-terminal domain III of CryIC or a part of the domain or a protein substantially similar to the domain; or one which does not bind to a CryIA binding site when it comprises at its C-terminal domain III of CryIA or a part of the domain or a protein substantially similar to the domain.

By substantially similar is meant pure proteins having an amino acid sequence which is at least 75% similar to the sequence of the proteins according to the invention. It is preferred that the degree of similarity is at least 85%, more preferred that the degree of similarity is at least 90% and still more preferred that the degree of similarity is at least 95%.

In the context of the present invention, two amino acid sequences with at least 75%, 85%, 90% or 95% similarity to each other have at least 75%, 85%, 90%, or 95% identical or conservatively replaced amino acid residues in a like position when aligned optimally allowing for up to 6 gaps with the proviso that in respect of the gaps a total not more than 15 amino acid residues are affected. For the purpose of the present invention conservative replacements may be made between amino acids within the following groups:

(i) Serine, and Threonine;
(ii) Glutamic acid and Aspartic acid;
(iii) Arginine and Lysine;
(iv) Asparagine and Glutamine;
(v) Isoleucine, Leucine, Valine and Methionine;
(vi) Phenylalanine, Tyrosine and Tryptophan
(vii) Alanine and Glycine with the proviso that in SEQ ID No. 6 Ser and Tyr are conservative replacements at position 620, and Ala and Glu are conservative replacements at position 618; and that in SEQ ID No. 8 Ser and Tyr are conservative replacements at position 627, and Ala and Glu are conservative replacements at position 625.

By "part" of a protein is meant a peptide comprised by the said protein and having at least 80% of the consecutive sequence thereof.

By "binding site" is meant a site on a molecule wherein the binding between site and toxin is reversible such that the Ka between site and toxin is in the order of at least $10^4 dm^3 mole^{-1}$.

The toxin fragment may comprise at its N-terminal the N-terminal region of any insecticidal proteins from *B.t.* being commonly known as "Cry" or "Cyt", including: CryIA(a), CryIA(b) CryIA(c), CryIB, CryIC, CryID, CryIE, CryIF, CryIG, CryIH, CryIIA, CryIIB, CryIIC, CryIIIA, CryIIIB, CryIIIB(b), CryIVA, CryIVB, CryIVC, CryIVD, CYTA, CryX1(IIIC), CryX2(IIID), CryX3, CryV, and CryX4; or a part of the region, or a protein substantially similar to the region, and that the C-terminal of the fragment is domain III of CryIC or a part of the domain or a protein substantially similar to the domain.

Thus the fragment may comprise domain II of CryIE, CryIB, CryID or CryIA, or a part of the domain or a protein substantially similar to the domain, and domain III of CryIC or a part of the said domain III or a protein substantially similar to the said domain III. It is particularly preferred that the fragment comprises domains I and II of CryIE, CryIB, CryID or CryIA or a part thereof or a protein substantially similar to the said domains, and domain III of CryIC or a part thereof or a protein substantially similar to the said domain III.

It is most preferred that the toxin fragment comprises a region at its C-terminus comprising the sequence from amino acid position 454 to position 602 of CryIC, or a sequence substantially similar to the said sequence. The fragment may comprise a region at its C-terminus comprising the sequence from amino acid position 478 to 602 of Cry IC, or a sequence substantially similar to the said sequence, with the proviso that if the sequence comprising amino acids 478 to 602 of CryIC is fused directly to the C-terminus of domain II of CryIA, CryIB, CryID or CryIE then the folding of the fusion product is satisfactory to yield an insecticidal component of the fragment. The skilled man will recognize that it may be necessary to add a peptide region to the C-terminus of domain II which spaces the C-terminal region of CryIC apart thus enabling it to fold in such a way as to exhibit insecticidal activity.

It is most particularly preferred that the toxin fragment according to the invention comprises either:

i) an amino acid sequence from about amino acid 1 to about amino acid 620 in SEQ ID No. 6, or an amino acid sequence from about amino acid 1 to about amino acid 620 in SEQ ID No. 6, wherein with respect to the said sequence, at least one of the following alterations is present:

Ile at position 609 is replaced with Leu;

Ala at position 618 is replaced with Glu;

Ser at position 620 is replaced with Tyr, or ii) an amino acid sequence from about amino acid 1 to about amino acid 627 in SEQ ID No. 8, or an amino acid sequence from about amino acid 1 to about amino acid 627 in SEQ ID No. 8, wherein with respect to the said sequence, at least one of the following alterations is present:

Ile at position 616 is replaced with Leu;

Ala at position 625 is replaced with Glu;

Ser at position 627 is replaced with Tyr.

Whatever amino acid alterations are permitted, however, one or more of the following residues—indicated sequence-wise with respect to the CryIC sequence—is invariable: Phe (501); Val (478) Trp (479) and Thr (486).

The invention also includes a hybrid toxin comprising the above disclosed fragment or a toxin at least 85% similar to such a hybrid toxin which has substantially similar insecticidal activity, or receptor binding properties.

The invention still further includes pure proteins which are at least 90% identical to the toxin fragments or hybrid toxins according to the invention.

The invention still further includes recombinant DNA comprising a sequence encoding a protein having an amino acid sequence of the above disclosed toxins or fragments thereof. The invention still further includes recombinant DNA comprising the sequence from about nucleotide 1 to about nucleotide 1860 given in SEQ ID. No. 5 or DNA similar thereto encoding a substantially similar protein, or recombinant DNA comprising the sequence from about nucleotide 1 to about nucleotide 1881 in SEQ ID No. 7 or DNA similar thereto encoding a substantially similar protein.

By similar DNA is meant a test sequence which is capable of hybridizing to the inventive recombinant sequence. When the test and inventive sequences are double stranded the nucleic acid constituting the test sequence preferably has a TM within 20° C. of that of the inventive sequence. In the case that the test and inventive sequences are mixed together and denatured simultaneously, the TM values of the sequences are preferably within 10° C. of each other. More preferably the hybridization is performed under stringent conditions, with either the test or inventive DNA preferably being supported. Thus either a denatured test or inventive sequence is preferably first bound to a support and hybridization is effected for a specified period of time at a temperature of between 50° and 70° C. in double strength citrate buffered saline containing 0.1%SDS followed by rinsing of the support at the same temperature but with a buffer having a reduced SC concentration. Depending upon the degree of stringency required, and thus the degree of similarity of the sequences, such reduced concentration buffers are typically single strength SC containing 0.1%SDS, half strength SC containing 0.1%SDS and one tenth strength SC containing 0.1%SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1%SDS.

The recombinant DNA may further encode a protein having herbicide resistance, plant growth-promoting, anti-fungal, anti bacterial, anti-viral and/or anti-nematode properties. In the case that the DNA is to be introduced into a heterologous organism it may be modified to remove known mRNA instability motifs (such as AT rich regions) and polyadenylation signals, and/or codons which are preferred by the organism into which the recombinant DNA is to be inserted may be used so that expression of the thus modified DNA in the said organism yields substantially similar protein to that obtained by expression of the unmodified recombinant DNA in the organism in which the protein components of the hybrid toxin or toxin fragments are endogenous.

The invention still further includes a DNA sequence which is complementary to one which hybridizes under stringent conditions with the recombinant DNA according to the invention.

Also included in the present invention are: a vector containing such a recombinant (or complementary thereto) DNA sequence; a plant or micro-organism which includes, and enables expression of such DNA; plants transformed with such DNA; the progeny of such plants which contain the DNA stably incorporated and hereditable in a Mendelian manner, and/or the seeds of such plants and such progeny.

The invention still further includes protein derived from expression of the said DNA, and insecticidal protein produced by expression of the recombinant DNA within plants transformed therewith.

The invention still further includes an insecticidal composition containing one or more of the toxin fragments or toxins comprising them according to the invention; a process for combatting insects which comprises exposing them to such fragments or toxins or compositions, and an extraction process for obtaining insecticidal proteins from organic material containing them comprising submitting the material to maceration and solvent extraction.

The invention will be further apparent from the following description, which describes the production of B.t. hybrid toxin fragments according to the invention, taken in conjunction with the associated drawings and sequence listings.

FIG. 1 shows the generation of hybrid crystal protein genes via in vivo recombination. Tandem plasmids (pBD560 and pBD 650) carrying two truncated crystal protein genes in direct repeat orientation are constructed. The 5' located gene (open bar) lacks the protoxin encoding region (solid bar) and of the 3' located gene (dashed bar) part of the domain I encoding region is deleted. In vivo recombination between homologous regions (domain II and III) occurs in recA+ strain JM101. Selection against non-recombinants by digestion with NotI and BamHI and subsequent transformation results in sets of plasmids encoding hybrid crystal proteins.

Figure 2:
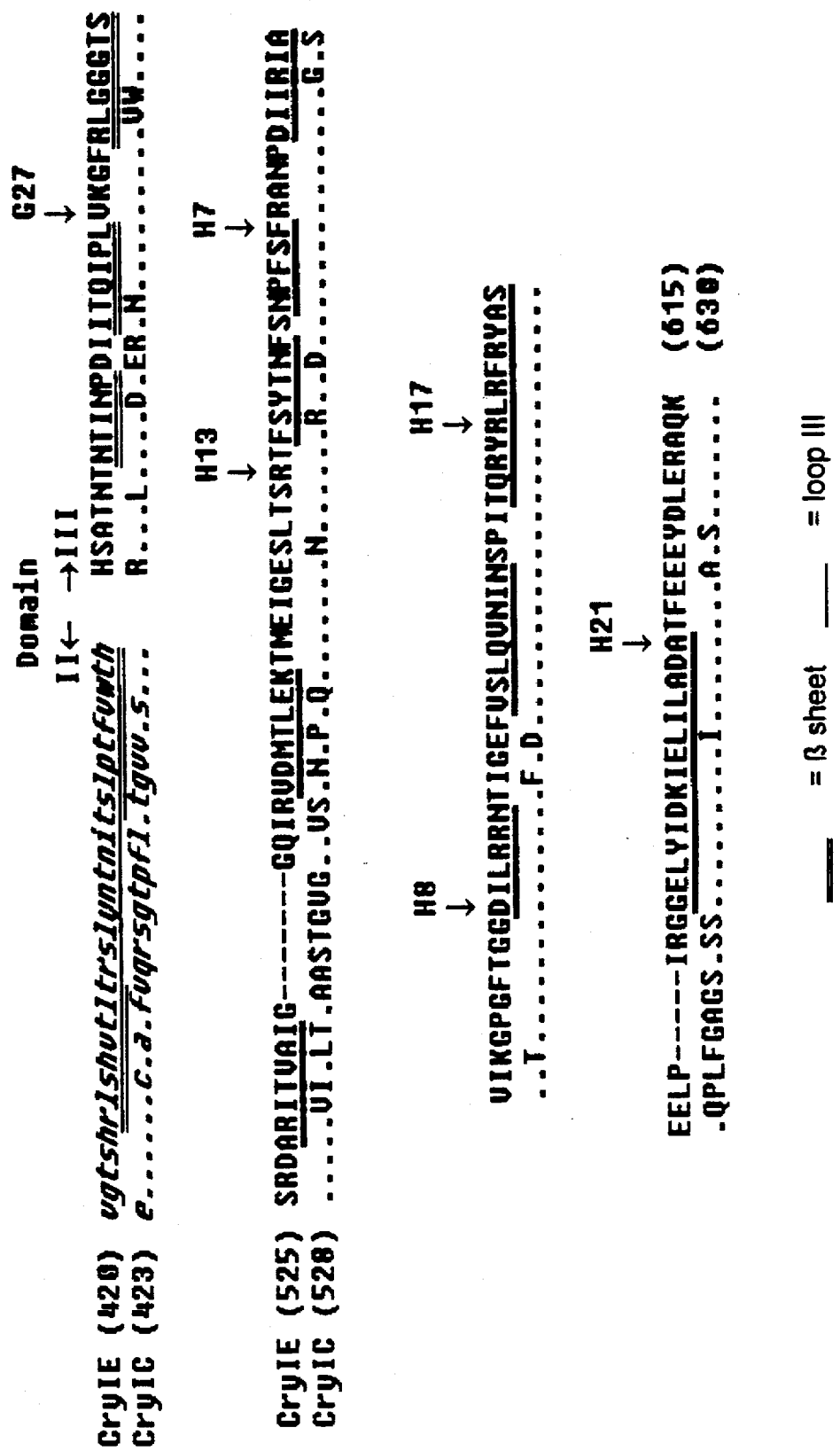

FIG. 2 shows the alignment of amino acid residues 420 to 630 of CryIE and CryIC. The border between domain II and III is indicated. Only amino acid residues of CryIC which differ from CryIE are depicted, identical residues are indicated by a dot. The positions of cross-over (G27, H13, H7, H8 H17 and H21) in the CryIE-CryIC hybrid toxin fragments according to the invention are indicated on the Figure.

Figure 3:
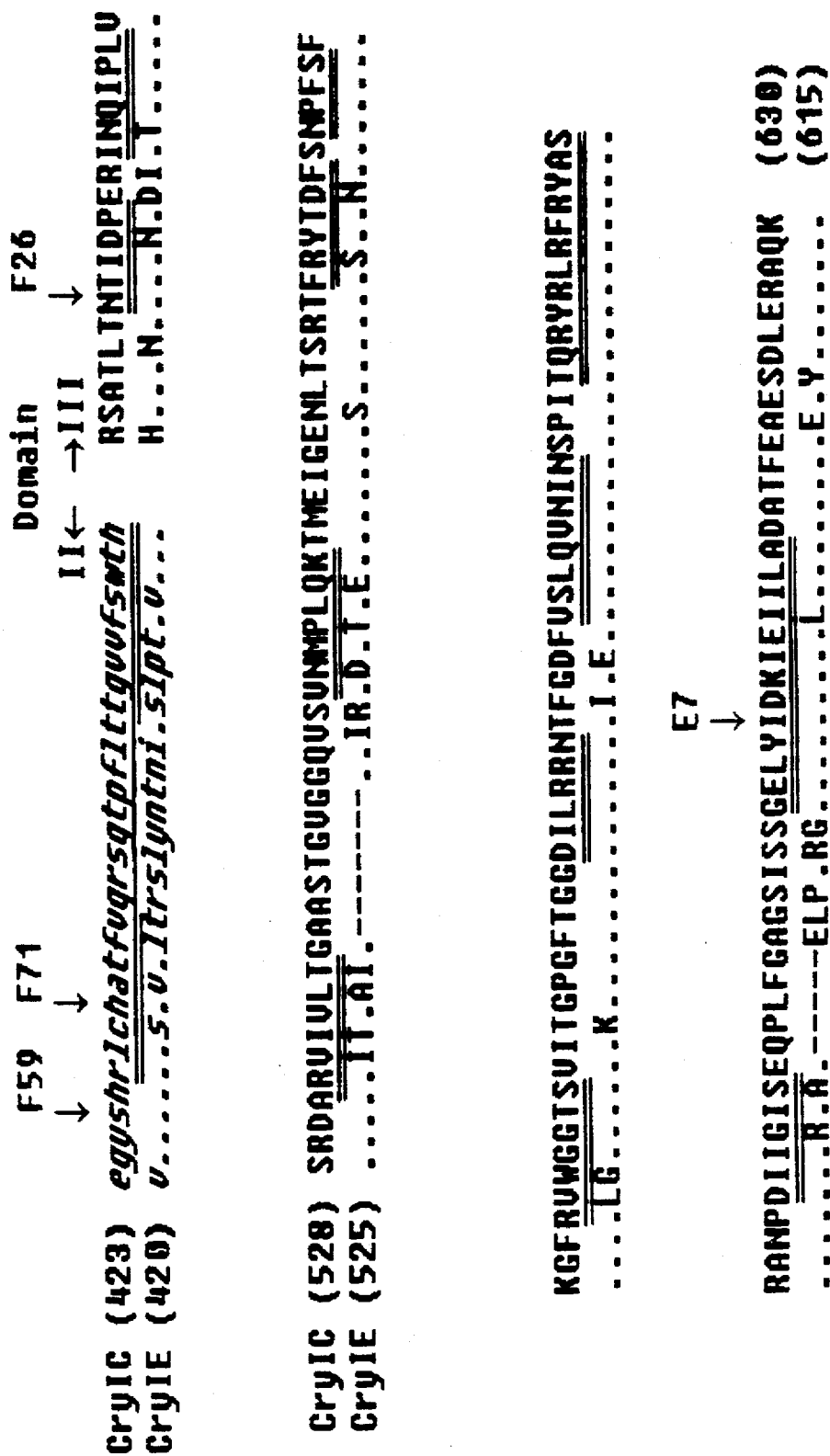

FIG. 3 shows the alignment of amino acid residues 420 to 630 of CryIE and CryIC. The border between domain II and III is indicated. Only amino acid residues of CryIC which differ from CryIE are depicted, identical residues are indicated by a dot. The positions of cross-over (F59, F71, F26, and E7) in the CryIC-CryIE hybrid toxin fragments are indicated on the Figure.

Figure 4A:
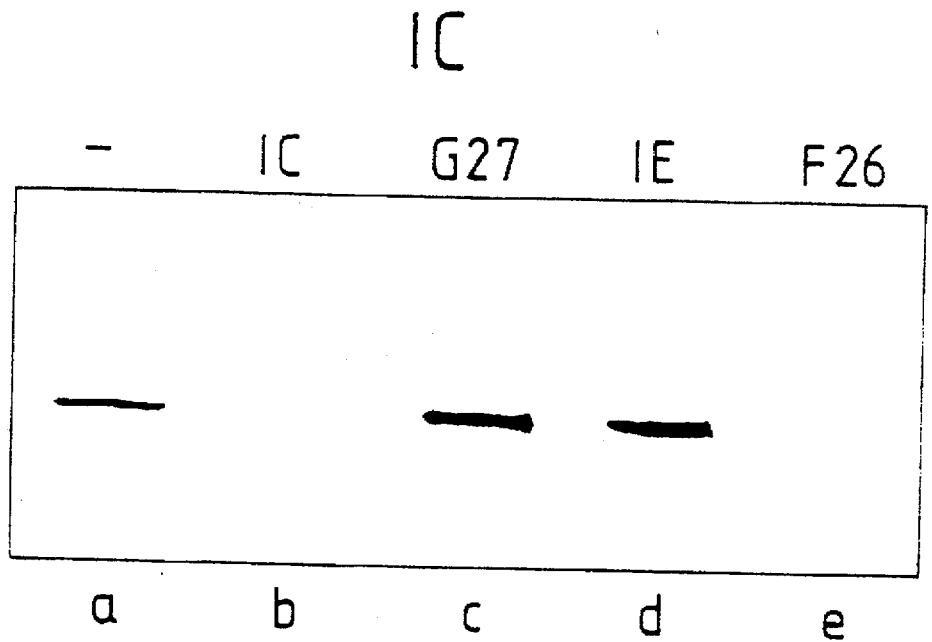
Figure 4B:
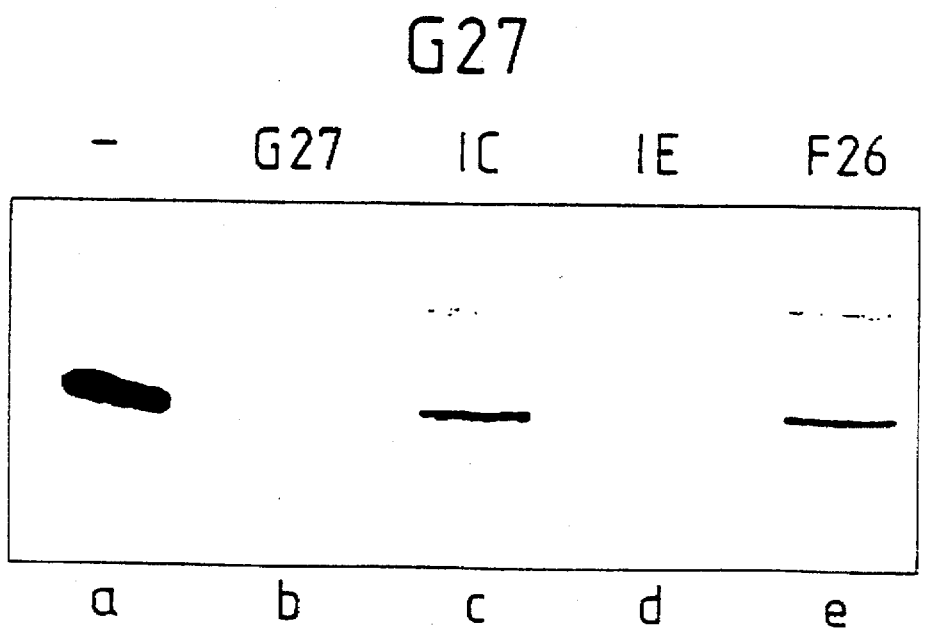

FIGS. 4a and 4b show the results of some heterologous competition experiments. Biotinylated CryIC (FIG. 4a) and G27 (FIG. 4b) are incubated with S. exigua BBMV vesicles in the absence (lanes a) or presence of an excess of unlabelled protein as indicated. After the incubation, the vesicles are washed, loaded on a SDS-polyacrylamide gel and blotted to a nitrocellulose membrane. Biotinylated crystal proteins, re-isolated with the vesicles, are visualized using streptavidin-peroxidase conjugate.

Figure 5:
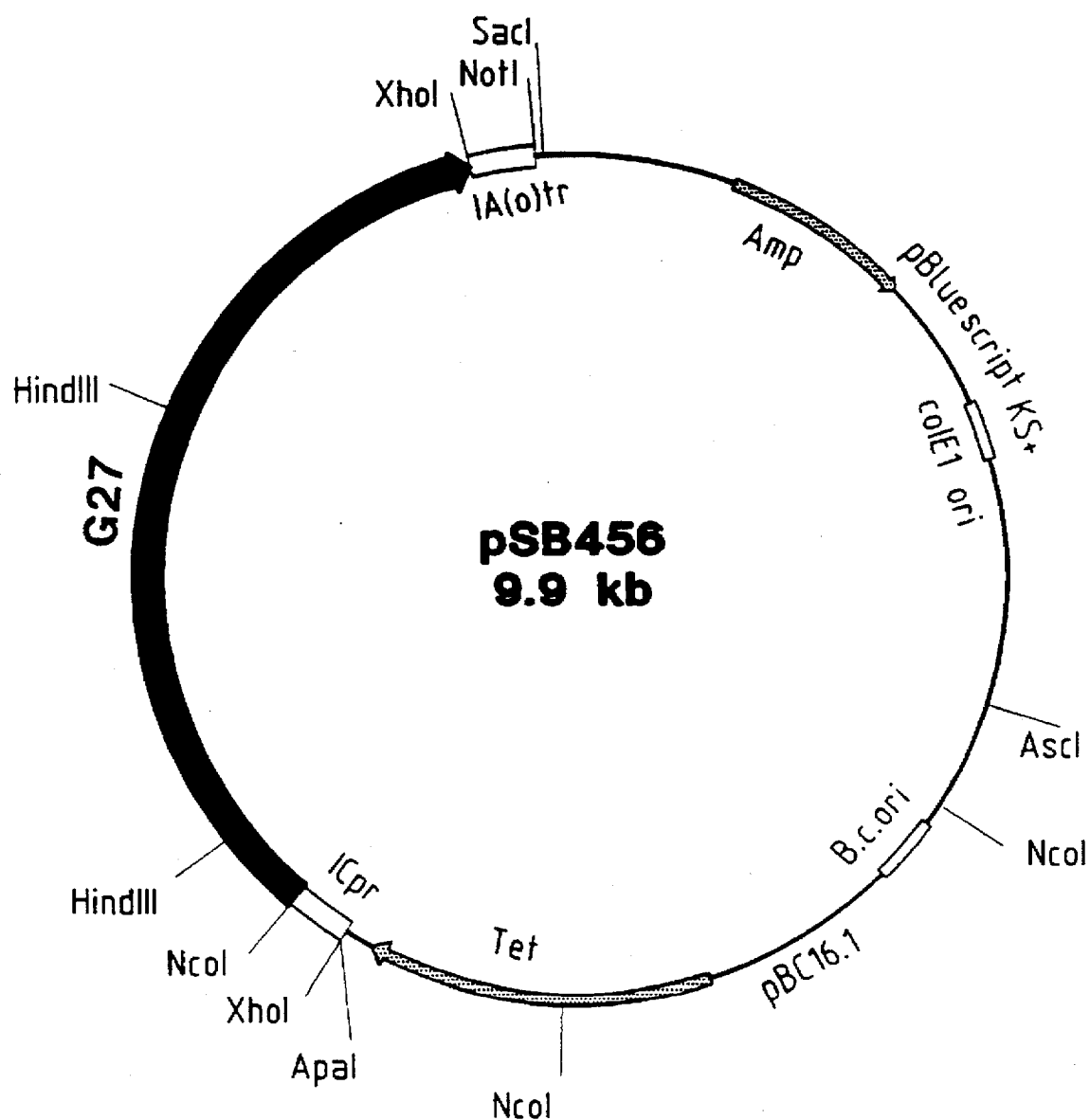

FIG. 5 shows the plasmid map of pSB456 which encodes the G27 hybrid toxin fragment and is used to transform the crystal toxin minus strain B.t. 51.

SEQ ID. No. 1 shows the nucleotide sequence of the CryIC gene from B.t. sub.sp. entomocidus 60.5.

SEQ ID No. 2 shows the amino acid sequence of the protein encoded by the CryIC gene shown in SEQ ID No. 1.

SEQ ID No. 3 shows the nucleotide sequence of the CryIE gene from B.t. sub.sp. kenyae 4FI.

SEQ ID No. 4 shows the amino acid sequence of the protein encoded by the CryIE gene shown in SEQ ID No. 3.

SEQ ID No. 5 shows the nucleotide sequence encoding a preferred CryIE/CryIC B.t. hybrid toxin fragment according to the invention.

SEQ ID No. 6 shows the amino acid sequence of the protein encoded by the nucleotide sequence shown in SEQ ID No. 5.

SEQ ID No. 7 shows the nucleotide sequence of a CryIA/CryIC hybrid toxin fragment according to the invention.

SEQ ID No. 8 shows the amino acid sequence of the protein encoded by the nucleotide sequence depicted in SEQ ID No.7.

Production of plasmids encoding Hybrid toxin fragments

In the production of plasmids carrying the CryIC or CryIE genes, *Escherichia coli* XLI-blue (Stratagene Inc.) is used as plasmid host except in cases were JM101 is used as recA+ background. A vector for the expression of crystal proteins in *E. coli* is derived from pKK233-2 (Pharmacia LKB Biotechnology). The size of pKK233-2 is reduced by deleting an EcoRI-PvuII fragment carrying the gene encoding tetracycline resistance. Subsequently a 6 bp XhoI linker is ligated into the HindIII site resulting in pBD10. Plasmid BK+ is created by insertion of a BglII linker in the SacI site of Bluescript SK+ (Stratagene Inc.). The polylinker of BK+ from BglII to XhoI is introduced between the NcoI-XhoI site in pBD10. The resulting expression vector pBD11 contains the highly expressed trc promoter, the lacZ ribosome binding site and ATG initiation codon. The initiation codon overlaps with a NcoI site and is followed by the polylinker to facilitate insertions into the vector. Transcription is terminated by the rrnB transcription terminator.

The cloning of the cryIC and cryIE genes from *B.t.* subsp. *entomocidus* 60.5 and *kenya* 4F1 respectively, is as described previously (Honée et al., 1990 (Appl. Environ. Microbiol. 56, pp 823–825); Visser et al., 1990 (J. Bacteriol. 172, pp 6783–6788)). For cloning purposes, an NcoI site overlapping with the start codon of cryIC is created by in vitro mutagenesis. A BglII site is created directly downstream of the translation termination codon of cryIC by site directed mutagenesis, resulting in the sequence A TAAGATCTGTT (stop-codon underlined). The NcoI-BglII fragment containing the cryIC coding region is ligated into pBD11, resulting in CryIC expression plasmid pBD150. pBD155 is a derivative of pBD150, in which the polylinker sequences 3' of cryIC are deleted.

A DraI fragment from pEM14 (Visser et al., 1990) containing the complete cryIE gene is cloned in the EcoRV site of SK+, resulting in plasmid pEM15. Subsequently, an NcoI site is introduced by site directed mutagenesis at the start-codon of the gene, and cryIE is transferred as an NcoI-XhoI fragment to pBD11 resulting in CryIE expression plasmid pBD160.

Plasmids carrying only toxic fragment encoding regions of the cryI genes are constructed. BglII linkers are ligated to XmnI sites present at bp position 1835 of cryIC, and to the HgiAI site at position 1839 of cryIE. Subsequently, NcoI-BglII fragments containing the cryIC (1835 bp) and cryIE (1839 bp) toxic fragment encoding regions are ligated into pBD11 resulting in pBD151 and pBD161 respectively as described below.

Tandem plasmids used for the generation of cryIC-cryIE hybrid genes are constructed as follows. BamHI linkers are ligated to pBD160 digested with HpaI. This DNA is incubated with BamHI and XhoI and the truncated cryIE gene running from bp 704 is ligated into pBD151 resulting in pBD560. To construct a tandem plasmid for the generation of cryIE-cryIC hybrids, pBD155 is digested with NsiI and XhoI. The fragment carrying the truncated cryIC gene, running from bp 266, is ligated into PstI/XhoI digested pBD161, resulting in plasmid pBD650. Due to polylinker sequences, unique NotI and BamH1 restriction sites are present between the truncated cryI genes present in the tandem plasmids pBD560 and pBD650.

DNA manipulations and construction of hybrid toxins.

All recombinant DNA techniques are as described by Sambrook et al. 1989 (in "Molecular Cloning", A Laboratory Manual: Cold Spring Harbour Press, Cold Spring Harbour), DNA sequencing is performed by the dideoxytriphosphate method with fluorescent dyes attached to the dideoxynucleotides. Analysis is automated by using an Applied Biosystems 370A nucleotide sequence analyzer.

The homology present between cryI genes permits intramolecular recombination in vivo. Two tandem plasmids are created by, each carrying two truncated crystal protein genes overlapping only in domains II and III. Therefore, recombination occurs only in regions encoding domains II and III. In frame recombinations, which can be selected for by restriction enzyme digestion, generate plasmids which express full size 140 kDa hybrid protoxins. To generate in vivo recombinants, a tandem plasmid (either pBD560 or pBD650; FIG. 2) is transferred to JM101. 5 μg of DNA is isolated from independently generated recombinants and is digested with NotI and BamHI cutting between the two truncated cryI genes to select against non-recombinants and the DNA is transformed to *E. coli* XL1-blue. 5 single colonies are grown and protein patterns and plasmid content are analysed. CryIC-CryIE and CryIE-CryIC hybrid toxins are generated using the tandem plasmids pBD560 and pBD650 respectively which are allowed to recombine in a recA+ background, DNA is isolated, digested and transferred to recA− strain as described above.

100 colonies of 20 independent experiments are analyzed on SDS-PAGE. 85% of these clones produce a 140 kDa protein indicating in frame recombinations between cryIC and cryIE, and cryIE and cryIC respectively. In *E. coli*, CryI proteins are produced as crystals which can be solubilized in vitro at high pH. Approximately 15% of hybrid toxins produced as above are solubilized at high pH. The recombinants producing soluble hybrid toxins are first classified using restriction enzymes, subsequently for each class the cross-over point of selected hybrids is determined by DNA sequence analysis. All cross-overs which resulted in soluble hybrid toxins occur in or very close to domain III.

Protein purification and analysis.

Crystal proteins are isolated essentially as described by Convents et al (J. Biol. Chem. 265, pp 1369–1375; Eur. J. Biochem, 195, pp 631–635). Briefly, recombinant E. coli are grown at 30° C. in 250 ml TB medium to an $OD_{600}$ of 10–15. Crystals isolated from the E. coli lysate are solubilized during incubation for 2 h in 20 mM $Na_2CO_3$, 10 mM dithiothreitol, 100 mM NaCl, pH10 at 37° C. The pH of the solution is lowered to 8 with Tris-HCl and incubated with trypsin. The toxin solution is dialysed against 20 mM Tris-HCl, 100 mM NaCl pH9. Subsequently the toxic fragment is purified on a Mono Q 5/5 column connected to a fast-protein liquid chromatography (FPLC) system (Pharmacia LKB Biotechnology). Proteins are separated by 7.5% sodium dodecyl sulfate-polyacrylamide gel electrophoreses.

Biochemical analysis and isolation of 65 kDa toxic fragments.

Isolated crystals of purified CryIC, CryIE and the hybrid proteins are solubilized at high pH and incubated with trypsin. Like CryIC and CryIE, all soluble hybrid toxins with cross-overs in domain III are converted to stable 65 kDa fragments. The 65 kDa fragments can be purified using anion exchange chromatography under similar conditions as the parental proteins. Hybrids F59 and F71 which have cross-overs in domain II, are completely degraded by trypsin. Apparently, although these hybrids do not precipitate as insoluble aggregates, trypsin cleavage sites buried in the parental proteins may become exposed to trypsin. Because of this phenomenon, no 65 kDa fragments are isolated from F59 and F71.

Table 1 shows the constitution of 5 CryIE-CryIC hybrid toxins: (G27; H8; H17; H13; H7 and H21) and 4 CryIC-CryIE hybrid toxins (F59; F71; F26; E7) with reference to the CryIC and CryIEE proteins from which they are derived. The amino acid sequences of the CryIE-CryIC toxins comprising the toxic fragments of the present invention run to amino acid 1189 of the CryIC parent protein. The amino acid sequences of the CryIC-CryIE hybrid toxins run to amino acid 1171 of the CryIE parent protein. Table 1 also shows the relative insecticidal effectiveness of these various hybrid toxins with respect to the CryIC and CryIE proteins.

TABLE 1

| TOX. | a.a IE | a.a. IC | M. sexta | S. exigua | M. brassicae. |
|---|---|---|---|---|---|
| IC | 0 | 28–627 | ++ | ++ | ++ |
| IE | 29–612 | 0 | ++ | – | – |
| G27 | 1–474 | 478–627 | ++ | ++(+) | +(+) |
| H8 | 1–497 | 501–627 | ++ | – | – |
| H17 | 1–529 | 533–627 | ++ | – | – |
| H7 | 1–577 | 588–627 | – | – | – |
| H21 | 1–605 | 621–627 |  |  |  |
| F59 | 421–612 | 1–423 | – | – | – |
| F71 | 428–612 | 1–430 | – | – | – |
| F26 | 455–612 (1171) | 1–458 | ++ | – | – |
| E7 | 588–612 (1171) | 1–602 | ++ | ++ | ++ |

Table 1. Constitution and toxicity of hybrid toxins with respect to the parent proteins. Most bioassays were performed with purified toxin fragments. In case of cryIC these run from about aa 28 to about aa 627, and in case of cryIE till 612. The length of complete protoxins is indicated between brackets.

Insect toxicity assays and insecticidal activity of cryIC/cryIE hybrid gene products.

Bacterial cultures are concentrated to $OD_{600}$ 6.0 and 100 µl are spotted on 2 $cm^2$ of artificial diet in a 24-well tissue culture plate. Alternatively, diluted samples of purified toxins are applied to the diet. Second instar larvae of either S. exigua, M. brassicae or M. sexta are fed on this diet (16 per sample dilution) for 5 days, after which the larval weight is scored. The relative growth (EC50, the concentration giving 50% growth reduction) is determined by calculating the ratio between the mean weight of larvae grown on diet supplemented with toxin and the mean weight of control larvae grown on a diet without toxin. M. sexta egg layers are supplied by Carolina Biological Supply Company, North Carolina, US.

The toxic fragments encoded by the hybrid gene products are tested for activity towards three different insect species as described above. M. sexta is susceptible to both CryIC and CryIE. As may be anticipated from their sensitivity to trypsin, hybrids F59 and F71 are not active against this insect (Table 1). Although H7 is converted by trypsin to stable 65 kDa proteins, it is not toxic to M. sexta. All of the other hybrids given in Table 1 are toxic and are apparently in the native, biologically active conformation.

The 65 kDa fragment of CryIC is highly toxic towards S.exigua and M.brassicae whereas CryIE is not. G27 (Table 1; FIG. 2), a CryIE-CryIC hybrid with a cross-over at the junction of domain II and III is active towards both insects. This demonstrates that domain III of CryIC confers full activity towards S.exigua and M.brassicae. Hybrid H8, which differs in only three amino acid residues (see FIG. 3) from G27, although active against M.sexta, is not active against S.exigua and M.brassicae.

F26 (Table 1, FIG. 3), the reciprocal hybrid of G27, in which domain III of CryIC has been exchanged by domain III of CryIE, is not active against S.exigua or M.brassicae. Apparently, although the protein is toxic to M.sexta, the CryIC sequences running from amino acid 28–462 are not sufficient to kill S.exigua and M.brassicae. Only when CryIC sequences up till amino acid residue 602 are present in the hybrid (E7), is insecticidal activity against these insects restored.

The present disclosure indicates that amino acid residues from 478–602 of CryIC can confer high insecticidal activity to CryIE against S.exigua and M.brassicae.

Biotinylation of crystal proteins and binding assays.

Biotinylation is performed using biotin-N-hydroxysuccinimide ester essentially as described by the manufacturer (Amersham). 1 mg of crystal protein is incubated with 40 µl biotinylation reagent in 50 mM NaHCO3, 150 mM NaCl pH8, for one hour at 20° C. The solution is loaded on a Sephadex 25 column equilibrated with the same buffer containing 0.1% BSA to remove unbound biotin and samples of the fractions are spotted on a nitrocellulose membrane. Fractions containing biotinylated crystal proteins are visualized using streptavidine-peroxidase conjugate (Amersham) which catalyzes the oxidation of luminol, resulting in chemiluminescence (ECL, Amersham) and pooled.

Brush border membrane vesicles are isolated as described by Wolfersberger et al. (1987) (Comp. Biochem. Physiol. 86a, pp 301–308) except that the vesicles are washed once more with isolation buffer containing 0.1% Tween 20. Binding of biotinylated crystal proteins to brush border membrane vesicles (100 µg/ml) is performed in 100 µl of PBS containing 1% BSA, 0.1% Tween-20 (pH 7.6). Vesicles (20 ug vessicle protein) are incubated with 10 ng biotinylated crystal proteins in the presence or absence of 1000 fold excess of unlabelled crystal proteins for 1 hour at 20° C. Subsequently, the vesicles are re-isolated by centrifugation for 10 minutes at 14,000 g in an Eppendorf centrifuge, washed twice with binding buffer, re-suspended in sample buffer, denatured by heating and loaded on 7.5% polyacrylamide gels. After electrophoresis, proteins are blotted to nitrocellulose membranes and biotinylated crystal proteins which are re-isolated with the vesicles are visualized by incubation of the nitrocellulose with streptavidin-peroxidase conjugate (Amersham) which catalyzes the oxidation of luminol, resulting in chemiluminescence (ECL, Amersham).

Since binding to epithelial gut cells is a key step in the mode of action of crystal proteins, the binding of crystal proteins to *S. exigua* brush border membrane vesicles is investigated in heterologous competition experiments. Competition experiments demonstrate that the binding of labeled CryIC (FIG. 4A, lane a) and labelled F26 (not shown) can be outcompeted by an excess of both unlabelled CryIC (lane b) or F26 (lane e) but not with an excess of G27 (lane c) or CryIE (lane d). Furthermore, binding of labelled G27 (FIG. 4B, land a) and labelled CryIE (not shown) can be outcompeted by an excess of G27 (lane b) or CryIE (lane d), but not with an excess of CryIC (lane a) or F26 (lane e). From these results it is concluded that G27 and CryIE recognize the same binding sites on *S. exigua* midgut membranes and that these sites differ from those which are recognized by CryIC and F26. The toxicity and binding assays combined demonstrate that G27 is as toxic as CryIC but that it binds a receptor different therefrom. As insects can develop resistance against a crystal protein by changing receptor binding characteristics G27 may be used in resistance management programs as an alternative to CryIC.

Expression of cryIE/cryIC hybrid toxin genes in heterologous systems.

The G27 cryIE/cryIC hybrid toxin gene is expressed in *E. coli* and the gene product exhibits at least the same insecticidal activity (at least against Spodoptera) as CryIC. Moreover, the said product exhibits an increased such activity when expressed in a *Bacillus thuringiensis* strain (see below). The gene encoding the G27 hybrid toxin is introduced into a suitable shuttle vector system, which is then introduced into an appropriate *B.t.* host. Such transformed cells are then cultured and the resulting toxin from both whole cultures and purified crystals is assayed for insecticidal activity.

Construction of a G27-containing shuttle vector, transformation of *Bt*51 and purification of toxin protein therefrom.

The gene encoding hybrid G27 (3.4 kbb) is cleaved from a pKK233 *E. coli* expression plasmid using NcoI and XhoI. The XhoI site is filled in using the Klenow fragment of *E. coli* DNA Polymerase I. The resulting fragment is ligated to NcoI/SmaI digested pSB635 (pBluescriptKS+, $P_{cryIC}$, and the CryIA(c) transcription terminator). The resulting plasmid, pSB453 is digested with ApaI and NotI yielding a 4.2 kbp fragment carrying the promoter, the hybrid G27 orf and the terminator. This fragment is ligated to ApaI/NotI digested pSB634 (shuttle vector containing pBC16.1 and pBluescriptKS+), yielding pSB456 (see FIG. 5). Plasmid DNA, isolated from *E. coli* DH10B, is used to transform the crystal toxin minus *B.t.* strain, *Bt*51. Positive isolates are tetracycline resistant, show the presence of pSB456, and contain large inclusions corresponding to a 135 kDa protein (as determined by SDS-PAGE. G27 hybrid toxin samples are prepared from cultures of transformed *B.t.*51 grown through sporulation at 30° C. in CYS-Tc[10] media. Insecticidal bioassays (Table 2) are performed on both full whole cultures and on washed crystal protein preparations. Controls include *Bt*51 (pSB440), containing the CryIC toxin, and *Bt*51 (pSB636), containing CryIE. Toxin concentrations are estimated by SDS-PAGE.

TABLE 2

Bioassay of the hybrid toxin G27 in comparison with CryIC and CryIE. The number of samples is given in parenthesis. The hybrid toxin G27 is about 50% more effective than either of CryIE or CryIC in respect of toxicity at least to *Spodoptera* sp.

| Toxin | LC$_{50}$ | | | | |
|---|---|---|---|---|---|
| | Whole Culture (ppt) | | | Washed Crystal Protein (ppm) | |
| CryIC | 56(2) | 36(2) | 40(4) | 7.8(2) | 8.1(4) |
| CryIE | 79(1) | 78(1) | 33(4) | 11.1(6) | 7.4(4) |
| G27 | 29(2) | 21(2) | 25(4) | 4.7(4) | 6.0(4) |
| Ratio (IC/G27) | 1.93 | 1.71 | 1.60 | 1.66 | 1.35 |

Although the present invention has been particularly described with reference to the production of the G27 hybrid toxin, the skilled man will appreciate that many other hybrid toxins having improved insecticidal characteristics may be produced according to the present disclosure. SEQ ID Nos. 7 and 8, for example, depict further hybrid toxins according to the invention which have improved insecticidal activity. Hybrid toxins may be produced comprising domain III of CryIC and an N-terminal of any other Cry protein. In terms of bioassays, the hybrid toxin carrying transformants may be grown in SOP media in order to expedite the assay procedures and reduce the volumes of material required. Moreover, the gene encoding G27 and/or other hybrid toxins according to the invention may be transferred into toxin-encoding strains of *B.t.* and/or integrated into the chromosome of selected strains of *B.t.* or indeed introduced into plant genomes to provide for insecticidal activity in situ within the plant per se. In this regard, it is particularly preferred that the recombinant DNA encoding the toxins is modified in that codons which are preferred by the plant into which the recombinant DNA is to be inserted are used so that expression of the thus modified DNA in the said plant yields substantially similar protein to that obtained by expression of the unmodified recombinant DNA in the organism in which the protein components of the hybrid toxin or toxin fragments are endogenous.

We claim:

1. A purified fragment of a *Bacillus thuringiensis* toxin comprising amino acids 1–620 of SEQ ID NO:6, or a purified fragment of a *Bacillus thuringiensis* toxin comprising amino acids 1–620 of SEQ ID NO:6 wherein at least one of the following substitutions is present:

Ile at position 609 is replaced with Leu;
Ala at position 618 is replaced with Glu;
Ser at position 620 is replaced with Tyr.

2. A purified fragment of a *Bacillus thuringiensis* toxin comprising amino acids 1–627 of SEQ ID NO:8, or a purified fragment of a *Bacillus thuringiensis* toxin comprising amino acids 1–627 of SEQ ID NO:8 wherein at least one of the following substitutions is present:

Ile at position 617 is replaced with Leu;
Ala at position 625 is replaced with Glu;
Ser at position 627 is replaced with Tyr.

3. A purified fragment of a *Bacillus thuringiensis* toxin which has at least 95% sequence identity with, and has the same insecticidal specificity and substantially the same insecticidal activity as the toxin fragment of claim 1 or 2.

4. An insecticidal composition comprising the toxin fragment of claim 1 or 2.

5. A process for controlling insects comprising exposing them to the insecticidal composition of claim 4.

6. A purified and isolated DNA encoding a protein comprising the sequence of the toxin fragment of claim 1 or 2.

7. A purified and isolated DNA comprising the sequence of nucleotides 1–1860 of SEQ ID NO:5 or nucleotides 1–1881 of SEQ ID NO:7.

8. A purified and isolated DNA according to claim 6 or 7 which further encodes a protein having herbicide resistance, plant-growth promoting, anti-fungal antibacterial antiviral and/or anti-nematode properties.

9. A purified and isolated DNA according to claim 6 or 7 which is modified to optimize expression in a heterologous host, said modifications selected from the group consisting of codon optimization for the intended host and removal of known mRNA instability motifs or polyadenylation signals.

10. A purified and isolated DNA according to claim 8 which is modified to optimize expression in a heterologous host, said modifications selected from the group consisting of codon optimization for the intended host and removal of known mRNA instability motifs or polyadenylation signals.

11. A recombinant vector comprising a DNA of claim 6, 7, 8, 9 or 10.

12. An isolated cell transformed with a DNA of claim 6, 7, 8, 9 or 10.

13. A method of producing a protein by expressing the DNA of claim 6, 7, 8, 9 or 10.

14. An isolated cell transformed with a vector of claim 11.

15. An insecticidal composition comprising the isolated cell of claim 12.

16. A process for controlling insects comprising exposing them to the insecticidal composition of claim 15.

17. Plants transformed with a DNA of claim 6, 7, 8, 9 or 10, the progeny of such plants which contain the DNA stably incorporated and heritable in a Mendelian manner.

18. Seeds of the plants of claim 17.

* * * * *